US007005258B1

(12) United States Patent
Beach et al.

(10) Patent No.: US 7,005,258 B1
(45) Date of Patent: Feb. 28, 2006

(54) CDC25 GENES, ENCODED PRODUCTS AND USES THEREOF

(75) Inventors: David H. Beach, Huntington Bay, NY (US); Konstantin Galaktionov, Cold Spring Harbor, NY (US)

(73) Assignee: The National Institutes of Health, Bethesda, MD (US)

( * ) Notice: Subject to any disclaimer, the term of this patent is extended or adjusted under 35 U.S.C. 154(b) by 775 days.

(21) Appl. No.: 09/699,580

(22) Filed: Oct. 30, 2000

Related U.S. Application Data

(63) Continuation of application No. 08/864,955, filed on May 29, 1997, now abandoned, which is a continuation of application No. 08/428,415, filed on Apr. 24, 1995, now Pat. No. 5,756,335, which is a continuation-in-part of application No. 08/379,685, filed on Jan. 26, 1995, now Pat. No. 5,770,423, which is a continuation-in-part of application No. 08/124,569, filed on Sep. 20, 1993, now Pat. No. 5,441,880, which is a continuation-in-part of application No. 07/793, 601, filed on Nov. 18, 1991, now abandoned, and a continuation-in-part of application No. 08/189,206, filed on Jan. 31, 1994, now Pat. No. 5,695,950, which is a continuation-in-part of application No. 07/878, 640, filed on May 5, 1992, now Pat. No. 5,294,538, and a continuation-in-part of application No. 07/793, 601, filed on Nov. 18, 1991, now abandoned.

(51) Int. Cl.
*C12Q 1/68* (2006.01)
*C07H 21/04* (2006.01)

(52) U.S. Cl. .......................... 435/6; 536/24.5
(58) Field of Classification Search .................. 514/44; 435/24.5
See application file for complete search history.

(56) References Cited

U.S. PATENT DOCUMENTS

| | | |
|---|---|---|
| 5,294,538 A | 3/1994 | Beach |
| 5,441,880 A | 8/1995 | Beach |

OTHER PUBLICATIONS

Agrawal et al. Molecular Medicine Today, 2000, vol 6, p 72-81.*
Branch TIBS 1998, vol. 23, p. 45-50.*
Opalinska et al. Nature Review, 2002, vol 1, p. 503-514.*
Jen et al. Stem Cells 2000, vol. 18, p 307-319.*
Baratte et al. Screening for Antimitotic Compounds Using the cdc25 Tyrosine Phosphatase, an Activator of the Mitosis-inducing p34cdc2/cyclinBcdc13 Protein Kinase. *Anticancer Research* 12, 873-880 (1992).
Camonis et al. Characterization, Cloning and Sequence Analysis of the CDC25 Gene which Controls the Cyclic AMP level of *Saccharomyces cerevisiae*. *EMBO J.* 5, 375-380 (1986).
Daniel, The CDC25 "Start" Gene of *Saccharomyces cerevisiae*: Sequencing of the Active C-terminal Fragment and Regional Homologies with Rhodopsin and Cytochrome P450. *Curr. Genet.* 10, 879-885 (1986).
Daniel et al. Clones from Two Different Genomic Regions Complement the cdc25 Start Mutation of *Saccharomyces*. *Curr. Genet.* 10, 643-646 (1986).
Dunphy et al. The cdc25 Protein Contains an Intrinsic Phosphatase Activity. *Cell* 67, 189-196 (1991).
Galaktionov et al. Specific Activation of cdc25 Tyrosine Phosphatases by B-Type Cyclins: Evidence for Multiple Roles of Mitotic Cyclins. *Cell* 67, 1181-1194 (1991).
Gautier et al. Cdc 25 is a Specific Tyrosine Phosphatase that Directly Activates p34cdc2. *Cell* 67, 197-211 (1991).
Gould et al. Complementation of the Mitotic Activator, p80cdc25, by a Human Protein-Tyrosine Phosphatase. *Science* 250, 1573-1576 (1990).
Jessus et al. Oscillation of MPF is Accompanied by Periodic Association between cdc25 and cdc2-Cyclin B. *Cell* 68, 323-332 (1992).
Jimenez et al. Complementation of Fission Yeast cdc2ts and cdc25ts Mutants Identifies Two Cell Cycle Genes from *Drosophila*: a cdc25 Homologue and String. *EMBO J.* 9, 3565-3571 (1990).
Kakizuka et al. A Mouse cdc25 Homolog is Differentially and Developmentally Expressed. *Genes & Development* 6, 578-590 (1992).
Kumagai et al. The cdc25 Protein Controls Tyrosine Dephosphorylation of the cdc2 Protein in a Cell-Free System. *Cell* 64, 903-914 (1991).
Lee et al. Cdc25 Encodes a Protein Phosphatase that Dephosphorylates p34cdc2. *Mol. Biol.* 3, 73-84 (1992).
Lerner. Tapping the Immunological Repertoire. *Nature* 299 (Oct. 14, 1982).

(Continued)

*Primary Examiner*—Andrew Wang
*Assistant Examiner*—Tracy Vivlemore
(74) *Attorney, Agent, or Firm*—Fish & Neave IP Group Ropes & Gray LLP

(57) ABSTRACT

Two previously undescribed human cdc25 genes, designated cdc25 A and cdc25 B, which have been shown to have an endogenous tyrosine phosphatase activity that can be specifically activated by B-type cyclin, in the complete absence of cdc2 are described. As a result of this work, new approaches to regulating the cell cycle in eukaryotic cells and, particularly, to regulating the activity of tyrosine specific phosphatases which play a key role in the cell cycle are available. Applicant's invention relates to methods of regulating the cell cycle and, specifically, to regulating activation of cdc2-kinase, through alteration of the activity and/or levels of tyrosine phosphatases or through alteration of the interaction of components of MPF. More specifically, the invention relates to inhibiting transcription or translation of mammalian CDC25A genes using oligonucleotides.

6 Claims, 25 Drawing Sheets

OTHER PUBLICATIONS

Millar et al. The cdc25 M-Phase Inducer: An Unconventional Protein Phosphatase. *Cell* 68, 407-410 (1992).

Millar et al. P55cdc25 is a Nuclear Protein Required for the Initiation of Mitosis in Human Cells. *PNAS* 88, 10500-10504 (1991).

Millar et al. P80cdc25 Mitotic Inducer is the Tyrosine Phosphatase that Activates p34cdc2 Kinase in Fission Yeast. *EMBO J*. 10, 4301-4309 (1991).

Moreno et al. Clues to Action of cdc25 Protein. *Nature* 351, 194 (1991).

Nagata et al. An additional Homolog of the Fission Yeast cdc25+ Gene Occurs in Humans and is Highly Expressed in Some Cancer Cells. *New Biologist* 3, 959-968 (1991).

Ogden et al. Isolation of a Novel Type of Mutation in the Mitotic Control of Schizosaccharomyces Pombe whose Phenotypic Expression is Dependent on the Genetic Background and Nutritional Environment. *Curr. Genet*. 10, 509-514 (1986).

Ohno et al. A Yeast Gene Coding for a Putative Protein Kinase Homologous to cdc25 Suppressing Protein Kinase. *FEBS* 222, 279-285 (1987).

Osmani et al. Parallel Activation of the NIMA and p34cdc2 Cell Cycle-Regulated Protein Kinases is Required to Initiate Mitosis in *A. nidulans*. *Cell* 67, 283-291 (1991).

Russell et al. Cdc25+ Functions as an Inducer in the Mitotic Control of Fission Yeast. *Cell* 45, 145-153 (1986).

Sadhu et al. Human Homolog of Fission Yeast cdc25 Mitotic Inducer is Predominantly Expressed in G2. *PNAS* 87, 5139-5143 (1990).

Strausfeld et al. Dephosphorylation and Activation of a p34cdc2/cyclin B Complex in vitro by Human CDC25 Protein. *Nature* 351, 242-245 (1991).

\* cited by examiner

```
CGAAAGGCCG GCCTTGGCTG CGACAGCCTG GGTAAGAGGT GTAGGTCGGC TTGGTTTTCT       60
GCTACCCGGA GCTGGGCAAG CGGGTTCGGA GAACAGCGAA GACAGCGTCA GCCTGGGCCG      120
TTGCCTCGAG GCTCTCGCCC GGCTTCTCTT GCCGACCCGC CACGTTTGTT TGGATTTAAT      180
CTTACAGCTG GTTGCCGGCG CCCGCCCGCC CGCTGGCCTC GCGGTGTGAG AGGGAAGCAC      240
CCGTGCCTGT GGCTGGTGGC TGGCGCCTGG AGGGTCCGCA CACCCGCCCG GCCGCGCCGC      300
TTTGCCCGCG GCAGCCGCGT CCCTGAACCG CGGAGTCGTG TTTGTGTTTG ACCCGCGGGC      360
GCCGGTGGCG CGCGGCCGAG GCCGGTGTCG GCGGGGCGGG GCGGTCGCGG CGGAGGCAGA      420
GGAAGAGGGA GCGGGAGCTC TGCGAGGCCG GGCGCCGCC ATG GAA CTG GGC CCG          474
                                            Met Glu Leu Gly Pro
                                             1               5

AGC CCC GCA CCG CGC CGC CTG CTC TTC GCC TGC AGC CCC CCT CCC GCG        522
Ser Pro Ala Pro Arg Arg Leu Leu Phe Ala Cys Ser Pro Pro Pro Ala
             10                  15                  20

TCG CAG CCC GTC GTG AAG GCG CTA TTT GGC GCT TCA GCC GCC GGG GGA        570
Ser Gln Pro Val Val Lys Ala Leu Phe Gly Ala Ser Ala Ala Gly Gly
             25                  30                  35

CTG TCG CCT GTC ACC AAC CTG ACC GTC ACT ATG GAC CAG CTG CAG GGT        618
Leu Ser Pro Val Thr Asn Leu Thr Val Thr Met Asp Gln Leu Gln Gly
         40                  45                  50

CTG GGC AGT GAT TAT GAG CAA CCA CTG GAG GTG AAG AAC AAC AGT AAT        666
Leu Gly Ser Asp Tyr Glu Gln Pro Leu Glu Val Lys Asn Asn Ser Asn
     55                  60                  65

CTG CAG AGA ATG GGC TCC TCC GAG TCA ACA GAT TCA GGT TTC TGT CTA        714
Leu Gln Arg Met Gly Ser Ser Glu Ser Thr Asp Ser Gly Phe Cys Leu
 70                  75                  80                  85

GAT TCT CCT GGG CCA TTG GAC AGT AAA GAA AAC CTT GAA AAT,CCT ATG        762
Asp Ser Pro Gly Pro Leu Asp Ser Lys Glu Asn Leu Glu Asn Pro Met
             90                  95                 100

AGA AGA ATA CAT TCC CTA CCT CAA AAG CTG TTG GGA TGT AGT CCA GCT        810
Arg Arg Ile His Ser Leu Pro Gln Lys Leu Leu Gly Cys Ser Pro Ala
            105                 110                 115

CTG AAG AGG AGC CAT TCT GAT TCT CTT GAC CAT GAC ATC TTT CAG CTC        858
Leu Lys Arg Ser His Ser Asp Ser Leu Asp His Asp Ile Phe Gln Leu
            120                 125                 130

ATC GAC CCA GAT GAG AAC AAG GAA AAT GAA GCC TTT GAG TTT AAG AAG        906
Ile Asp Pro Asp Glu Asn Lys Glu Asn Glu Ala Phe Glu Phe Lys Lys
            135                 140                 145

CCA GTA AGA CCT GTA TCT CGT GGC TGC CTG CAC TCT CAT GGA CTC CAG        954
Pro Val Arg Pro Val Ser Arg Gly Cys Leu His Ser His Gly Leu Gln
150                 155                 160                 165

GAG GGT AAA GAT CTC TTC ACA CAG AGG CAG AAC TCT GCC CAG CTC GGA       1002
Glu Gly Lys Asp Leu Phe Thr Gln Arg Gln Asn Ser Ala Gln Leu Gly
            170                 175                 180
```

Figure 1(a) - Panel A

```
ATG CTT TCC TCA AAT GAA AGA GAT AGC AGT GAA CCA GGG AAT TTC ATT      1050
Met Leu Ser Ser Asn Glu Arg Asp Ser Ser Glu Pro Gly Asn Phe Ile
            185                 190                 195

CCT CTT TTT ACA CCC CAG TCA CCT GTG ACA GCC ACT TTG TCT GAT GAG      1098
Pro Leu Phe Thr Pro Gln Ser Pro Val Thr Ala Thr Leu Ser Asp Glu
        200                 205                 210

GAT GAT GGC TTC GTG GAC CTT CTC GAT GGA GAG AAT CTG AAG AAT GAG      1146
Asp Asp Gly Phe Val Asp Leu Leu Asp Gly Glu Asn Leu Lys Asn Glu
    215                 220                 225

GAG GAG ACC CCC TCG TGC ATG GCA AGC CTC TGG ACA GCT CCT CTC GTC      1194
Glu Glu Thr Pro Ser Cys Met Ala Ser Leu Trp Thr Ala Pro Leu Val
230                 235                 240                 245

ATG AGA ACT ACA AAC CTT GAC AAC CGA TGC AAG CTG TTT GAC TCC CCT      1242
Met Arg Thr Thr Asn Leu Asp Asn Arg Cys Lys Leu Phe Asp Ser Pro
                250                 255                 260

TCC CTG TGT AGC TCC AGC ACT CGG TCA GTG TTG AAG AGA CCA GAA CGT      1290
Ser Leu Cys Ser Ser Ser Thr Arg Ser Val Leu Lys Arg Pro Glu Arg
            265                 270                 275

TCT CAA GAG GAG TCT CCA CCT GGA AGT ACA AAG ACG AGG AAG AGC ATG      1338
Ser Gln Glu Glu Ser Pro Pro Gly Ser Thr Lys Arg Arg Lys Ser Met
        280                 285                 290

TCT GGG GCC AGC CCC AAA GAG TCA ACT AAT CCA GAG AAG GCC CAT GAG      1386
Ser Gly Ala Ser Pro Lys Glu Ser Thr Asn Pro Glu Lys Ala His Glu
    295                 300                 305

ACT CTT CAT CAG TCT TTA TCC CTG GCA TCT TCC CCC AAA GGA ACC ATT      1434
Thr Leu His Gln Ser Leu Ser Leu Ala Ser Ser Pro Lys Gly Thr Ile
310                 315                 320                 325

GAG AAC ATT TTG GAC AAT GAC CCA AGG GAC CTT ATA GGA GAC TTC TCC      1482
Glu Asn Ile Leu Asp Asn Asp Pro Arg Asp Leu Ile Gly Asp Phe Ser
                330                 335                 340

AAG GGT TAT CTC TTT CAT ACA GTT GCT GGG AAA CAT CAG GAT TTA AAA      1530
Lys Gly Tyr Leu Phe His Thr Val Ala Gly Lys His Gln Asp Leu Lys
            345                 350                 355

TAC ATC TCT CCA GAA ATT ATG GCA TCT GTT TTG AAT GGC AAG TTT GCC      1578
Tyr Ile Ser Pro Glu Ile Met Ala Ser Val Leu Asn Gly Lys Phe Ala
        360                 365                 370

AAC CTC ATT AAA GAG TTT GTT ATC ATC GAC TGT CGA TAC CCA TAT GAA      1626
Asn Leu Ile Lys Glu Phe Val Ile Ile Asp Cys Arg Tyr Pro Tyr Glu
    375                 380                 385

TAC GAG GGA GGC CAC ATC AAG GGT GCA GTG AAC TTC CAC ATG GAA GAA      1674
Tyr Glu Gly Gly His Ile Lys Gly Ala Val Asn Leu His Met Glu Glu
390                 395                 400                 405

GAG GTT GAA GAC TTC TTA TTG AAG AAG CCC ATT GTA CCT ACT GAT GGC      1722
Glu Val Glu Asp Phe Leu Leu Lys Lys Pro Ile Val Pro Thr Asp Gly
                410                 415                 420
```

Figure 1(b) - Panel A

```
AAG CGT GTC ATT GTT GTC TTT CAC TGC GAG TTT TCT TCT GAG AGA GGT    1770
Lys Arg Val Ile Val Val Phe His Cys Glu Phe Ser Ser Glu Arg Gly
        425             430             435

CCC CGC ATG TGC CGG TAT GTG AGA GAG AGA GAT CGC CTG GGT AAT GAA    1818
Pro Arg Met Cys Arg Tyr Val Arg Glu Arg Asp Arg Leu Gly Asn Glu
        440             445             450

TAC CCC AAA CTC CAC TAC CCT GAG CTG TAT GTC CTG AAG GGG GGA TAC    1866
Tyr Pro Lys Leu His Tyr Pro Glu Leu Tyr Val Leu Lys Gly Gly Tyr
        455             460             465

AAG GAG TTC TTT ATG AAA TGC CAG TCT TAC TGT GAG CCC CCT AGC TAC    1914
Lys Glu Phe Phe Met Lys Cys Gln Ser Tyr Cys Glu Pro Pro Ser Tyr
470             475             480             485

CGG CCC ATG CAC CAC GAG GAC TTT AAA GAA GAC CTG AAG AAG TTC CGC    1962
Arg Pro Met His His Glu Asp Phe Lys Glu Asp Leu Lys Lys Phe Arg
        490             495             500

ACC AAG AGC CGG ACC TGG GCA GGG GAG AAG AGC AAG AGG GAG ATG TAC    2010
Thr Lys Ser Arg Thr Trp Ala Gly Glu Lys Ser Lys Arg Glu Met Tyr
        505             510             515

AGT CGT CTG AAG AAG CTC TGAGGCGGC AGGACCAGCC AGCAGCAGCC            2058
Ser Arg Leu Lys Lys Leu
        520

CAAGCTTCCC TCCATCCCCC TTTACCCTCT TTCCTGCAGA GAAACTTAAG CAAAGGGGAC    2118
ACCTGTGTGA CATTTGGAGA GGGGGCCTGG GACTTCCATG CCTTAAACCT ACCTCCCACA    2178
CTCCCAAGGT TGCAGCCCAG GGCATCTTGC TGGCTACGCC TCTTCTGTCC CTGTTAGACG    2238
TCCTCCGTCC ATATCAGAAC TGTGCCACAA TGCAGTTCTG AGCACCGTGT CAAGCTGCTC    2298
TCAGCCACAG TGGGATGAAC CAGCCGGGGC CTTATCGGGC TCCAGCATCT CATGAGGGGA    2358
GAGGAGACGG AGGGGAGTAG AGAAGTTTAC ACAGAAATGC TGCTGGCCAA ATAGCAAAGA    2418
G                                                                   2419
```

Figure 1(c) - Panel A

```
CTGCCCTGCG CCCGGCCCTC CAGCCAGCCT GCCAGCTGTG CCGGCGTTTG TTGGTCTGCC      60

CGCCCCGCCG CG ATG GAG GTG CCC CAG CCG GAG CCC GCG CCA GGC TCG        108
              Met Glu Val Pro Gln Pro Glu Pro Ala Pro Gly Ser
                1               5                  10

GCT CTC AGT CCA GCA GGC GTG TGC GGT GGC GCC CAG CGT CCG GGC CAC      156
Ala Leu Ser Pro Ala Gly Val Cys Gly Gly Ala Gln Arg Pro Gly His
         15                  20                  25

CTC CCG GGC CTC CTG CTG GGA TCT CAT GGC CTC CTG GGG TCC CCG GTG      204
Leu Pro Gly Leu Leu Leu Gly Ser His Gly Leu Leu Gly Ser Pro Val
         30                  35                  40

CGG GCG GCC GCT TCC TCG CCG GTC ACC ACC CTC ACC CAG ACC ATG CAC      252
Arg Ala Ala Ala Ser Ser Pro Val Thr Thr Leu Thr Gln Thr Met His
45                  50                  55                  60

GAC CTC GCC GGG CTC GGC AGC CGC AGC CGC CTG ACG CAC CTA TCC CTG      300
Asp Leu Ala Gly Leu Gly Ser Arg Ser Arg Leu Thr His Leu Ser Leu
                 65                  70                  75

TCT CGA CGG GCA TCC GAA TCC TCC CTG TCG TCT GAA TCC TCC GAA TCT      348
Ser Arg Arg Ala Ser Glu Ser Ser Leu Ser Ser Glu Ser Ser Glu Ser
             80                  85                  90

TCT GAT GCA GGT CTC TGC ATG GAT TCC CCC AGC CCT ATG GAC CCC CAC      396
Ser Asp Ala Gly Leu Cys Met Asp Ser Pro Ser Pro Met Asp Pro His
         95                  100                 105

ATG GCG GAG CAG ACG TTT GAA CAG GCC ATC CAG GCA GCC AGC CGG ATC      444
Met Ala Glu Gln Thr Phe Glu Gln Ala Ile Gln Ala Ala Ser Arg Ile
     110                 115                 120

ATT CGA AAC GAG CAG TTT GCC ATC AGA CGC TTC CAG TCT ATG CCG GTG      492
Ile Arg Asn Glu Gln Phe Ala Ile Arg Arg Phe Gln Ser Met Pro Val
125                 130                 135                 140

AGG CTG CTG GGC CAC AGC CCC GTG CTT CGG AAC ATC ACC AAC TCC CAG      540
Arg Leu Leu Gly His Ser Pro Val Leu Arg Asn Ile Thr Asn Ser Gln
                145                 150                 155

GCG CCC GAC GGC CGG AGG AAG AGC GAG GCC GGC AGT GGA GCT GCC AGC      588
Ala Pro Asp Gly Arg Arg Lys Ser Glu Ala Gly Ser Gly Ala Ala Ser
            160                 165                 170

AGC TCT GGG GAA GAC AAG GAG AAT GAT GGA TTT GTC TTC AAG ATG CCA      636
Ser Ser Gly Glu Asp Lys Glu Asn Asp Gly Phe Val Phe Lys Met Pro
        175                 180                 185

TGG AAG CCC ACA CAT CCC AGC TCC ACC CAT GCT CTG GCA GAG TGG GCC      684
Trp Lys Pro Thr His Pro Ser Ser Thr His Ala Leu Ala Glu Trp Ala
    190                 195                 200

AGC CGC ACG GAA GCC TTT GCC CAG AGA CCC AGC TCG GCC CCC GAC CTG      732
Ser Arg Thr Glu Ala Phe Ala Gln Arg Pro Ser Ser Ala Pro Asp Leu
205                 210                 215                 220

ATG TGT CTC AGT CCT GAC CGG AAG ATG GAA GTG GAG GAG CTC AGC CCC      780
Met Cys Leu Ser Pro Asp Arg Lys Met Glu Val Glu Glu Leu Ser Pro
            225                 230                 235
```

Figure 1(d) - Panel B

```
CTC GCC CTA GGT CGC TTC TCT CTG ACC CCT GCA GAG GGG GAT ACT GAG      828
Leu Ala Leu Gly Arg Phe Ser Leu Thr Pro Ala Glu Gly Asp Thr Glu
        240                 245                 250

GAA GAT GAT GGA TTT GTG GAC ATC CTA GAG AGT GAC TTA AAG GAT GAT      876
Glu Asp Asp Gly Phe Val Asp Ile Leu Glu Ser Asp Leu Lys Asp Asp
        255                 260                 265

GAT GCA GTT CCC CCA GGC ATG GAG AGT CTC ATT AGT GCC CCA CTC GTC      924
Asp Ala Val Pro Pro Gly Met Glu Ser Leu Ile Ser Ala Pro Leu Val
        270                 275                 280

AAG ACC TTG GAA AAG GAA GAG GAA AAG GAC CTC GTC ATG TAC AGC AAG      972
Lys Thr Leu Glu Lys Glu Glu Glu Lys Asp Leu Val Met Tyr Ser Lys
285                 290                 295                 300

TGC CAG CGC CTC TTC CGC TCT CCG TCC ATG CCC TGC AGC GTG ATC CGG     1020
Cys Gln Arg Leu Phe Arg Ser Pro Ser Met Pro Cys Ser Val Ile Arg
                305                 310                 315

CCC ATC CTC AAG AGG CTG GAG CGC CCC CAG GAC AGG GAC ACG CCC GTG     1068
Pro Ile Leu Lys Arg Leu Glu Arg Pro Gln Asp Arg Asp Thr Pro Val
            320                 325                 330

CAG AAT AAG CGG AGG CGG AGC GTG ACC CCT CCT GAG GAG CAG CAG GAG     1116
Gln Asn Lys Arg Arg Arg Ser Val Thr Pro Pro Glu Glu Gln Gln Glu
            335                 340                 345

GCT GAG GAA CCT AAA GCC CGC GTC CTC CGC TCA AAA TCA CTG TGT CAC     1164
Ala Glu Glu Pro Lys Ala Arg Val Leu Arg Ser Lys Ser Leu Cys His
350                 355                 360

GAT GAG ATC GAG AAC CTC CTG GAC AGT GAC CAC CGA GAG CTG ATT GGA     1212
Asp Glu Ile Glu Asn Leu Leu Asp Ser Asp His Arg Glu Leu Ile Gly
365                 370                 375                 380

GAT TAC TCT AAG GCC TTC CTC CTA CAG ACA GTA GAC GGA AAG CAC CAA     1260
Asp Tyr Ser Lys Ala Phe Leu Leu Gln Thr Val Asp Gly Lys His Gln
                385                 390                 395

GAC CTC AAG TAC ATC TCA CCA GAA ACG ATG GTG GCC CTA TTG ACG GGC     1308
Asp Leu Lys Tyr Ile Ser Pro Glu Thr Met Val Ala Leu Leu Thr Gly
            400                 405                 410

AAG TTC AGC AAC ATC GTG GAT AAG TTT GTG ATT GTA GAC TGC AGA TAC     1356
Lys Phe Ser Asn Ile Val Asp Lys Phe Val Ile Val Asp Cys Arg Tyr
            415                 420                 425

CCC TAT GAA TAT GAA GGC GGG CAC ATC AAG ACT GCG GTG AAC TTG CCC     1404
Pro Tyr Glu Tyr Glu Gly Gly His Ile Lys Thr Ala Val Asn Leu Pro
            430                 435                 440

CTG GAA CGC GAC GCC GAG AGC TTC CTA CTC AAG AGC CCC ATC GCG CCC     1452
Leu Glu Arg Asp Ala Glu Ser Phe Leu Leu Lys Ser Pro Ile Ala Pro
445                 450                 455                 460

TGT AGC CTG GAC AAG AGA GTC ATC CTC ATT TTC CAC TGT GAA TTC TCA     1500
Cys Ser Leu Asp Lys Arg Val Ile Leu Ile Phe His Cys Glu Phe Ser
                465                 470                 475
```

Figure 1(e) - Panel B

```
TCT GAG CGT GGG CCC CGC ATG TGC CGT TTC ATC AGG GAA CGA GAC CGT      1548
Ser Glu Arg Gly Pro Arg Met Cys Arg Phe Ile Arg Glu Arg Asp Arg
                480                 485                 490

GCT GTC AAC GAC TAC CCC AGC CTC TAC TAC CCT GAG ATG TAT ATC CTG      1596
Ala Val Asn Asp Tyr Pro Ser Leu Tyr Tyr Pro Glu Met Tyr Ile Leu
            495                 500                 505

AAA GGC GGC TAC AAG GAG TTC TTC CCT CAG CAC CCG AAC TTC TGT GAA      1644
Lys Gly Gly Tyr Lys Glu Phe Phe Pro Gln His Pro Asn Phe Cys Glu
        510                 515                 520

CCC CAG GAC TAC CGG CCC ATG AAC CAC GAG GCC TTC AAG GAT GAG CTA      1692
Pro Gln Asp Tyr Arg Pro Met Asn His Glu Ala Phe Lys Asp Glu Leu
525                 530                 535                 540

AAG ACC TTC CGC CTC AAG ACT CGC AGC TGG GCT GGG GAG CGG AGC CGG      1740
Lys Thr Phe Arg Leu Lys Thr Arg Ser Trp Ala Gly Glu Arg Ser Arg
                545                 550                 555

CGG GAG CTC TGT AGC CGG CTG CAG GAC CAG TGAGGGCCT GCGCCAGTCC         1790
Arg Glu Leu Cys Ser Arg Leu Gln Asp Gln
                560                 565

TGCTACCTCC CTTGCCTTTC GAGGCCTGAA GCCAGCTGCC CTATGGGCCT GCCGGGCTGA    1850
GGGCCTGCTG GAGGCCTCAG GTGCTGTCCA TGGGAAAGAT GGTGTGGTGT CCTGCCTGTC    1910
TGCCCCAGCC CAGATTCCCC TGTGTCATCC CATCATTTTC CATATCCTGG TGCCCCCCAC    1970
CCCTGGAAGA GCCCAGTCTG TTGAGTTAGT TAAGTTGGGT TAATACCAGC TTAAAGGCAG    2030
TATTTTGTGT CCTCCAGGAG CTTCTTGTTT CCTTGTTAGG GTTAACCCTT CATCTTCCTG    2090
TGTCCTGAAA CGCTCCTTTG TGTGTGTGTC AGCTGAGGCT GGGAGAGCC GTGGTCCCTG     2150
AGGATGGGTC AGAGCTAAAC TCCTTCCTGG CCTGAGAGTC AGCTCTCTGC CCTGTGTACT    2210
TCCCGGCCCA GGGCTGCCCC TAATCTCTGT AGGAACCGTG GTATGTCTGC CATGTTGCCC    2270
CTTTCTCTTT TCCCCTTTCC TGTCCCACCA TACGAGCACC TCCAGCCTGA ACAGAAGCTC    2330
TTACTCTTTC CTATTTCAGT GTTACCTGTG TGCTTGGTCT GTTTGACTTT ACGCCCATCT    2390
CAGGACACTT CCGTAGACTG TTTAGGTTCC CCTGTCAAAT ATCAGTTACC CACTCGGTCC    2450
CAGTTTTGTT GCCCCAGAAA GGGATGTTAT TATCCTTGGG GGCTCCCAGG GCAAGCGTTA    2510
AGGCCTGAAT CATGAGCCTG CTGGAAGCCC AGCCCCTACT GCTGTGAACC CTGGGCCTG    2570
ACTGCTCAGA ACTTGCTGCT GTCTTGTTGC GGATGGATGG AAGGTTGGAT GGATGGGTGG    2630
ATGGCCGTGG ATGGCCGTGG ATGCGCAGTG CCTTGCATAC CCAAACCAGG TGGCAGCCTT    2690
TTGTTGAGCA TGACACCTGC AGCAGGAATA TATGTGTGCC TATTTGTGTG GACAAAAATA    2750
TTTACACTTA GGGTTTGGAG CTATTCAAGA GGAAATGTCA CAGAAGCAGC TAAACCAAGG    2810
ACTGAGCACC CTCTGGATTC TGAATCTCAA GATGGGGGCA GGGCTGTGCT TGAAGGCCCT    2870
GCTGAGTCAT CTGTTAGGGC CTTGGTTCAA TAAAGCACTG AGCAAGTTCA GAAAAAAAAA    2930
AAAAAAAAA                                                           2940
```

Figure 1(f) - Panel B

Figure 2

CDC25 GENES, ENCODED PRODUCTS AND USES THEREOF

RELATED APPLICATIONS

This application is a continuation of U.S. Ser. No. 08/864,955, filed on 29 May 1997, now abandoned, which is a continuation of U.S. Ser. No. 08/428,415, filed on 24 Apr. 1995, now U.S. Pat. No. 5,756,335, which is a continuation-in-part of U.S. Ser. No. 08/379,685, filed on 26 Jan. 1995, now U.S. Pat. No. 5,770,423, which is a continuation-in-part of U.S. Ser. No. 08/124,569, filed on 20 Sep. 1993, now U.S. Pat. No. 5,441,880, which is a continuation-in-part of U.S. Ser. No. 07/793,601, filed on 18 Nov. 1991, now abandoned, and is a continuation-in-part of U.S. Ser. No. 08/189,206, filed on 31 Jan. 1994, now U.S. Pat. No. 5,695,950, which is a continuation-in-part of U.S. Ser. No. 07/878,640, filed on 5 May 1992, now U.S. Pat. No. 5,294,538, and is a continuation-in-part of U.S. Ser. No. 07/793,601, filed on 18 Nov. 1991, now abandoned, the specification and claims of which are incorporated by reference herein.

GOVERNMENT FUNDING

Work described herein was supported by National Institutes of Health Grant No. R01 GM 39620. The United States Government has certain rights in the invention.

BACKGROUND OF THE INVENTION

In eukaryotic cells, mitosis is initiated following the activation of a protein kinase known as "M-phase promoting factor" (MPF; also known as the H-phase specific histone kinase, or more simply as the H-phase kinase) This kinase consists of at least three subunits: the catalytic subunit (cdc2), a regulatory subunit (cyclin B) and a low molecular weight subunit (p13-Sucl) (Brizuela, L. et al., *EMBO J.* 6:3507–3514 (1987); Dunphy, W. et al., *Cell* 54:423–431 (1988); Gautier, J. et al., *Cell* 54:433–439 (1988); Arion, D. et al., *Cell* 55:371–378 (1988); Draetta, G. et al., *Cell* 56:829–838 (1989); Booher, R. et al., *Cell* 58:485–497 (1989); Labbe, J- C. et al. *EMBO J.* 8:3053–3058 (1989); Meijer, L. et al., *EMBO J.* 8:2275–2282 (1989); Gautier, J. et al., *Cell* 60:487–494 (1990); Gautier, J. and J. Maller, *EMBO J.* 10:177–182 (1991)). cdc2 and related kinases also associate with other cyclins (Giordana, A. et al., *Cell* 58:981–990 (1989); Draetta, G. et al., *Cell* 56:829–838 (1989); Richardson, H. E. et al., *Cell* 59:1127–1133 (1989)), and comprise a family of related enzymes that act at various stages of the division cycle (Paris, J. et al., *Proc. Natl. Acad. Sci. USA* 88:1039–1043 (1990); Elledge, S. J. and M. R. Spottswood, *EMBO J.* 10:2653–2659 (1991); Tsai, L- H. et al., *Nature* 353:174–177 (1991)).

The cdc2/cyclin B enzyme is subject to multiple levels of control. Among these, the regulation of the catalytic subunit by tyrosine phosphorylation is the best understood. In a variety of eukaryotic cell types, cdc2 is one of the most heavily tyrosine phosphorylated proteins (Draetta, G. et al., *Nature* 336:738–744 (1988); Dunphy, W. G. and J. W. Newport, *Cell* 58:181–431 (1989); Morla, A. O. et al., *Cell* 58:193–203 (1989)). Phosphorylation of the tyrosine 15 and also threonine 14 residues of cdc2 is regulated, in part, by the accumulation of cyclin above a threshold level at which association with cdc2 occurs (Solomon, M. J. et al., *Cell* 63:1013–1024 (1990)). Tyrosine phosphorylation inhibits the cdc2/cyclin B enzyme, and tyrosine dephosphorylation, which occurs at the onset of mitosis, directly activates the pre-MPF complex (Gautier J. et al., *Nature* 339:626–629 (1989); Labbe, J. C. et al., *EMBO J.* 8:3053–3058 (1989); Morla, A. O. et al., *Cell* 58:193–203 (1989); Dunphy, W. G. and J. W. Newport, *Cell* 58:181–431 (1989); Morla, A. O. et al., *Cell* 58:193–203 (1989); Gould, K. and P. Nurse, *Nature* 342:39–45 (1989); Jessus, C. et al., *FEBS LETTERS* 266:4–8 (1990)).

Given the role of cdc2 dephosphorylation in activation of MPF, there is much interest in the regulation of the cdc2 phosphatase. Genetic studies in fission yeast have established that the cdc25 gene function is essential for the initiation of mitosis (Nurse, P. et al., *Mol. Gen. Genet.* 146:167–178 (1976). The cdc25 gene product serves as a rate-determining activator of the cdc2 protein kinase (Russell, P. and P. Nurse, *Cell* 45:145–153 (1986); Ducommun, B. et al., *Biochem. Biophys. Res. Common.* 167:301–309 (1990); Moreno, S. et al., *Nature* 344:549–552 (1990)). Moreover, the mutant cdc2-F15, whose product cannot be phosphorylated on tyrosine, bypasses the requirement for cdc25 protein function (Gould, K. and P. Nurse, *Nature* 342:39–45 (1989)). Additional work has suggested that cdc25 is the cdc2 phosphatase. (Kumagai, A. and W. G. Dunphy, *Cell* 64:903–914 (1991); Strausfeld, U. et al., *Nature* 351:242–245 (1991)) and that cdc25 is the cdc2 phosphatase which dephosphorylates tyrosine and possibly threonine residues on $p34^{cdc2}$ and regulates MPF activation. (Dunphy, W. G. and A. Kumagai, *Cell* 67:189–196 (1991); Gautier, J. et al., *Cell* 67:197–211 (1991)).

The universal intracellular factor MPF triggers the G2/M transition of the cell cycle in all organisms. In late G2, it is present as an inactive complex of tyrosine-phosphorylated $p34^{cdc2}$ and unphosphorylated cyclin $B^{cdc13}$. In M phase, its activation as an active MPF displaying histone H1 kinase activity originates from the specific tyrosine dephosphorylation of the $p34^{cdc2}$ subunit by the tyrosine phosphatase $p80^{cdc25}$. Little is known about the signals which control or determine timing of MPF activation and entry into mitosis or about ways in which those signals can be blocked or enhanced, resulting in inhibition or facilitation of entry into mitosis.

Because the signals that control dephosphorylation of cdc2 on tyrosine and threonine play a key role in controlling timing of MPF activation and entry into mitosis, there is great interest in the proteins which control cdc2 dephosphorylation. Further knowledge of these proteins and their regulatory functions would be useful because it would provide a basis for a better understanding of cell division and, possibly, an approach to altering how it occurs.

SUMMARY OF THE INVENTION

For the first time, a key aspect of control of MPF activation and, thus, entry into mitosis, has been demonstrated. That is, B-type cyclins have been shown to activate cdc25 PTPase and a cdc25 protein has been shown to be able to stimulate directly the kinase activity of pre-MPF, resulting in activation of the M-phase kinase. As a result, it is now possible to design approaches to regulating entry into mitosis and, thus, regulate the cell cycle.

As described herein, Applicant has isolated two previously undescribed human cdc25 genes, designated cdc25 A and cdc25 B, and has established that human cdc25 is a multigene family, consisting of at least three members. As further described herein, cdc25 A and cdc25 B have been shown to have an endogenous tyrosine phosphatase activity that can be specifically activated by B-type cyclin, in the absence of cdc2. It has also been shown for the first time that cdc25 phosphatases and B-type cyclins interact directly and that cyclin B is a multifunctional class of proteins which serve, in addition to their recognized role as regulatory subunits for M-phase cdc2, a previously unknown and surprising role as activators of the cdc25 phosphatase. In addition, Applicant has shown that, in *Xenopus*, cdc25 levels do not change, either during meiotic maturation or early embryonic division cycles; that cdc25 physically associates with a cdc2/cyclin B complex in a cell cycle dependent manner; that the maximal association between cdc25 and the cdc2/cyclin B complex occurs just before or at the time of maximal kinase activity (of cdc2); and that the cdc2 associated with cdc25 is tyrosine dephosphorylated and active as a kinase. In addition, as a result of the work described herein, it is now evident that in *Xenopus*, cyclin is the only protein that must be synthesized during each round of activation and inactivation of MPF. It had previously been proposed that cyclin must accumulate to a critical threshold before pre-MPF is activated. However, it is reasonable, based on the work described herein, to suggest that this threshold marks the point at which sufficient cyclin B has accumulated to allow activation of the continuously present cdc25 phosphatase (which, in turn, stimulates kinase activity of pre-MPF).

As also described herein, a surprising observation has been made as a result of comparison of the amino acid sequences of newly discovered cdc25 A and cdc25 B gene products with known tyrosine protein phosphatases (PTPases) and other proteins involved in the cell cycle. That is, it has been shown that the region of cdc25 immediately C-terminal to the putative catalytic domain is not highly related to that of other known PTPases. Particularly interesting is the fact that this region within PTPases includes sequence similarity to cyclins, particularly B-type cyclins, and that cdc25 proteins have no equivalent "cyclin region". The newly found cyclin region is almost immediately adjacent to the domain implicated in the catalytic function of the PTPases and cdc25 protein. As a result of these findings, particularly the observation that cdc25 protein lacks a motif, shared by cyclin and other PTPases, that may be an activating domain, it is reasonable to suggest that in the case of cdc25, the activating domain is provided "in trans" by intermolecular interaction with cyclin.

As a result of the work described herein, new approaches to regulating the cell cycle in eukaryotic cells and, particularly, to regulating the activity of tyrosine specific phosphatases which play a key role in the cell cycle, are available. Applicant's invention relates to methods of regulating the cell cycle and, specifically, to regulating activation of cdc2-kinase, through alteration of the activity and/or levels of tyrosine phosphatases, particularly cdc25 phosphatase, and B-type cyclin, or through alteration of the interaction of components of MPF, particularly the association of cdc25 with cyclin, cdc2 or the cdc2/cyclin B complex. The present invention also relates to agents or compositions useful in the method of regulating (inhibiting or enhancing) the cell cycle. Such agents or compositions are, for example, inhibitors (such as low molecular weight peptides or compounds, either organic or inorganic) of the catalytic activity of tyrosine specific PTPases (particularly cdc25), blocking agents which interfere with the interaction or binding of the tyrosine specific PTPase with cyclin or the cyclin/cdc2 complex, or agents which interfere directly with the catalytic activity of the PTPases.

Applicant's invention also relates to cdc25 A, cdc25 B and additional members of the cdc25 multigene family and to methods and reagents (e.g., nucleic acid probes, antibodies) useful for identifying other members of the cdc25 family, particularly those of mammalian (e.g., human) origin.

Applicant's invention also includes a method of identifying compounds or molecules which alter (enhance or inhibit) stimulation of kinase activity of pre-MPF and, thus, alter (enhance or inhibit) activation of MPF and entry into mitosis. The present method thus makes it possible to identify agents which can be administered to regulate the cell cycle; such agents are also the subject of this invention.

The present method makes use of a cell cycle-specific target and, thus, provides a highly specific mechanism-based screen for agents (compounds or molecules) which alter mitosis, particularly antimitotic agents. In the subject method, an agent is assessed for its effect on the essential cell cycle-regulating component, cdc25 (e.g., cdc25A, cdc25B, cdc25C).

In particular, the agent to be assessed for its ability to inhibit cdc25 tyrosine phosphatase activity is combined with cdc25 and a substrate of cdc25 tyrosine phosphatase activity. The resulting combination is maintained under conditions appropriate for cdc25 to act upon the substrate. It is then determined whether cdc25 acted upon the substrate when the compound being assessed was present; the extent to which cdc25 acts upon the substrate in the presence of the compound is compared with the extent to which cdc25 acts on the substrate in the absence of the compound (in comparison with a control). If cdc25 activity is less in the presence of the compound, the compound is an inhibitor of cdc25.

More particularly, a potential antimitotic agent (i.e., an agent to be assessed for an antimitotic effect) is combined with cdc25, which is either cdc25 protein or a fusion protein (e.g., recombinant $p80^{cdc25}$ present in a two-component fusion protein in which cdc25 is joined with a second component, such as glutathione-S-transferase). Subsequently, the effect of the potential antimitotic agent on the phosphatase activity of cdc25 is determined. $p80^{cdc25}$ protein has been shown, as described herein, to have p-nitrophenylphosphate phosphatase activity. Thus, the inhibitory effect of the agent being tested on cdc25 can be assessed using p-nitrophenylphosphate or inactive cyclin/cdc2 as substrate. Results obtained (e.g., the extent of inhibition of cdc25 phosphatase activity) are particularly valuable, since they demonstrate the effect of the agent tested on a target which is particularly well suited for detecting antimitotic agents because of its direct role in controlling entry of cells into M phase.

BRIEF DESCRIPTION OF THE FIGURES

FIGS. 1A–F are the nucleotide sequence of cdc25 A and the nucleotide sequence of cdc25 B. Panel A, sequence of cdc25 A cDNA (SEQ ID NO. 1). Panel B, sequence of cdc25 B (SEQ ID NO. 3). Below the nucleotide sequence is the translation in standard single letter amino acid code. In each sequence, the presumed initiating methionine is underlined. An in-frame stop codon upstream of the initiating AUG codon in the cdc25 A sequence is in bold and in each sequence, the terminating codon is marked by an asterisk.

FIG. 2 shows the homology of cdc25 proteins. The amino acid sequences of cdc25 A and cdc25 B were aligned with human cdc25 C (formerly CDC25Hs), string (Stg) and *S. pombe* cdc25 (25Sp) using the FASTA program. Identical amino acids are boxed. In cases of only two alternative amino acids at a particular site a box is also used. Dashes within the sequences indicate individual amino acid gaps created by the computer to generate optimal alignment.

FIG. 3A is a graphic representation of the mitotic index of a population of the HeLa cells microinjected at time zero with the affinity-purified anti-cdc25A antibodies. Control cells were microinjected with the IgG fraction of the preimmune serum. FIG. 3B is a graphic representation of the estimation of cell numbers in islands of HeLa cells injected at time zero with control or experimental anticdc25A affinity purified antibodies.

DETAILED DESCRIPTION OF THE INVENTION

Figure 3A:
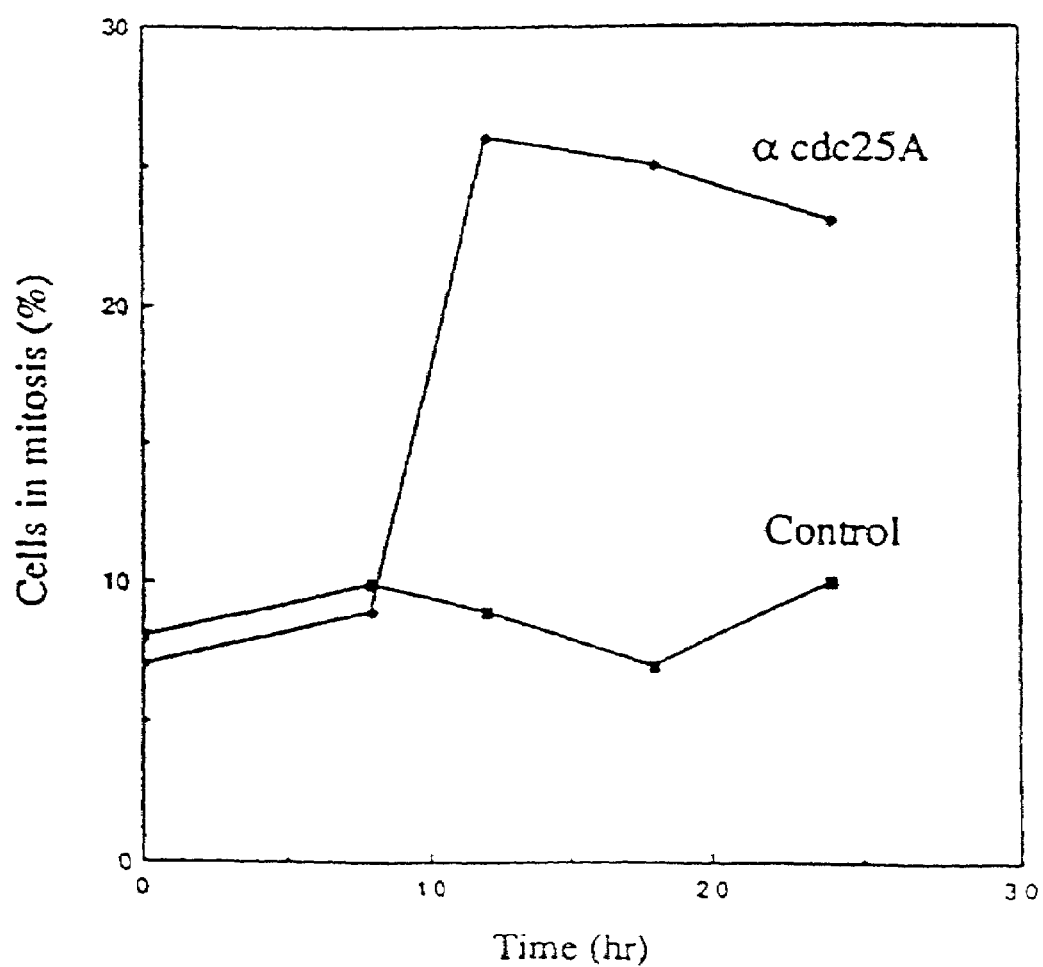
FIGS. 3A–B provide proof that human cdc25 A is essential for mitosis.

The present invention relates to a method of regulating (inhibiting or enhancing) cell division and to agents or compositions useful for regulating the cell cycle. It further relates to two human genes, referred to as cdc25 A and cdc25 B, encoding tyrosine-specific phosphatases, the encoded tyrosine-specific phosphatases and additional members of the cdc25 multigene family, particularly additional human cdc25 genes, and their encoded products. In addition, the invention relates to a method of identifying agents which alter stimulation of kinase activity and thus alter entry of the cell into mitosis. The present invention also relates to an assay in which cdc25 tyrosine phosphatase, such as cdc25 protein or recombinant human cdc25 tyrosine phosphatase, is used as a cell cycle-specific target to screen for compounds which alter entry into mitosis (passage from late G2 into the M phase). Applicant's invention is based on identification of new cdc25 genes and the discovery that cdc25 proteins interact directly with and are specifically activated by B-type cyclins and activate cdc2 kinase.

Applicant has isolated two human cdc25 genes, designated cdc25 A and cdc25 B, and has thus established that human cdc25 is a multigene family of at least three members. The three human cdc25 proteins (cdc25 A, cdc25 B and the previously identified cdc25 protein) have been shown to have approximately 40% identity in the most conserved C-terminal region. The cdc25 A and cdc25 B proteins can be classified as cdc25 proteins by a variety of independent criteria.

As shown herein, the cdc25 A gene product and cdc25 B gene product have endogenous tyrosine phosphatase activity in vitro which is stimulated several-fold, in the absence of cdc2, by cyclin B1 or cyclin B2. As is also shown herein, stable association occurs between cdc25 A and cyclin B1/cdc2 in human cells, specifically HeLa cells. These findings indicate that B-type cyclins are multi-functional proteins which not only are M-phase regulatory subunits, but also activate the cdc25 tyrosine phosphatase which, in turn, acts upon cdc2.

Figure 2:
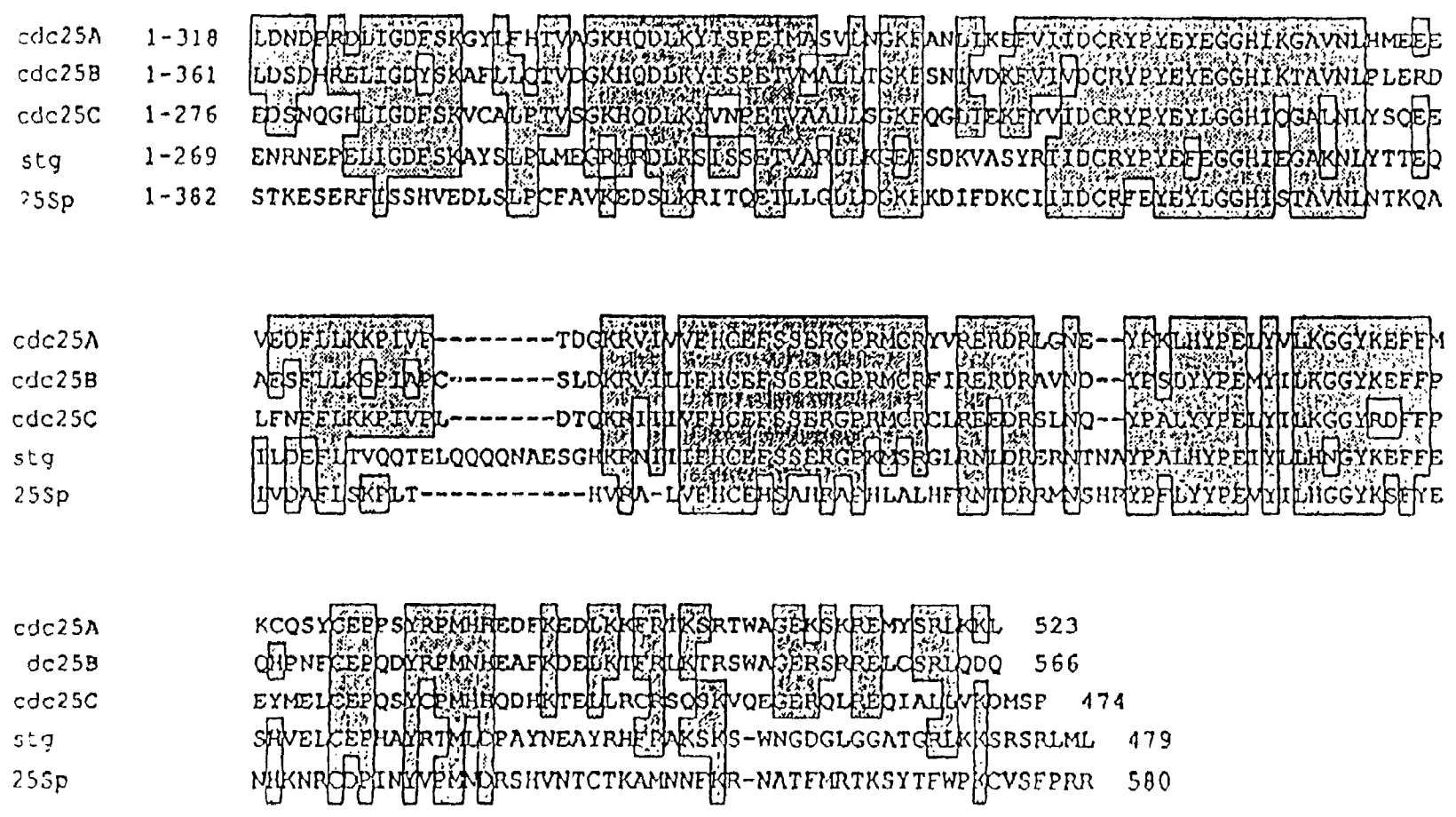

A region of amino acid similarity between cyclins and cytoplasmic tyrosine phosphatases has been identified and shown not to be present in cdc25 phosphatases, suggesting that the common motif represents an activating domain which must be provided to cdc25 by cdc25-cyclin B intramolecular interaction. Specifically, visual comparison of cdc25 A and cdc25 B with known tyrosine phosphatases (PTPases) and other proteins involved in cell cycle control resulted in the unexpected observation that a region of cdc25 immediately C-terminal to the putative cdc25 catalytic domain is not highly related to other known PTPases and that this newly found motif within the PTPases includes sequence similarity to cyclins, particularly of the B-type. Alignment of amino acid sequences of the cdc25 homologs and a diverse group of protein tyrosine phosphatases (PTPs) demonstrated that a C-terminal fragment of approximately 200 amino acid residues is a conserved protein motif which resembles the proposed catalytic center of viral and mammalian PTPases (see Example 1 and FIG. 2).

Applicant has shown that the two new human cdc25 genes encode proteins functionally related to that encoded by the fission yeast cdc25 (Example 2). One of the human cdc25 genes (cdc25 A) has been shown to act in mitosis in human cells, which arrest in a "rounded up" mitotic state after microinjection of anti-cdc25 A antibodies. Thus, Applicant has shown for the first time that the PTPase is necessary for cell division, Applicant has also shown that cell division is inhibited by anti-cdc25 A antibodies, which are, thus, a cytotoxic agent.

Surprisingly, it has also been shown that the endogenous phosphatase activity of cdc25 A and cdc25 B proteins purified from *E. coli* is directly activated by stoichiometric addition of B-type cyclin, in the absence of cdc2 (Examples 4 and 5), thus showing that B-type cyclins have a multifunctional role in this stage of cell division. This clearly demonstrates specificity between cyclins in their role as activators of cdc25. Until this finding, it has proved difficult to demonstrate differences in substrate specificity among members of the cdc2/cyclin family, although a variety of lines of evidence have suggested that cyclins of different classes have specific roles at particular stages of cell division. The cdc25 A protein has been shown to be present in a complex with both cyclin B1 and cdc2 (Example 5).

Applicant has also determined that *Xenopus* oocytes contain a relative of cdc25, designated p72, which can directly stimulate the M-phase kinase in vitro and is essential for activation of the M-phase kinase in cell-free lysates. As described herein, the abundance of p72 does not change in *Xenopus* embryos during the cell cycle. p72 has been shown to directly associate with cdc2/cyclin B in a cell cycle dependent manner, reaching a peak at M-phase. The M-phase kinase which associates with p72 has been shown to be tyrosine dephosphorylated and catalytically active. As a result, it is reasonable to conclude that cdc25 triggers cdc2 activation by a mechanism which involves periodic physical association between cdc25 and the cyclin B/cdc2 complex, and that it is the association between cdc2/cyclin B and cdc25 which is required. It is also reasonable to conclude that mitotic control can be effected by mechanisms other than transcriptional regulation of the cdc25 gene.

As a result of Applicant's findings concerning the role of cdc25 in cell division, an assay is now available in which cdc25 is used as a cell-cycle specific target to screen for compounds which alter a cell's entry into the mitosis phase of cell growth. Results of the assay (i.e., the ability of the compound being tested to inhibit cdc25) are determined by known techniques, such as colormetrically, by immunoassay techniques or by detecting enzymatic activity (e.g., histone kinase activity).

The following describes Applicant's isolation and characterization of two new human cdc25 genes; demonstration of the multifunctional role of B-type cyclin in mitosis; the unexpected observation of a common amino acid sequence or motif present in PTPases and cyclins but absent in cdc25, and the determination that the motif resembles the proposed catalytic center of viral and mammalian PTPs; demonstration of a specific interaction between cdc25 phosphatases and B-type cyclins; and demonstration that the level of cdc25 in *Xenopus* oocytes does not change during the cell cycle. As a result of the work described, novel methods and compositions for cell cycle regulation are available, as well as an assay for compounds which alter cell cycle regulation. These methods, compositions, and assay are also described below.

Isolation and Characterization of Two New Human cdc25 Genes Which Are Members of a Multigene Family Two new human cdc25 genes have been isolated, establishing the fact that in humans, cdc25 is a multigene family that consists of at least three members. The three human cdc25 proteins share approximately 40% identity in the most conserved C-terminal region. The two newly discovered cdc25 genes, cdc25 A and cdc25 B, can be classified as cdc25 proteins by a variety of quite independent criteria. First, they share sequence similarity with other members of the family. Second, cdc25 A and cdc25 B can each rescue a mutant cdc25-22 strain of fission yeast. Third, injection of antibodies prepared against a peptide comprising part of the cdc25 A protein into proliferating HeLa cells causes their arrest in mitosis. Fourth, cdc25 A protein eluted from immunocomplexes can activate the latent histone kinase activity of cdc2. Fifth, both cdc25 A and cdc25 B purified from *E. coli* display an endogenous tyrosine phosphatase activity.

The cdc25 Multigene Family

As described, it has now been shown that in humans, there are at least three cdc25 genes and possibly more. In fission yeast, only one essential cdc25 gent has been identified to date (Russell, P. and P. Nurse, *Cell* 45:145–153 (1986)). Likewise, a single essential mitotic B-type cyclin has been described in this yeast (Booher, R. and D. Beach, *EMBO J.* 7:2321–2327 (1988)). Two mitotic B-type cyclins have been found both in frog and humans (Minshull, J. et al., *Cell* 56:947–956 (1989)). Presumably, there is some differentiation of function between different members of the cdc25 and B-type cyclin families in vivo. Genetic studies in budding yeast, in which multiple B-type cyclins have been found, give some general hint that this is the case (Surana, U. et al., *Cell* 65:145–161 (1991); Ghiara, J. B. et al., *Cell* 65:163–174 (1991)). However, both cyclin B1 and B2 could activate cdc25 A in vitro. One might postulate that different human cdc25 genes activate different cyclin B/cdc2 complexes in vivo and this may explain why injection of anti-cdc25 A serum into HeLa cells causes arrest in mid-mitosis, rather than in interphase.

It should be noted that regulation of cdc2 by tyrosine phosphorylation has currently only been described with respect to the cdc2/cyclin B enzyme. However, in certain contexts, it has been possible to substitute cyclin B with cyclin A (Swenson, K. I., et al., *Cell* 47:861–870 (1986)); Pines, J. and T. Hunt, *EMBO J.* 6:2987–2995 (1987)), and indeed human cyclin B2 was isolated by virtue of its ability to rescue a cn-deficient strain of budding yeast (Xiong, Y. et al., *Cell* 65:691–699 (1991)). In the work described herein, cyclin A could not activate cdc25 A or cdc25 B (not shown). This does not preclude, however, the existence of undiscovered cdc25-related phosphatases, that might be specifically activated by cyclin A. It is also presently unknown whether relatives of cdc2, such as cdk2 (formerly egl, Paris, J. et al., *Proc. Natl. Acad. Sci. USA* 88:1039–1043 (1991); Elledge, S. J. and M. R. Scottswood, *EMBO J.* 10:2653–2659 (1991)), that can bind cyclin A (Tsai, L -H. et al., *Nature* 353:174–177 (1991)), are subject to regulation by tyrosine phosphorylation and, hence, might require a cdc25 relative for activation.

Multifuncitonal Role Of B-Type Cyclin In Mitosis

A particularly striking observation described herein is the demonstration that the endogenous phosphatase activity of cdc25 A and cdc25 B proteins purified from *E. coli* can be directly activated by stoichiometric addition of B type cyclins. Specificity of this effect is shown by the inability of either cyclin A or cyclin D1 to display any such stimulation. A variety of lines of evidence suggest that cyclins of different classes have specific roles at particular stages of the division cycle (Booher, R. and D. Beach, *EMBO J.* 6:3441–3447 (1987); Booher, R. and D. Beach, EMBO J. 7:2321–2327 (1988); Nash, R. et al., *EMBO J.* 7:4335–4346 (1988); Hadwiger, J. A. et al., *Proc. Natl. Acad. Sci. USA* 86:6255–6259 (1989); Richardson, H. E. et al., *Cell*

59:1127–1133 (1989); Cross, F., *Mol. Cell. Biol.* 8:4675–4684 (1980); Wittenberg, C. et al., *Cell* 61:225–237 (1990); Draetta, G. et al., *Cell* 56:829–838 (1989); Giordano, A. et al., *Cell* 58:981–990 (1989); Pines, J. and T. Hunter, *Nature* 346:760–763 (1990); Xiong, Y. et al., *Cell* 65:691–699 (1991); Lew, D. J. et al., *Cell* 66:1–10 (1991); Koff, A. et al., *Cell* 88:1–20 (1991)). However, it has proved difficult to demonstrate differences in substrate specificity between members of the cdc2/cyclin family in vitro, and all known cyclins can rescue a CLN-deficient strain of budding yeast. The present experiments vividly demonstrate specificity between different cyclins in their role as activators of cdc25.

Certain evidence, both genetic and biochemical, suggests that cdc2 is a physiological substrate of cdc25 phosphatases (Gould, K. and P. Nurse, *Nature* 342:39–45 (1989); Kumagai, A. and W. G. Dunphy, *Cell* 64:903–914 (1991); Strausfeld, U. et al., *Nature* 351:242–245 (1991); Gautier, J. et al., *Cell* 67:197–211 (1991)). cdc2 was not used as a substrate in the present study because it binds to cyclins and, thus, potentially becomes altered as a phosphatase substrate; therefore, the issue of cdc25 substrate specificity has not been addressed directly. However, the finding of activation of cdc25, specifically by B-type cyclins, strengthens the conclusion that cdc2/cyclin B is the relevant substrate in vivo. Demonstration of activation of cdc25 when artificial PTPase substrates were used leads to the conclusion that cyclins are able to interact with cdc25 in the total absence of cdc2 protein. In vivo, it is expected that this interaction occurs in the context of the cdc2/cyclin B pre-MPF complex. The above-described work demonstrates that B-type cyclins have at least two roles. First, they bind stoichiometrically with cdc2 to regulate the substrate specificity (Draetta, G. et al., *Nature* 336:738–744 (1989); Brizuela, L. et al., *Proc. Natl. Acad. Sci. USA* 86:4362–4366 (1989)) and the intracellular localization of the catalytic subunit (Booher, R. N. et al., *Cell* 58:485–497 (1989)). Second, they appear to have an independent function: the activation of cdc25 PTPase.

Genetic studies in fission yeast and *Drosophila* indicate that cdc25 is a dose-dependent activator of mitosis (Russell, P. and P. Nurse, *Cell* 45:145–153 (1986); Edgar, B. A. and P. H. O'Farrell, *Cell* 57:177–187 (1989)), whereas the cdc13 encoded B-type cyclin is essential for M-phase, but does not serve as a dose-dependent activator. Indeed, in many cell types, including the fission yeast, B-type cyclins accumulate and associate with cdc2 long before the tyrosine dephosphorylation event at the onset of M-phase (Booher, R. N. et al., *Cell* 58:485–497 (1989)). In some somatic cell types, the cdc25 gene is under transcriptional control, and very probably the cdc25 protein itself is regulated in a variety of ways that are not presently understood. In the early embryos of *Xenopus*, a somewhat different situation holds. As shown herein, the abundance of cdc25 is invariant during the cell cycle. Cyclin is the only protein that has to be synthesized during each round of activation and inactivation of MPF (Murray, W. W. et al., *Nature* 339:280–286 (1989)). It has been proposed that, in this context, cyclin must accumulate to a critical threshold before pre-MPF is activated (Evans, T. et al., *Cell* 33:389–396 (1983); Pines, J. and T. Hunt, *EMBO J.* 6:2987–2995 (1987); Minshull, J. et al., *Cell* 56:947–956 (1989); Murray, A. W. and M. W. Kirshner, *Nature* 339: 280–286 (1989)). Based on work described herein, it appears that this threshold marks the point at which sufficient cyclin has accumulated to allow activation of the continuously present cdc25 phosphatase.

The present findings may throw light on the long obscure phenomenon of MPF autoactivation. If a small amount of MPF is injected into a frog oocyte, a much larger amount can subsequently be retrieved (Masui, Y. and C. L. Markert, *J. Exp. Zool.* 171:129–146 (1971); Smith, L. D. and R. E. Ecker, *Dev. Biol.* 25:232–247 (1971)). The present work shows that in this situation, the abundance of cdc2, cyclin B and cdc25 do not change (Gautier, J. and J. Mailer, *EMBO J.* 10:177–182 (1991); see also Example 11). It has been implicitly assumed that active cdc2/cyclin B phosphorylates some protein (possibly cdc25 itself), causing the activation of cdc25 and, thus leading to further activation of pre-MPF. This may be correct, but if cyclin B directly activates cdc25 in the absence of cdc2, as shown herein, all of the elements needed for an autoactivation loop exist among the cdc2, cyclin B and cdc25 proteins themselves.

A Common Motif in PTPases and Cyclins

Figure 7A:
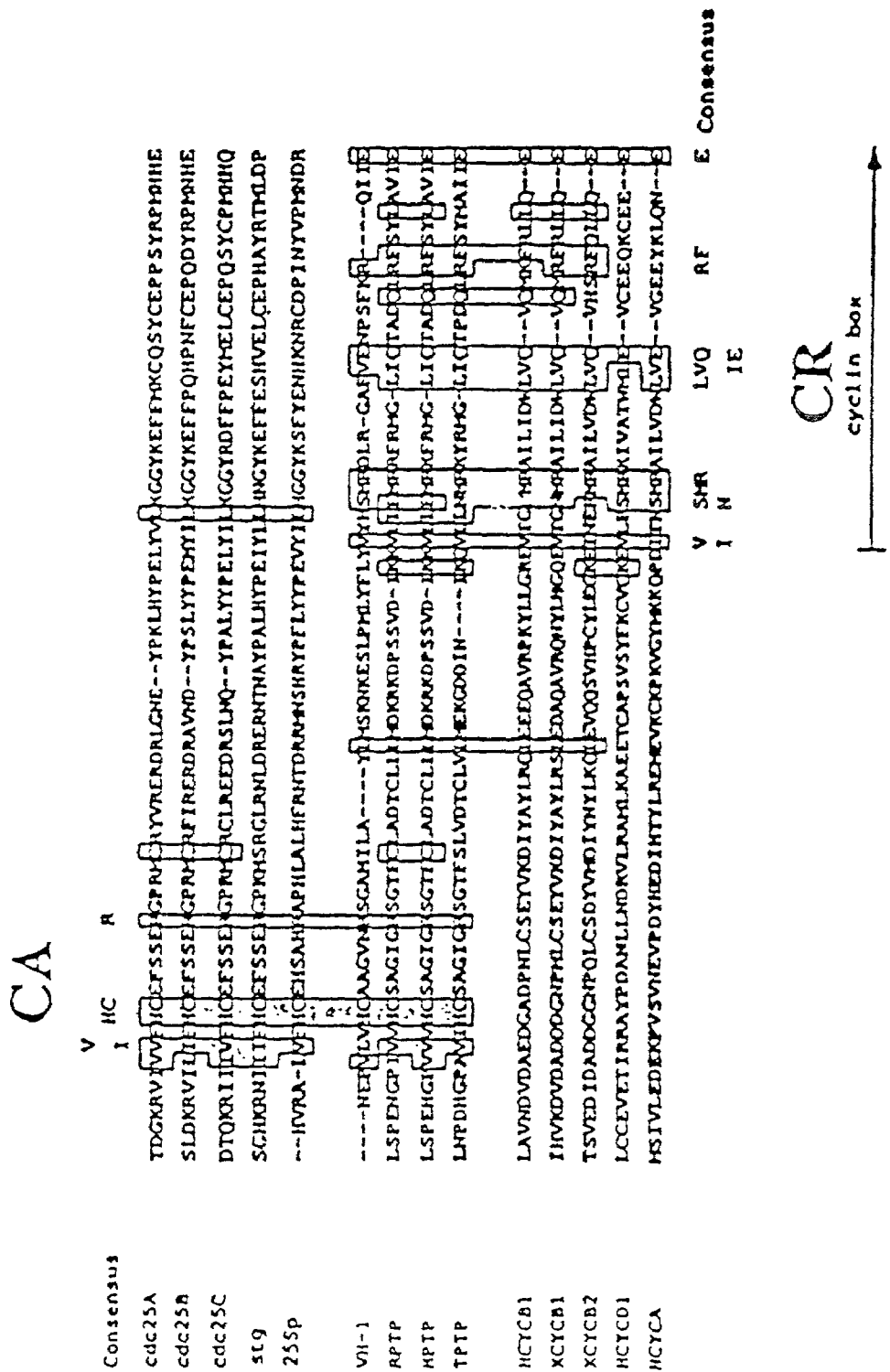
FIGS. 7A–B show the alignment of the cdc25 proteins, PTPases and cyclins and a model of a proposed relationship between PTPases and the M-phase kinase and cdc25 phosphatase. Panel A depicts the alignment, in which CA indicates the puative catalytic domain of the cdc25 and cytoplasmic tyrosine phosphatases, and CR indicates the cyclin related domain, present in tyrosine phosphatases but absent in cdc25 proteins. Panel B depicts a schematic representation of the hypothetical relationship between PTPases, and the M-phase kinase and cdc25 phosphatase.

Alignment of the cdc25 proteins, PTPases and cyclins was performed, as shown in FIG. 7A. Tyrosine phosphatases were aligned with each other as described in Guan, K. et al., (*Nature* 350:359–362 (1991)) and cdc25 proteins as described in Gautier, J. et al., (*Cell* 67:197–211 (1991)). The cyclin alignment was done by visual inspection. Only identity or similarity (V or I) within at least three members of one gene family and a minimal of two members of other family is boxed. Visual comparison of cdc25 A and B with known tyrosine PTPases, and also other proteins involved in cell cycle control, resulted in the following unexpected observations. First, the region of cdc25 that is immediately C-terminal to the putative catalytic domain (CA) is not highly related to other known PTPases, such as cytoplasmic PTPases from higher eukaryotes and the vaccinia virus serine-tyrosine phosphatase (VH-I, Guan, et al., *Nature* 350:359–362 (1991); FIG. 7A). Second and more interestingly, this region within the PTPases was found to contain sequence similarity to cyclins, particularly of the B-type (FIG. 7A). The similarity was detected immediately at the junction of the so-called cyclin-box and included some nearly invariable residues among cyclins. The alignment in FIG. 7A optimizes the similarities between cdc25 proteins and PTPases, and also between PTPases and cyclins, but ignores the much greater homology within each of the three groups of proteins. In the region of similarity between PTPases and cyclins, referred to as the cyclin region (CR), there is no equivalent in the cdc25 proteins.

The newly found motif lies almost immediately adjacent to the domain (V/IXHCXXXXR), that has been directly implicated in the catalytic function of the PTPases and cdc25 protein (Krueger, N. S. et al., *EMBO J.* 9:3241–3252 (1990); Guan, K. and J. E. Dixon, *Science* 249:553–556 (1990); Guan, K. et al., *Anal. Biochemistry* 192:262–267 (1991); Gautier, J. et al., *Cell* 67:197–211 (1991)). This finding allows the following speculation. The catalytic activity of the other PTPases is considerably greater than that of cdc25, at least as determined in this study. cdc25 lacks the motif that is shared by cyclins and other PTPases. This motif may be an activating domain which, in the case of cdc25, is provided in "trans" by intermolecular interaction with cyclin (FIG. 7B), although in most PTPases it functions in "cis".

There is some similarity between PTPases and all of the classes of cyclin, whereas only B-type cyclins can activate cdc25. It is apparent, however, that the similarity is greatest between PTPases and cyclins of the B class. The differences between the various classes of cyclins within this region might be related to the specific ability of B but not A or D-type cyclins to activate cdc25 A.

Specific Interaction of cdc25 with Cyclin B

As shown in Example 13, cdc25 stably associates with a cdc2 complex and this interaction is periodic during the division cycle of Xenopus embryos. Human cyclin B1 is found in the complex with cdc25 A, as described in Example 5. It seems likely that the periodicity of the interaction between cdc25 and cdc2 is mediated at least in part by periodic accumulation and degradation of cyclin during the cell cycle.

As described herein, it has been established that cdc25 can function as an enzyme with respect to RCML, PNPP and cdc2 derived peptide substrates. A low observed catalytic rate was evident and may reflect the use of RCML or peptide as an artificial substrate. However, it is not clear what catalytic rate is required in vivo. If cdc25 does indeed associate with cdc2/cyclin B as suggested herein (Example 9 and FIG. 7), the PTPase may not function in a conventional catalytic reaction, but rather only after formation of a cdc25/cyclin B/cdc2 complex. Under such conditions, the catalytic reaction is essentially intramolecular and Michaelis/Menten kinetics do not pertain.

Inhibition by P13 of Human cdc25 Phosphatase Activity

The p13 protein encoded by the suc1 gene is an essential subunit of the cdc2 protein kinase. The gene was isolated by virtue of its ability to rescue a fission yeast cdc2-33 allele on a multicopy plasmid (Hayles, J. et al., *EMBO J.* 5:3373–3379 (1986)). However, overexpression of the gene is inhibitory for mitosis (Hindley, J. et al., *Mol. Cell. Biol.* 7:504–511 (1987); Hayles, J. et al., *Mol Gen. Genet.* 202: 291–293 (1986)). In vitro, p13 can inhibit activation of pre-MPF (Dunphy, W. et al., *Cell* 54:423–431 (1988); Dunphy, W. and J. W. Newport, *Cell* 58:181–431 (1989)).

Figure 7B:
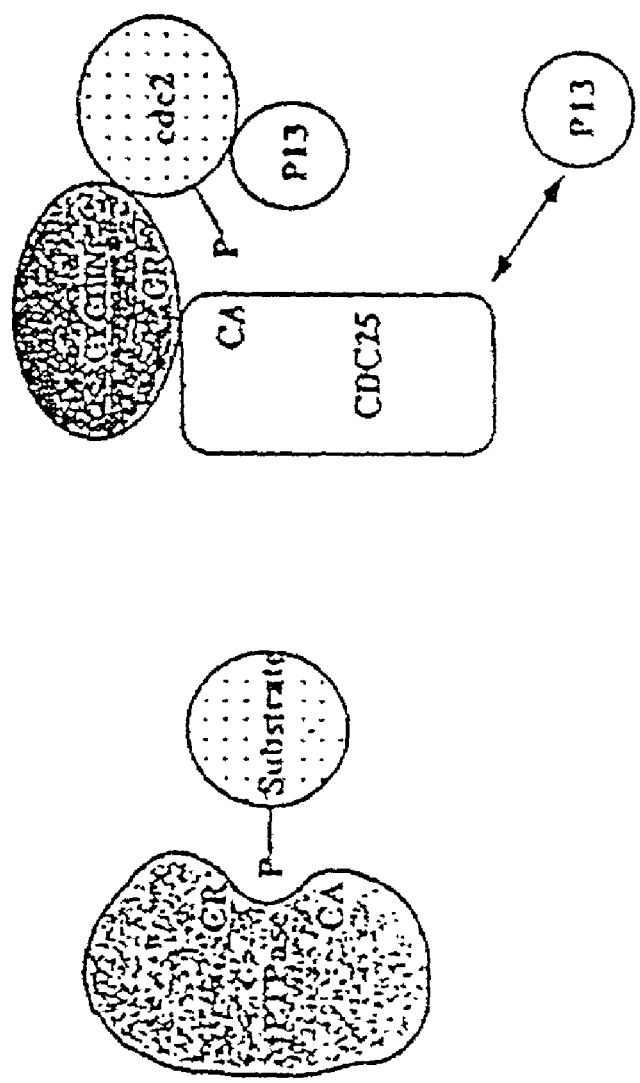

The present work may clarify two previously confusing issues related to these observations. First, p13 can bind to cdc2 in the absence of cyclins (Brizuela, L. et al., *EMBO J.* 6:3507–3514 (1987); see also Example 6), but activation of cdc2/cyclin B that is pre-bound to p13-sepharose can be inhibited by excess exogenous p13 (Jessus, C. et al., *FEBS LETTERS* 266:4–8 (1990)). By contrast, fully activated cyclin B/cdc2 is not inhibited by excess p13 (Dunphy, W. et al., *Cell* 54:423–431 (1988); Arion, D. et al., *Cell* 55:371–378 (1988); Maijer, L. et al., *EMBO J.* 8:2275–2282 (1989)). This suggests, as previously proposed (Jessus, C. et al., *FEBS LETTERS* 266:4–8 (1990)), that there are at least two binding sites for p13. One is presumably a high affinity binding site on cdc2 itself, that accounts for the extraordinary efficiency of p13-sepharose chromatography. The other site, of lower affinity requiring p13 in the 20 micromolar range, does not affect fully activated cdc2/cyclin B, but can inhibit activation of pre-MPF. Because direct inhibition of cdc25 A endogenous phosphatase activity by p13, in the total absence of cdc2, has been observed (Example 6), it is reasonable to attribute the second binding site not to cdc2, but to cdc25. This is probably an unstable interaction, quite unlike that between p13 and cdc2. A schematic representation of the hypothetical relationship between PTPases, the M-phase kinase and cdc25 phosphatase, is shown in FIG. 7B. The association between cdc2 and p13, and between cyclin and cdc2, is well documented. The interaction of cdc25 and cyclin is also proposed here, p13 is proposed to have a low affinity interaction with cdc25. CA is the catalytic domain of PTPases and CR is a region of similarity between PTPases and cyclins.

Second, there has been some dispute concerning the inhibition of cdc25 by p13 in different experimental contexts. In some cases, p13 has been inhibitory (Gautier, J. et al., *Cell* 67:197–211 (1991)) and in other cases, it has not (Kumagai, A. and W. G. Dunphy, *Cell* 64:903–914 (1991)). As described herein under the conditions used, cdc25 A is inhibited by p13, and cdc25 B is not. The two proteins have many regions of structural dissimilarity that could readily account for this effect.

cdc25 Does Not Change in Abundance During the Cell Cycle

Surprisingly, the Xenopus cdc25 does not oscillate in abundance, either during meiotic maturation, or during the early embryonic division cycles. The protein does, however, physically associate with the cdc2/cyclin B complex in a cell cycle dependent manner (see Examples 5 and 10). Maximal association is found just before or at the time of maximal kinase activity (see Examples 11 and 13, and FIG. 9). The cdc2 that is associated with cdc25 is tyrosine dephosphorylated and active as a histone H2 kinase. The association between cdc25 and the cdc2/cyclin B complex could be mediated either by cdc2 or by cyclin B. As described herein, B-type cyclins were shown to be able to directly activate the intrinsic PTPase activity of cdc25 proteins in the absence of cdc2. This suggests that the interaction between cdc25 and the cdc2/cyclin B complex is probably mediated by cyclin.

These results bear upon the mechanism by which cdc2 becomes activated at M-phase. cdc25 acts in mitosis to cause the tyrosine dephosphorylation of cdc2, as described herein. The demonstration of direct physical association between cdc25 and the cdc2/cyclin B complex is entirely consistent with this hypothesis. The finding that approximately 5% of cdc2 associates with cdc25 at M-phase raises certain questions. It is possible that one molecule of cdc25 binds to cdc2/cyclin B, activates the kinase and then dissociates to repeat the process in a conventional catalytic mechanism. Alternatively, a single molecule of cdc25 might activate only a single molecule of pre-MPF in a stoichiometric mechanism. only a fraction of the total amount of cdc2 (10% of the cellular cdc2 content, as described in Kobayashi A. H. et al., *J. Cell Biol.* 114:755–765 (1991)) is bound to cyclin B and activated at M-phase in *Xenopus* eggs. The finding that only 5% of total cdc2 is associated with cdc25 at mitosis might reflect the relatively low abundance of cyclin B compared to cdc2, if the interaction is mediated by cyclin B. This is confirmed by the fact that, in comparison to the 5% cdc25-associated cdc2, a larger amount of cyclin B2 is found in association with cdc25 (17% of the full cellular amount of cyclin B2). Moreover, a considerable fraction of cdc25 is involved in this association (20% of the cellular content).

Identification of Additional cdc25 Genes and Cell Cycle Regulation by the Present Invention Using methods described herein, such as in Examples 1 and 7, additional members of the human cdc25 gene family and cdc25 genes in other organisms can be identified and isolated; the encoded products can be identified as well. For example, all or a portion of the nucleotide sequence of the cdc25 A gene or the cdc25 B gene (see FIG. 1) can be used in hybridization methods or amplification methods known to those of skill in the art (Sambrook, et al., *Molecular Cloning: A Laboratory Manual*, Cold Spring Harbor Laboratory, NY (1989)). For example, a nucleotide sequence which is all or a portion of the cdc25 A gene or the cdc25 B gene can be used to screen a DNA library of human or nonhuman origin for additional cdc25 genes. DNA sequences identified in this manner can be expressed and their products analyzed for tyrosine specific phosphatase activity, such as by the methods described herein (see Experimental Procedures and Example 2). Hybridization conditions can be varied as desired. If a nucleotide sequence which is exactly complementary to the probe used is to be isolated, conditions of either high or low stringency can be used; if a nucleic acid sequence less related to those of the probe is to be identified, conditions of lower stringency are used. The present invention includes the cdc25 A and cdc25 B genes and equivalent cdc genes; equivalent genes, as used herein, are nucleic acid sequences which hybridize to all or a portion of the cdc25 A or cdc25 B gene or a complement of either gene, and encode a tyrosine PTPase which has substantially the same catalytic function as the cdc25 A or cdc25 B gene product. The polymerase chain reaction and appropriately designed primers can also be used to identify other cdc25 genes. Alternatively, an anti-cdc25 A or anti-cdc25 B antibody can be used to detect other (recombinant) cdc25 gene products expressed in appropriate host cells transformed with a vector or DNA construct thought to encode a cdc25 product. The cdc25 A gene, cdc25 B gene and equivalent cdc genes which are the subject of the present invention include those obtained from naturally occurring sources and those produced by genetic engineering (cloning) methods or by synthetic methods. These genes can be used to produce the encoded cdc25 A, cdc25 B or other cdc25 gene product, which can, in turn, be used to produce antibodies specific for the product or to regulate cell cycle activation (cdc2 kinase activation), as described below.

The present invention also includes PTPase genes which encode PTPases which are related to cdc25 PTPases but are specifically activated by a non-B type cyclin (e.g., by cyclin A, cyclin D). These PTPases are referred to herein as cdc25-related PTPases and their activation by a cyclin, their ability to activate cdc2 or another molecule and their role in regulation of the cell cycle can be assessed using the methods described for determining the role of cdc25.

The present invention also provides a method by which the level of expression or activity of cdc25 PTPases in a cell can be determined and assessed (i.e., to determine if they increased, decreased or remained within normal limits). Because the cdc25 gene is increased (overexpressed) in certain tumor types, the present invention also provides a method of diagnosing or detecting overexpression related to those tumor cell types. In the method, a gene probe to detect and quantify the cdc25 gene in cells, or antibodies specific for the cdc25 PTPase can be used.

Assay for Compounds Which Alter cdc25 Function/Entry into Mitosis

A method of inhibiting activation of cdc25 PTPases, activation of cdc2 kinase(s) and, thus, initiation of mitosis (cell division) is also possible. For example, activation of cdc25 PTPase is inhibited (reduced or prevented) by introducing into cells a drug or other agent which can block, directly or indirectly, complexing of cdc25 with cyclin B or the cyclin B/cdc2 complex and, thus, directly block activation of the cdc25 and indirectly block activation of the cdc2 kinase. In one embodiment, complex formation is prevented in an indirect manner, such as by preventing transcription and/or translation of the cdc25 DNA and/or RNA. This can be carried out by introducing into cells antisense oligonucleotides which hybridize to the cdc25-encoding nucleic acid sequences, and thus prevent their further processing. It is also possible to inhibit expression of the cdc25 product by interfering with an essential cdc25 transcription factor. Alternatively, complex formation can be prevented by degrading the cdc25 gene product(s), such as by introducing a protease or substance which enhances their breakdown into cells. In either case, the effect is indirect in that a reduced quantity of cdc25 is available than would otherwise be the case. In another embodiment, activation of cdc25 PTPase is inhibited by interfering with the newly identified region of cyclin which has been shown to share sequence similarity with a region present in other PTPases, but not present in cdc25, and which appears to be provided to cdc25 in trans by intermolecular interaction with cyclin.

In another embodiment, activation of cdc25 PTPase is inhibited in a more direct manner by, for example, introducing into cells a drug or other agent which binds the PTPase and prevents complex formation with cyclin (and, thus, prevents PTPase activation). Alternatively, a drug or other agent which interferes in another manner with the physical association between cyclin and the PTPase (e.g., by intercalation), or which disrupts the catalytic activity of the enzyme can be introduced into cells. This can be effected, for example, by use of antibodies which bind the PTPase or the cyclin, or by a peptide or low molecular weight organic or inorganic compound which, like the endogenous type B cyclin binds the cdc25 PTPase, but, unlike type B cyclin does not result in activation of the enzyme or results in its being disabled or degraded. Peptides and small organic compounds to be used for this purpose can be based on analysis of the amino acid sequences of B type cyclins or of the amino acid sequences of the cdc PTPase(s) involved. They can be designed, for example, to include residues necessary for binding and to exclude residues whose presence results in activation. This can be done, for example, by systematically mapping the binding site(s) and designing molecules which recognize or otherwise associate with the site(s) necessary for activation, but do not cause activation. One site of particular interest for this purpose is the region which, as described above, is missing in cdc25 PTPases and appears to be provided in trans by intermolecular binding of the cdc25 product and type B cyclin. At least three possible approaches are possible in this instance. First, a molecule (e.g., a peptide which mimics the binding site on type B cyclin for cdc25) can be introduced into cells; the molecule then binds cdc25 and blocks its interaction with cyclin. Second, a molecule mimicking the region of cdc25 which binds the type B cyclin molecule can be introduced into cells; the molecule then binds cyclin and blocks the cdc25-cyclin complex formation. Third, a molecule which inhibits or inactivates the putative activating domain on type B cyclin can be introduced into cells, thus preventing activation of the cdc PTPase.

In another embodiment, inhibitors of the catalytic activity of cdc25 PTPase are introduced into cells. Such inhibitors are low molecular weight agents, such as peptides and inorganic or organic compounds.

The present invention also includes a method of screening compounds or molecules for their ability to inhibit the function of cdc25 protein or the binding of the cdc25 protein with the cyclin/cdc2 complex. For example, cells as described herein, in which a cdc25 gene is expressed, can be used. A compound or molecule to be assessed for its ability to inhibit cdc25 protein function or binding to the cyclin/cdc2 complex is contacted with the cells, under conditions appropriate for entry of the compound or molecule into the cells. Inhibition of the cdc25 protein or of complex formation will result in arrest of the cells or a reduced rate of cell division. Comparison with cell division of an appropriate control (e.g., the same type of cells without added test drug) will demonstrate the ability or inability of the compound or molecule to inhibit the cyclin. Alternatively, an in vitro assay can be used to test for compounds or molecules able to inhibit cdc25 PTPases or their binding to the cyclin/cdc25 complex. In this in vitro assay, the three components (cdc25 PTPase, cyclin and cdc2 (the latter two either individually or as a cyclin/cdc2 complex such as inactive cyclin/cdc2 complex from interphase cells) are combined with a potential cdc25 inhibitor. The activity of the potential inhibitor is assessed by determining whether cdc25 binds cyclin or cyclin/cdc2 complex or whether cdc2 is activated, as evidenced by histone kinase activity. This method can make use of the teachings of Jessus et al. (*FEBS Letters* 66:4–8 (1990)) and DuCommun and Beach (*Anal. Biochem.* 187: 94–97 (1990)), the teachings of which are incorporated herein by reference. For example, in an assay for cdc25 inhibitors, inactive cyclin/cdc2 complex can be placed in the wells, cdc25 and a test compound or molecule added to wells and cdc2 activation assessed. In the presence of a cdc25 inhibitor, cdc2 activation will be prevented or reduced (less than would occur in the absence of the test compound or molecule).

Existing compounds or molecules (e.g., those present in fermentation broth or a chemical "library") or those developed to inhibit the cyclin activation of its protein kinase can be screened for their effectiveness using this method. Drugs which inhibit cdc25 protein catalytic activity, inhibit complex formation or degrade or otherwise inactivate cdc25 are also the subject of this invention.

The present invention also includes an assay in which cdc25 tyrosine phosphatase, such as cdc25 protein or recombinant human cdc25 tyrosine phosphatase, is used to screen for compounds which alter entry into mitosis (passage from late G2 into the M phase of the cell cycle). In one embodiment of the assay, a calorimetric assay can be used to determine the ability of compounds to inhibit the cdc25 tyrosine phosphatase, which is an activator of the protein kinase MPF. As described herein, a glutathione-S-transferase/cdc25A tyrosine phosphatase fusion protein produced in *Escherichia coli* and purified displays a phosphatase activity towards p-nitrophenylphosphate. This fusion protein, designated GST-cdc25A, has been used to assess the inhibitory effect of compounds on cdc25 phosphatase activity. In a similar manner, as also described herein, other fusion proteins can be produced and used in the same or a similar assay format. These fusion proteins can differ from GST-cdc25A in either or both of their components. For example, a component other than GST (e.g., maltase binding protein) can be included in the fusion protein with cdc25A. Alternatively, another member of the cdc25 family (e.g., cdc25B, cdc25C) can be the tyrosine phosphatase component. In another embodiment, cdc25 protein is used.

The present method is a simple and rapid screening test which, in one embodiment, uses a fusion protein such as recombinant p80$^{cdc25}$, assayed through its p-nitrophenylphosphate phosphatase activity, as a target to test for potential antimitotic compounds. The method has been carried out as a rapid calorimetric microtitration plate assay to test compounds currently used in cancer therapy, and a compound recognized to be a tyrosine phosphatase inhibitor. The therapeutic compounds tested did not display an ability to inhibit cdc25, in the assay as described; the reported tyrosine phosphatase inhibitor (vanadate) was shown, however, to totally inhibit cdc25. Thus, the present method has been shown to be useful in identifying compounds which inhibit an essential cell cycle-regulating component; it provides a highly specific screen for antimitotic drugs.

In one embodiment of the present method, a fusion protein which includes cdc25 is combined, under appropriate conditions, with: 1) an agent to be assessed for its effects on cdc25 and, thus, on passage from late G2 into the M phase; and 2) an appropriate cdc25 substrate, such as p-nitrophenylphosphate or inactive cdc2/cyclin B. The resulting combination is maintained for sufficient time for cdc25 to act upon the cdc25 substrate and the reaction is terminated (e.g., by gross alteration of the pH of the combination). Phosphatase activity of the combination is determined using a known technique, such as by measuring the optical density of the combination and comparing it with a predetermined standard or a control (e.g., a predetermined relationship between optical density and extent of cdc25 inhibition or a combination which includes the same components as the "test" combination except for the agent being assessed).

The fusion protein used in the present method can be produced by known genetic engineering techniques, as described in Example 14. That is, a DNA or RNA construct encoding the fusion protein is introduced into an appropriate host cell, in which the construct is expressed, thus producing the fusion protein. The fusion protein is separated (and, preferably, purified) from the host cell and used in the assay. Alternatively, the fusion protein can be produced by joining the two separately produced components. As described in Example 15, a fusion protein in which the two components are glutathione-S-transferase and human cdc25A has been produced and used in the subject method.

In a second embodiment, cdc25 protein, such as cdc25A, cdc25B or cdc25C protein, can be used in the subject method. In this embodiment, cyclin/cdc2 can be used as the cdc25 substrate; an agent to be tested is combined with cdc25 protein and cyclin/cdc2 and the tyrosine phosphatase activity of cdc25 is assessed, as described above. Results are compared with a predetermined standard or with a control (see Example 14).

The cdc25 substrate used can be any synthetic or naturally-occurring substance toward which cdc25 demonstrates phosphatase activity. In the embodiment described herein, the cdc25A substrate used is p-nitrophenylphosphate. Other substrates which can be used include peptides that mimic the site of cdc2 phosphorylation or the full inactive cdc2/cyclinB pre-enzyme complex. Others can be identified by using known methods of determining phosphatase activity.

Agents to be tested for their ability to alter cdc25 tyrosine phosphatase activity can be those produced by bacteria, yeast or other organisms, or those produced chemically. The compounds tested herein, as described in Exmaple 18, included 15 drugs currently used in cancer therapy and vanadate, a recognized tyrosine phosphatase inhibitor. The 15 therapeutic agents showed no inhibitory activity. In contrast, vanadate was shown to totally inhibit GST-cdc25A phosphatase. The present method is useful to identify agents potentially effective as antiproliferative agents and agents which are useful in treating or preventing inflammation or psoriasis, or other diseases relating to cell proliferation.

The present invention will now be illustrated by the following examples, which are not intended to be limiting in any way.

Experimental Procedures

The following experimental procedures were used in carrying out the work described in Examples 1–6.

Three highly degenerate primers corresponding to the consensus cdc25 protein sequence were designed taking into account homology between the *S. pombe* cdc25, *Drosophila* string and *S. cerevisiae* mihi gene products. 5' degenerate primers corresponding to the amino acid sequence IIDCRT/FP (or E) Y E (SIC-1: ATIATIGATTGCCGITA/TCCCI-TAC/TGA and SIC-2: ATIATIGATTGCCGITA/TC-GAITAC/TGA) (SEQ ID NO. 5) and a 3' primer corresponding to the amino acid sequence I/V F H C E F (ST-C: A/TA/GAAC/TTCA/GCAA/GTGA/GAAA/G/TA), (SEQ ID NO. 6) where I corresponds to inosine, were prepared. The 50 ml PCR reaction mixture contained 50 mM KCl; 10 mM TrisHCl(pH 8.3); 1.5 mM $MgCl_2$; 0.01% gelatin; 0.2 mM each of dATP, dCTP, dGTP and dTTP; 0.5 unit of *Thermus aquaticus* (AmpliTaq DNA polymerase (Perkin-Elmer/Cetus)), 2 mM each of the 5' primers (SIC-I and SIC-1)) 5 mM of the 3' primer (ST-C) and 100 mg of human N-Tera cells cDNA library made in ggtlo by Jacek Skowronski (Cold Spring Harbor Laboratory). Four cycles of 94° C. for 1 min, 40° C. for 3 min and 72° C. for 1 min were performed in a DNA thermal cycler (Perkin-Elmer/Cetus). The reaction products were separated on the 2% agarose gel and the expected size (approximately 160 bp) fragments were subcloned into SmaI-digested pBluescript SK(-) vector (Stratagene, La Jolla, Calif.). Nine clones were sequenced, with the sequence clearly indicating cloning of cdc25 homologues. Two different PCR products were detected: one of them was almost identical to recently cloned human cdc25 homologue (CDC25Hs, Sadhu, K. et al., *Proc. Natl. Acad. Sci. USA* 87:5139–5143 (1990)), and the other corresponded to a previously uncharacterized cDNA, here called cdc25 A. The N-Tera cdc25 A PCR-derived clone (p5wl) was used to screen the human N-Tera cell library at low stringency. After plaque purification, inserts of nine positive clones were subcloned into the EcoRI site of the pBluescript SK(-) plasmid. Inserts from two phages containing the entire open reading frame of the cdc25 A cDNA were analyzed by restriction mapping (plasmids 4g1.3 and 211.1, containing inserts of 2.4 and 3.9 kb). Plasmid 4g1.3 contained a deletion of 1.4 kb at the 3' untranslated region of the cDNA and was chosen for complete sequencing. Sequence analysis was performed on both strands using a chain termination method on an automated sequencing system (Applied Biosystems 373A).

Further analysis indicated that one of the original nine phage clones corresponded to a different cdc25 homolog; this is designated cdc25 B. This phage gave rise to two EcoRI fragments (0.9 and 1.5 kb) but did not represent a whole open reading frame. In order to obtain a complete cDNA, the same library was screened with the 0.9 kb EcoRI fragment and an insert representing a complete cDNA (3.0 kb) was subcloned via partial digestion with EcoRI into the pBluescript SK(-) vector. This was used for sequencing.

Production of Antipeptide Antiserum to Human cdc25 A and CDC25Hs

Peptides corresponding to the amino acid sequence CQGALNLYSQEELF-$NH_2$ (#143) (CDC25Hs or cdc25 C) and CKGAVNLHMEEEVE-$NH_2$ (#144) (cdc25 A) were synthesized at the Cold Spring Harbor Laboratory protein core facility, HPLC-purified and coupled to keyhole limpet hemocyanine (KLH) and bovine serum albumin essentially as described (Draetta, G. et al., *Nature* 336:738–744 (1988)). Rabbits were injected with 200 mg of KLH-peptide conjugate every three weeks. Positive sera were obtained after three booster injections. Antibody (K143 and K144) were affinity purified on the BSA-peptide conjugates coupled to the CNBr-Sepharose (Pharmacia, Sweden) according to the manufacturer's instructions. No crossreactivity between peptide #134 and K144 antiserum with the other peptide was detected.

Rescue of the Fission Yeast cdc25 Temperature Sensitive Mutant

A 2.0 kb NcoI-BamHI fragment encoding amino acids 1–526 of human cdc25 A from the p4g1.3 plasmid were subcloned into NcoI-BamHI digested pARTN, resulting in the pARTN-cdc25 A construct harboring human cdc25 A cDNA in sense orientation to the constitutive adh promoter. pARTN is derived from the pART3 (McLeod, et al., 1987) by ligation of an NcoI linker (New England Biolabs) into the SmaI site. An 2.4 kb SmaI fragment from the p4×1.2 plasmid encoding amino acids 32–566 was subcloned into SmaI digested pART3 vector (containing LEU2 marker) resulting in pARTN-cdc25 B cDNA. Both plasmids were transformed into *S. pombe* h+cdc25–22 leul-32 (SP 532) strain. Leu+ transformants were obtained at 26° C.

Cell Culture, Immunoprecipitation

HeLa cells (obtained from the ATCC) were grown at 37° C. in Dulbecco modified Eagle's media (DMDM) supplemented with 10% fetal calf serum. For labelling, cells were washed with methionine minus media (Gibco) and supplemented with lmci/ml $^{35}$S-methionine (Translabel, ICN) for 6–8 hours. Cells were lysed essentially as described (Draetta, G. et al., *Nature* 336:738–744 (1988)) or in the EB buffer (80 mM glycerophosphate, 15 mM $MgCl_2$, 20 mM EGTA, 1 mM DTT), supplemented with protease inhibitors (0.5 mM PMSF, 1 mg/ml of aprotinin, pepstatin, chymostatin, leupeptine, 30 mg/ml of TPCK, 15 mg/ml benzimidine). Lysates were precleared with protein A-Sepharose beads (Pharmacia) (20 ml of the 1:1 slurry); anti-human cdc25 A antiserum (K144) were added (1–5 ml); and after 8–10 hours immune complexes were precipitated with protein A-beads (20 ml of the 1:1 slurry). Beads were washed four times with the lysis buffer and resuspended in 20 ml 2× sample buffer (Laemmli, U. K. *Nature* 227:680–685 (1970)). Immunoprecipitated proteins were resolved on the 10% polyacrylamide gels containing SDS, and visualized by the autoradiography of the dried gel slabs (Anderson, S. J. et al., *J. Virol.* 51:730–741 (1984)). p13 beads were prepared and used to precipitate p34$^{cdc2}$ from HeLd as described earlier (Brizuela, L. et al., *EMBO J.* 6:3507–3514 (1987)).

Bacterial Expression of the cdc25 A and cdc B Phosphatase Assay

A plasmid containing the entire open reading frame of human cdc25 A was digested with NcoI (at amino acid 1), blunt ended with T4 DNA polymerase, heat inactivated, extracted with phenolchlorophorm, ethanol precipitated and digested with EcoRI. The resultant 2.0 kb fragment was gel-purified and ligated into pGEX-2T SmaI/EcoRI digested vector. Resultant plasmid upon transformation into bacteria gave rise to a 90 kd IPTG-inducible protein. Expressed fusion protein was recovered as described (Smith, D. B. and K. S. Johnson, *Gene* 67:31–40 (1988)) on glutathione-sepharose beads (Pharmacia), and eluted with 5 mM freshly prepared glutathione in 50 mM Tris HCl, 50 mM NaCl, 0.1 mM EDTA, 1 mM DTT, at pH 8.0. For expression of cdc25 B, plasmid p4×1.2 was cut with XbaI, then with SmaI (partially) and the 2.4 kb fragment was subcloned into SmaI/XbaI cut pGEX-KG vector (Guan, K. and J. E. Dixon, *Science* 249:553–556 (1991)). Expression of this construct resulted in IPTG-dependent synthesis of the 88 kD GST-cdc25 B fusion protein. Phosphatase activity of the purified cdc25 A protein (4.5 mg or 50 pmoles) was assayed in 0.5 ml 20 mM Tris HCl, pH 8.0, 1 μM EDTA, 0.1% b-mercaptoethanol, 20 mM p-nitrophenylphosphate (PNPP). Absorbance at 410 nm was determined using a molar absorptivity of $1.78 \times 10^4 M^{-1} cm^{-1}$ to calculate the concentration of the p-nitrophenolate ion generated in the assay. For cdc25 B the assay was performed in the same buffer except at pH 8.8.

Reduced carboxamidomethylated and maleylated lysozyme (RCML) was obtained from N. Tonks in a $^{32}$P- tyrosine phosphorylated form. Approximately 50% of the protein was phosphorylated. $^{32}$P-labeled RCML was used in the phosphatase assay in 50 mM Tris HCl, pH 8.0, 50 mM NaCl, 0.1 mm EDTA, 1 mM DTT at a final phosphate concentration of 10–30 mm. Reactions (30–50 ml) were performed at 30° C. for 10 or 20 min, and after addition of the fatty acid free bovine serum albumin (BSA, Sigma) to 2 mg/ml, proteins were precipitated with 200 ml of 20% trichloroacetic acid, vortexed, incubated at −70° C. for 5 min, thawed, spun in an Eppendorf centrifuge for 5–10 min at the maximal speed and 200 ml supernatants were counted in 2 ml Aquasol (NEN) for 10 min.

Peptide, corresponding to region of p34$^{cdc2}$ undergoing inhibitory tyrosine phosphorylation (NH2-CK-KKVEKIGEGTYGVVYK) (SEQ ID NO. 7) (the peptide sequence which is additional to cdc2 and added to couple the peptide to the beads and/or proteins is underlined) was phosphorylated in vitro using bacterially produced v-Abl (Oncogene Sciences) at conditions described by the manufacturer and purified on the Seppak column (Millipore). Final activity incorporated into peptide was $0.7 \times 10^5$ cpm/mg. Phosphatase activity of the cdc25 A protein against peptide (1 mg of peptide were used in each sample) was assayed at the same conditions as for RCML. Reaction mixture was incubated with acid charcoal as described (Streuli, M. et al., Natl. Acad. Sci. USA 86:8698–8702 (1989)) and 200 ml from total supernatant of 700 ml were counted as described above.

Expression of Cyclin Proteins

In order to express human cyclins in bacteria modified pGEX-3X vector (pGEX-Nco) was prepared by digesting it with SmaI, followed by ligation of, the NcoI linker (described earlier in Experimental procedures); this resulted in a vector where cloning into NcoI site allowed the proper expression of the foreign cDNA. Human cyclin BI and A were synthesized by PCR and their sequence were fully confirmed. cyclin B1 cDNA in the pBluescript SK(−) was cut with NcoI/SmaI and the resultant 1.3 kb fragment was ligated into pGEX-Nco, digested with EcoRI, filled in with Klenow fragment and cut with NcoI. The sequence of cyclin A, including the first ATG codon, was changed to an ncoI site by PCR. To express cyclin A, plasmids containing the complete open reading frame for cyclin A (p4f1.1) were digested with NcoI and EcoRI and the resultant 1.4 kb insert was subcloned into pGEX-Nco cut with NcoI/EcoRI. Human cDNA encoding human cyclin B2 was obtained from Y.Xiong (unpublished), with the first ATG codon changed by PCR to NcoI site, this cDNA was digested with BamHI, blunt ended with T4 DNA polymerase, and digested with the NcoI, and the resultant 1.3 kb fragment was ligated in the pGEX3X-Nco vector prepared as described above for the ligation of cyclinBl cDNA. Mouse CYL1 (cyclin D1) cDNA in the pGEX-3X vector was generous gift from Dr. C. Sherr. Purification of the expressed cyclins was performed essentially as described (Smith, D. B. and K. S. Johnson, Gene 67:31–40 (1988); Solomon, M. J. et al., Cell 63:1013–1024 (1991)), except that after the first extraction, the cell pellets were resuspended in the 50 mM Tris HCl, pH 8.0, 50 mM NaCl, 1 mM EDTA, 1 mM DTT, 1% glycerol, 2M urea and extracted for 10 min on ice. After centrifugation for 30–60 min at 15000 rpm on the RC-5B centrifuge (Beckman), the supernatant was filtered through 0.22 mm filter (Millipore) and applied to the 2 ml glutathione-Sepharose column (Pharmacia), equilibrated with the extraction buffer. columns were washed subsequently with the extraction buffer (10 ml), then with the same buffer lacking urea (10 ml), and fusion proteins were eluted in the same buffer supplemented with 10 mm glutathione. Eluted proteins were dialyzed into phosphatase assay buffer and concentrated by repeated dilution-concentration on the Amicon microconcentrators. Protease inhibitors (PMSF and benzimidine) were added to 0.5 and 5 mM subsequently, and the proteins were stored at 4° C. for 2–3 days or used immediately on the same day. The Bradford assay was used to determine protein concentration.

Microinjection of Antibodies

For microinjection experiments HeLa cells were grown to 20–30 cells in an "island" and injected at time 0 with affinity purified K144 (1 mg/ml) further depleted on the #143 peptide conjugated BSA sepharose. The injection was done in buffer F (20 mM Tris HCl, pH 7.6, 20 mM NaCl, 50 mM KCl, 0.5 mM b-mercaptoethanol, 0.1 mM ATP). All cells in the particular "island" were microinjected and photographs were taken at 8, 18, 24 and 36 hours after microinjection. In a separate set of experiments cells were photographed at 8, 12, 18 and 24 hours after injection. Microinjection of the protein A-Sepharose purified rabbit IgG from the preimmune serum served as a control.

Protein Kinase Assays

For protein kinase assays, p13 beads with bound p34$^{cdc2}$ kinase isolated from the HeLa cells (incubated in the presence of hydroxyurea (10 mM) for 22 hours followed by 4 hour release) were washed twice in the buffer containing 50 mM Tris HCl, pH 8.0, 1 mM EDTA, 1 mM DTT and incubated for 5 min at 30° C. with the additives. Additives included buffer alone, or material eluted with the 0.1 M glycine/HCl, pH 2.5 from the cdc25 A immunoprecipitates, done in the presence or absence of 1 mg of an antigenic peptide (before addition material was neutralized with 1 M Tris HCl, pH 8.0). The precipitates were washed twice with 50 mM Tris HCl, pH 8.0, 10 mM MgCl$_2$, 1 mM DTT (PK-buffer), and finally resuspended in 2 volumes of PK buffer supplemented with 5 mM ATP, 10 mCi of [q$^{-32}$P] ATP (3000 Ci/mmol), and 50 mg/ml of histone H1. After incubation for 15 min at 30° C. the reaction was stopped by polyacrylamide gel sample buffer containing SDS. Labeled proteins were separated on 10% polyacrulamide gels and detected by autoradiography.

EXAMPLE 1

Isolation of cdc25 A AND cdc B cDNA

A human cdc25 genes has previously been described (Sadhu, K. et al. Proc. Natl. Acad USA, 87:5139–5143 (1990)). Further members of what is now shown to be the human cdc25 family have been isolated by means of a PCR-based strategy. This strategy made use of three degenerate oligonucleotide primers designed to correspond to amino-acid regions of consensus between Drosophila melanogaster string (Edgar, B. A. and P. H. O'Farrell, Cell 57:177–187 (1989)), S. pombe cdc25 (Russell, P. and P. Nurse, Cell 45:145–153 (1986)) and S. cerevisiae mihl (Russell, P. et al., Cell 57:295–303 (1989)). Amplification of cDNA from a human N-Tera teratocarcinoma library, followed by cloning of the PCR products into a phagemid vector, allowed nucleotide sequencing of the fragments. This established that a cdc25-related fragment different from that previously described had been cloned.

The insert from one PCR-derived clone (p5wl) was used to screen a human cDNA library in the ggtlo vector. From approximately $10^6$ plaques screened, nine positive clones were obtained. Eight corresponded to the originally cloned PCR product used as the hybridization probe. This is referred to as cdc25 A. A second cdc25 clone, isolated by using low stringency hybridization with pSwl, was called cdc25 B. The longest cDNA clones of cdc25 A and B were subjected to nucleotide sequencing. The region of each that contains the open reading frame is shown in FIG. 1. cdc25 A and cdc25 B are predicted to encode proteins of 526 and 566 amino acids respectively. The calculated isoelectric point for cdc25 A is 6.3, and for cdc25 B is 5.9. Both genes have an initiation codon flanked by a Kozak consensus sequence (PuCC/GATGG) (Kozak, M. *Cell* 44:283–292 (1986)).

Comparison of the amino acid sequence of cdc25 A and cdc25 B and the GenBank data base (release 67) revealed homology to the previously described human cdc25 (Sadhu, K. et al., *Proc Natl Acad. Sci. USA* 87: 5139–5143 (1990)), referred to herein as cdc25 C. This comparison showed that there is 48% identity in the 273 C-terminal region between cdc25 C and A, and 43% identity between C and B. (FIG. 2). *Drosophila* string shares 34.5% identity to cdc25 A in a 362 amino acid region, and 43.9% identify to cdc25 B in a 269 amino acid region (FIG. 2). *S. Pombe* cdc25+ is also related to both cdc25 A and B, though at a lesser level (FIG. 2). Human cdc25 A and cdc25 B proteins also contain conserved amino acids that characterize the "cdc25-box", particularly those in the region potentially involved in cdc25 catalytic activity (L/VFHCEXXXXR) (SEQ ID NO. 8) (Moreno, S. and P. Nurse, *Nature* 351:194 (1991); Gautier, J. and J. Maller, *EMBO J.* 10:177–182 (1991)). All known human cdc25 homologues contain a stretch of 15 identical amino acids in this region, called the highly conserved region (SEQ ID NO. 9) (FIG. 2). Interestingly, the overall similarity between different human cdc25 proteins does not greatly exceed that between humans and such evolutionarily distinct species as *Drosophila*.

EXAMPLE 2

Assessment of the Functional Relationship Between Proteins Encoded by Human cdc25 A, cdc25B and Fission Yeast cdc25

To test whether the human cdc25 A and B genes do indeed encode proteins that are functionally related to fission yeast cdc25, the human genes were subcloned into the *S. pombe* autonomously-replicating expression vector, pARTN (carrying the LEU2 marker under the control of the constitutive alcohol dehydrogenase promoter, as described in experimental procedures). After introduction of the plasmids into an H+ cdc25–22 leul-32 strain, transformants were plated on media either lacking or containing leucine at a permissive (26° C.) or restrictive temperature (36° C.). Both human cDNAs could efficiently rescue the temperature-sensitive mutation of the cdc25 gene. Cells bearing human cDNAs were able to form single colonies with a growth rate similar to wild-type cells. Microscopic examination revealed that cells transformed with either gene were slightly "wee", a phenotype previously observed in fission yeast transformed with the wild-type cdc25+gene on the same type of vector (Russell, P. and P. Nurse, *Cell* 45:145–153 (1986)).

EXAMPLE 3

Demonstration that cdc25 A Acts in Mitosis

In order to test the role of cdc25 A, we prepared polyclonal antibodies against a peptide corresponding to an internal region of the cdc25 A protein (see Experimental Procedures). This serum was used to precipitate $^{35}$S-methionine labeled HeLa proteins. A protein of 75 kD was specifically precipitated in the absence, but not the presence, of competing antigenic peptide (data not shown). Stringent detergent conditions were used that abolish interactions with cdc2 and cyclin. This molecular weight is higher than predicted from the amino acid sequence of the gene; however, in vitro translation of the cdc25 A clone also yielded a protein of 75 kD (not shown). To test whether this protein might activate inactive cyclin B/cdc2, as described in the case of the *Drosophila* string protein (Kumagai, A. and W. G. Dunphy, *Cell* 64:903–914 (1991)) and also in the case of human cdc25 C (Strausfeld, U. et al., *Nature* 351:242–245 (1991)), HeLa cell cdc25 A was eluted from an immunocomplex under conditions of low pH (see Experimental Procedures). The eluted protein did not possess any histone kinase activity (data not shown). This protein was mixed with cdc2/cyclin B, prepared by p13-Sepharose precipitation of an extract of HeLa cells that had been arrested in hydroxyurea and released for four hours (see Experimental Procedures). Under these conditions, the cdc2/cyclin B is relatively inactive as a histone kinase, unless the eluted cdc25 A protein is added (data not shown).

Figure 3B:
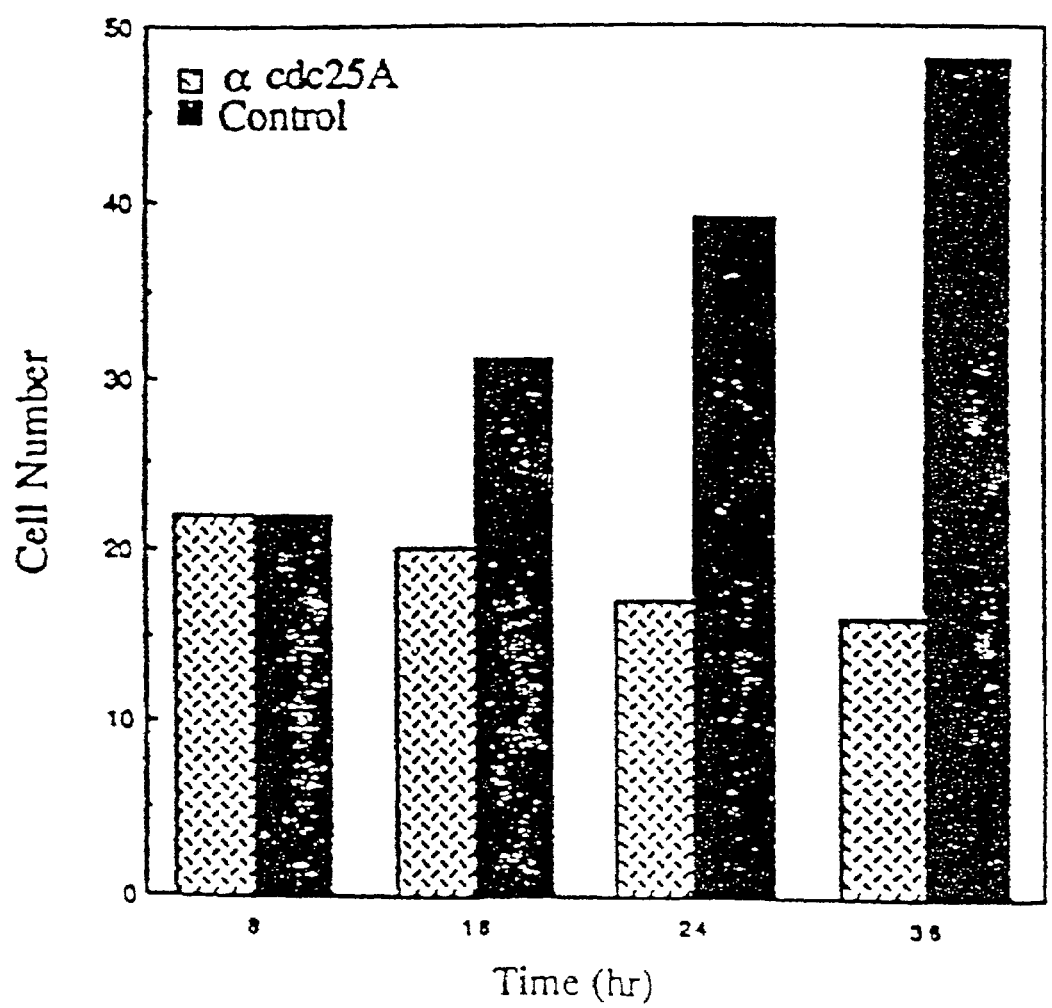

To address the function of cdc25 A protein in human cells, affinity-purified anti-peptide antibodies were microinjected into actively proliferating HeLa cells (see Experimental Procedures). Islands of injected cells were photographed at 8, 12, 18 and 24 hours, and in another set of experiments at 8, 12, 18, 24 and 36 hours. In some cases, cells were stained with anti-rabbit IgG to confirm the success of the anti-cdc25 antibody microinjection. Analysis of the photographs in three such independent experiments led to the conclusion that the antibodies prevent cells from dividing (FIGS. 3A, 3B). The percentage of cells in mitosis (defined as rounded-up mitotic figures) increased progressively following microinjection of anti-cdc25A, but not following a control serum (FIG. 3A). The cell number in each injected island increased in the case of control serum, but gradually declined in the experimental. This is attributed to the failure of cells to divide, coupled with their eventual death (visualized as shrivelled rounded cells) and their dissociation from the surface of the culture plate. In fission yeast, loss of cdc25 function causes cells to arrest in G2, rather than in mid-mitosis as in the present experiment. This, on the basis of sequence homology, function in fission yeast, and, in the case of cdc25 A, functional studies in human cells, the newly-identified human proteins can be classified as relatives of cdc25.

EXAMPLE 4

Activation of cdc25 by B-type Cyclin

In order to study the regulation of the cdc25 phosphatase activity in vitro, human cdc25 A and B were expressed in bacteria as fusion proteins with glutathione-S-transferase (GST, Smith, D. B. and K. S. Johnson, *Gene* 67:31–40 (1988)). Fusion proteins with a relative molecular weight of 90 kD (cdc25 A) and 88 kD (cdc25 B) were isolated by affinity chromatography on glutathione-Sepharose beads as described (Smith D. B. and K. S. Johnson, *Gene* 67:31–40 (1988)). Human cyclins A, B1, B2 and murine D1 (CYLI, Matsushime, H. et al., *Cell* 65:701–713 (1991)) were expressed as fusion proteins with GST; purified proteins were obtained by the same method.

To investigate the potential regulation of cdc25 activity by cyclin, it was necessary to find a substrate that bore no conceivable relationship to cdc2, the presumed physiological substrate of the phosphatase. cdc2 binds to cyclin (Draetta, G. et al., *Cell* 56:829–838 (1989)) and thus addition of cyclin to a reaction containing cdc2 as the substrate would probably result in alteration of the target substrate and confuse the interpretation of any observed effect. For this reason a substrate often employed in tyrosine phosphatase studies, namely reduced, carboxamidomethylated and maleylated lysozyme (RCML) was used. (Tonks, N. K. et al., *J. Biol. Chem.* 263:6731–6737 (1988)). This substrate was labelled on tyrosine residues with $^{32}P$ and kindly provided by N. Tonks.

Figure 4A:
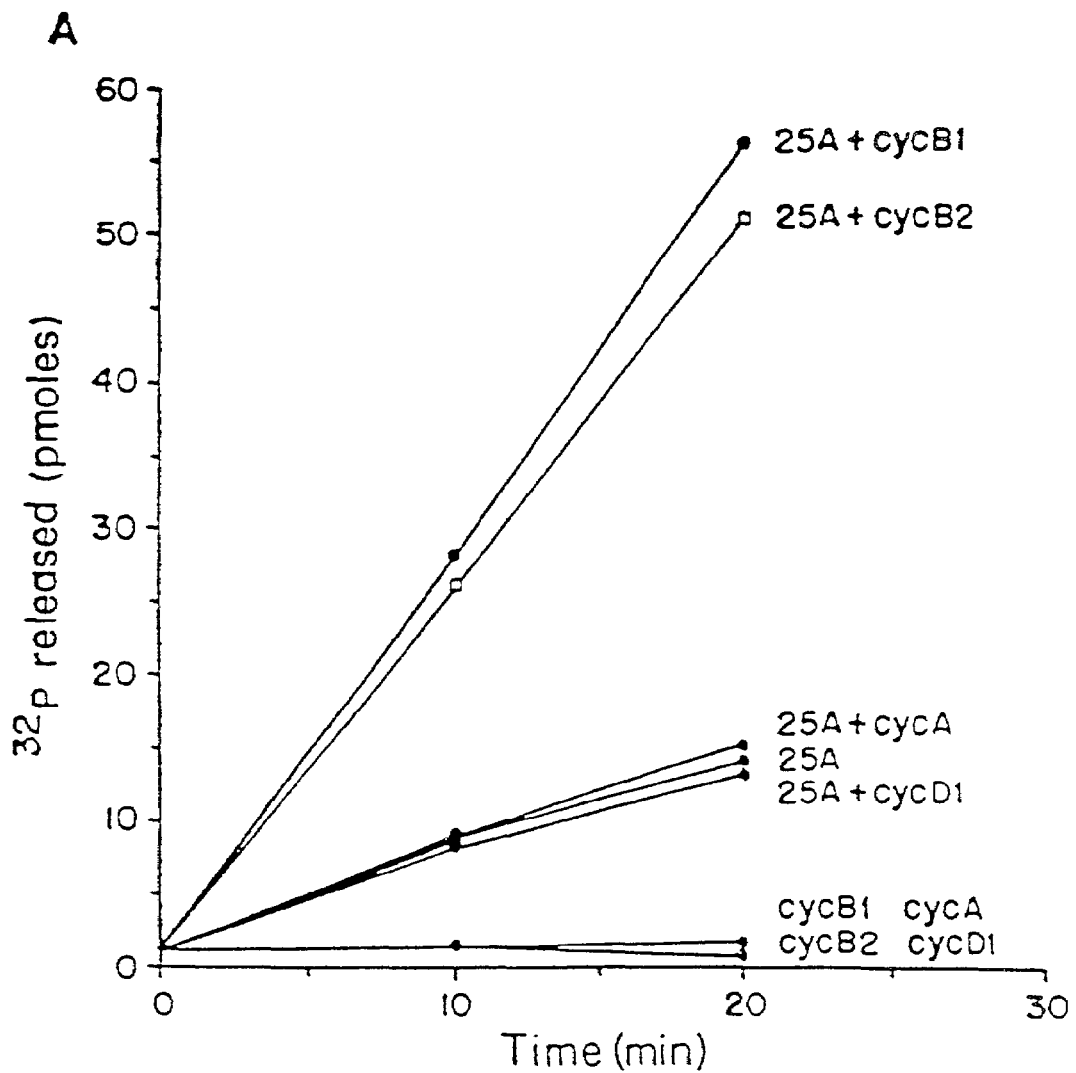
FIGS. 4A–C show activation of cdc25A phosphatase by mitotic cyclins. Human GST-cdc25 A fusion protein was used to assay release of 32P: substrates were tyrosine phosphorylated, reduced carboxamidomethylated, maleylated lyzosyme (RCML) (A); cdc2-derived peptide (B); or PNPP (C). A410 indicates adsorbance at 410 nm.
Figure 5:
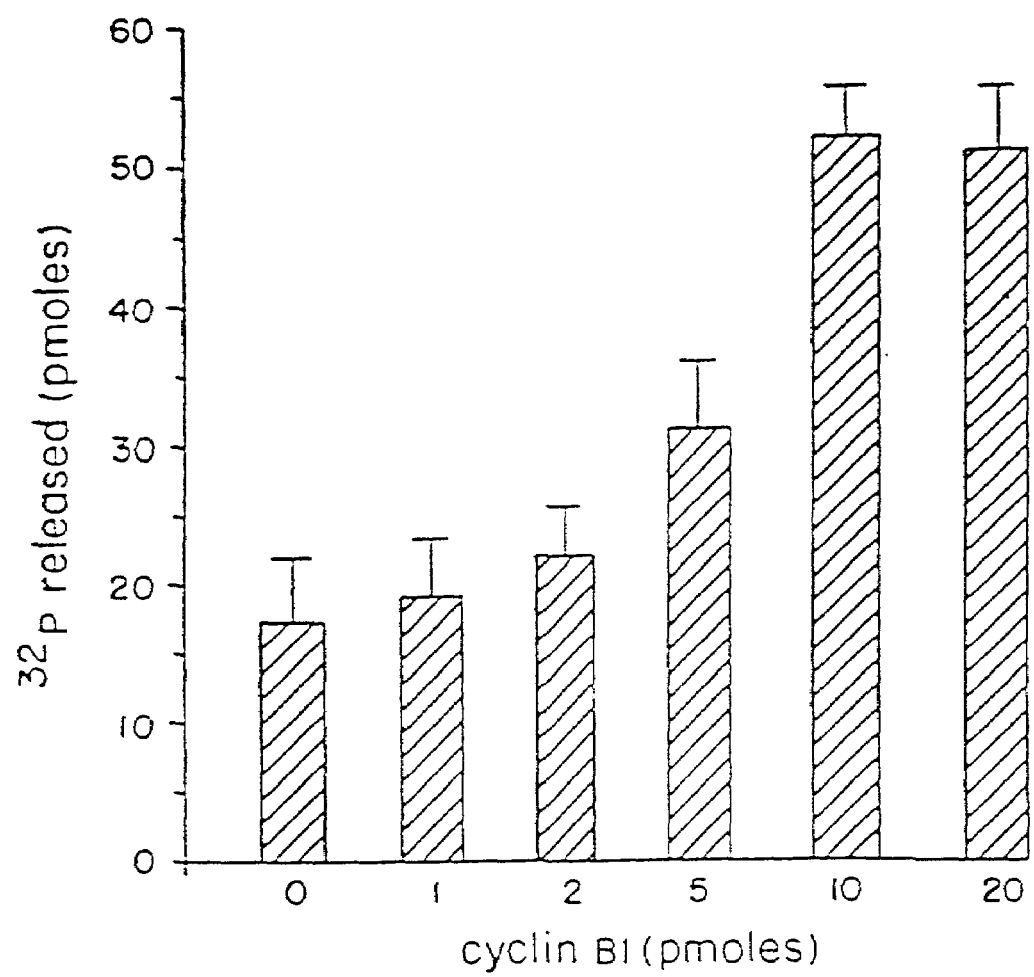
FIG. 5 is a graphic representation of dose-dependent activation of the cdc25 A by cyclin B1. Bars indicate the standard error in three experiments.

Cyclins purified from bacteria displayed no phosphatase activity against RCML (FIG. 4A). However, cdc25 A had an endogenous tyrosine phosphatase activity (FIG. 4A; see also Experimental Procedures), that is linear for at least 30 minutes (data not shown). If it is assumed that all the bacterial cdc25 protein is equally catalytically active, we can calculate that each molecule of cdc25 releases approximately one phosphate per 10 minutes. Addition of cyclin A or D to the reaction mixture had neither stimulatory nor inhibitory effect on the endogenous activity of cdc25 A at any concentration tested (FIG. 4A). However, similar addition of either cyclin B1 or B2 had an approximately four-fold stimulatory effect (FIG. 4A). In the preceding experiments, 10 pmoles of cyclin and cdc25 protein were used in the reaction mixture. The dependency of the activation of cdc25 on the amount of added cyclin B1 was also investigated. The assay was performed either without cyclin or with the addition of 1, 2, 5, 10, or 20 pmoles of the cyclin B1. The reaction was performed for 20 min, and terminated by the addition of trichloroacetic acid (TCA). Activation was observed to plateau at 10 pmoles of added cyclin B1 and no further effect was detected at higher concentrations (FIG. 5). Thus, under these experimental conditions, maximal activation of cdc25 is achieved by stoichiometric addition of cyclin B.

Figure 4B:
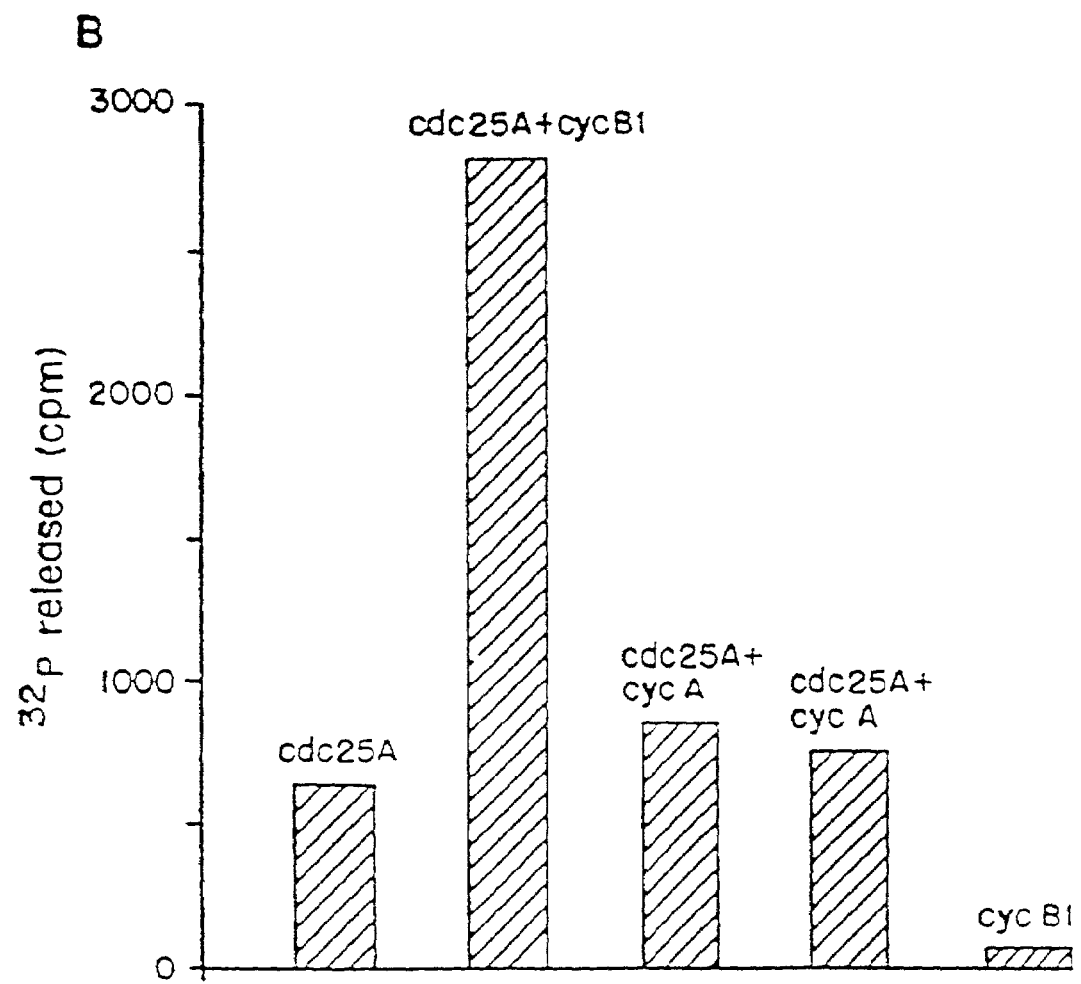
Figure 4C:
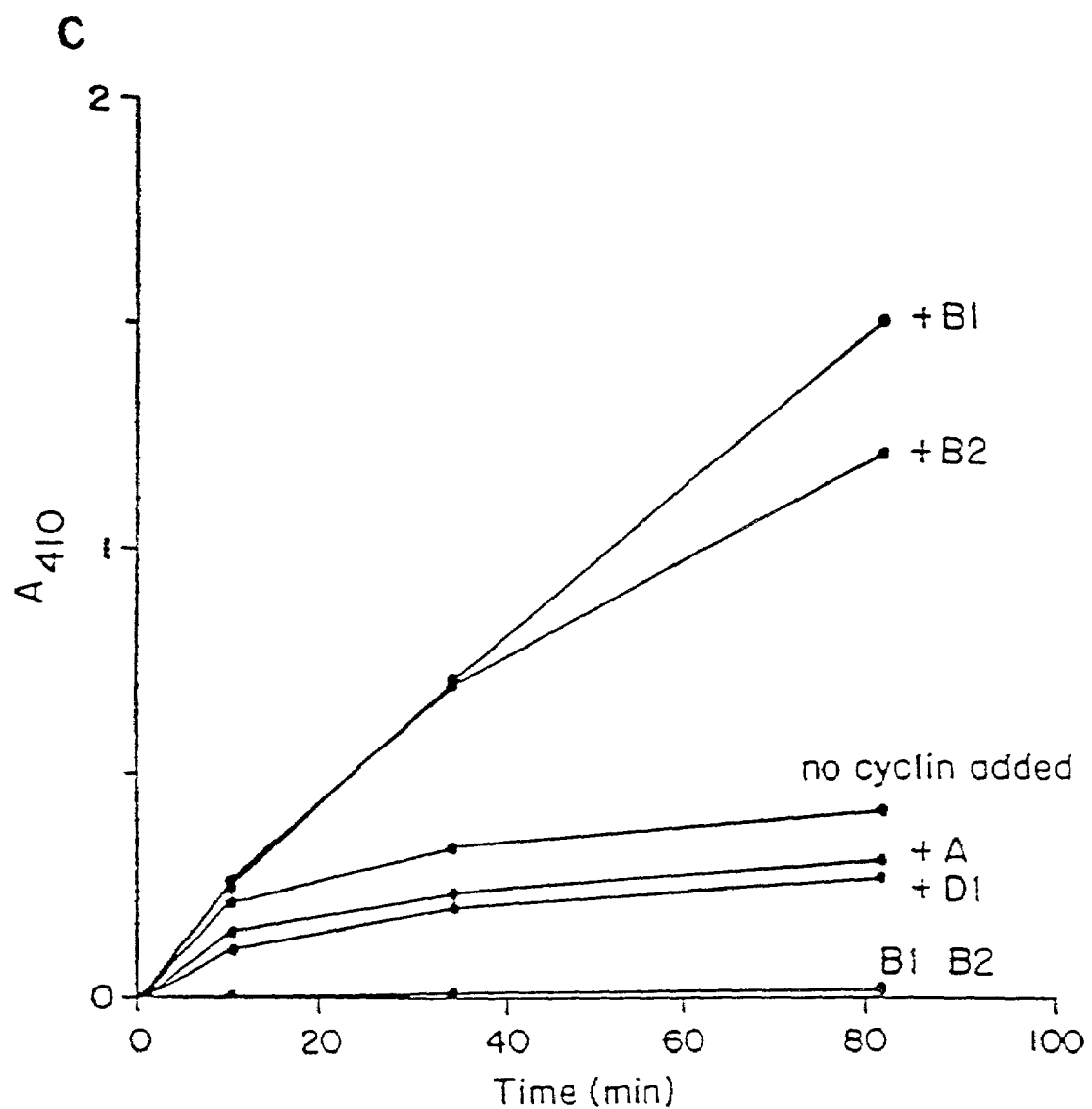

Whether the same stimulatory effect of B-type cyclins on the catalytic activity of cdc25 A could be detected was tested using other substrates including p-nitrophenylphosphate (PNPP), another frequently used PTPase substrate (Tonks, N. K. et al., *J. Biol. Chem.* 263:6731–6737 (1988); Guan, K. et al., *Nature* 350:359–362 (1991); Dunphy, W. G. and A. Kumagai, *Cell* 67:189–196 (1991)) and the 18-mer peptide corresponding to the N-terminal region of the cdc2 protein surrounding Tyr15 (see Experimental Procedures). In the first case, the catalytic rate for cdc25 A was activated four to five-fold, specifically in the presence of cyclin B (FIG. 4C). 50 pmoles of cyclin and cdc25 protein were used in this PNPP assay. When the 18-mer peptide was used, similar levels of cdc25 A activation by B cyclins were detected (FIG. 4B). 10 pmoles of cdc25 protein and cyclin were used in this experiment.

EXAMPLE 5

Cyclin B1/cdc2 Interacts with cdc25A

To investigate the possibility of stable interaction between cdc25 and cyclin, as predicted from the data on the activation of the cdc25 A phosphatase activity and additional work described in Example 4, immunoprecipitates with the cdc25 A anti-peptide antibody described above were prepared. In this case, immunoprecipitations were performed under conditions favorable for retention of cdc25 protein complexes (see Experimental Procedures). Immunoprecipitates were probed with anti-cyclin B1 antibody (kindly provided by J. Pines) or the anti-cdc2 antibody (G6), prepared against C-terminal peptide of the cdc2 (Draetta, G. et al., *Nature* 336:738–744 (1988)). Clear signals were detected in both cases, indicating that human cdc25 protein is present in a complex with both cyclin B1 and cdc2 (data not shown).

EXAMPLE 6

Figure 6:
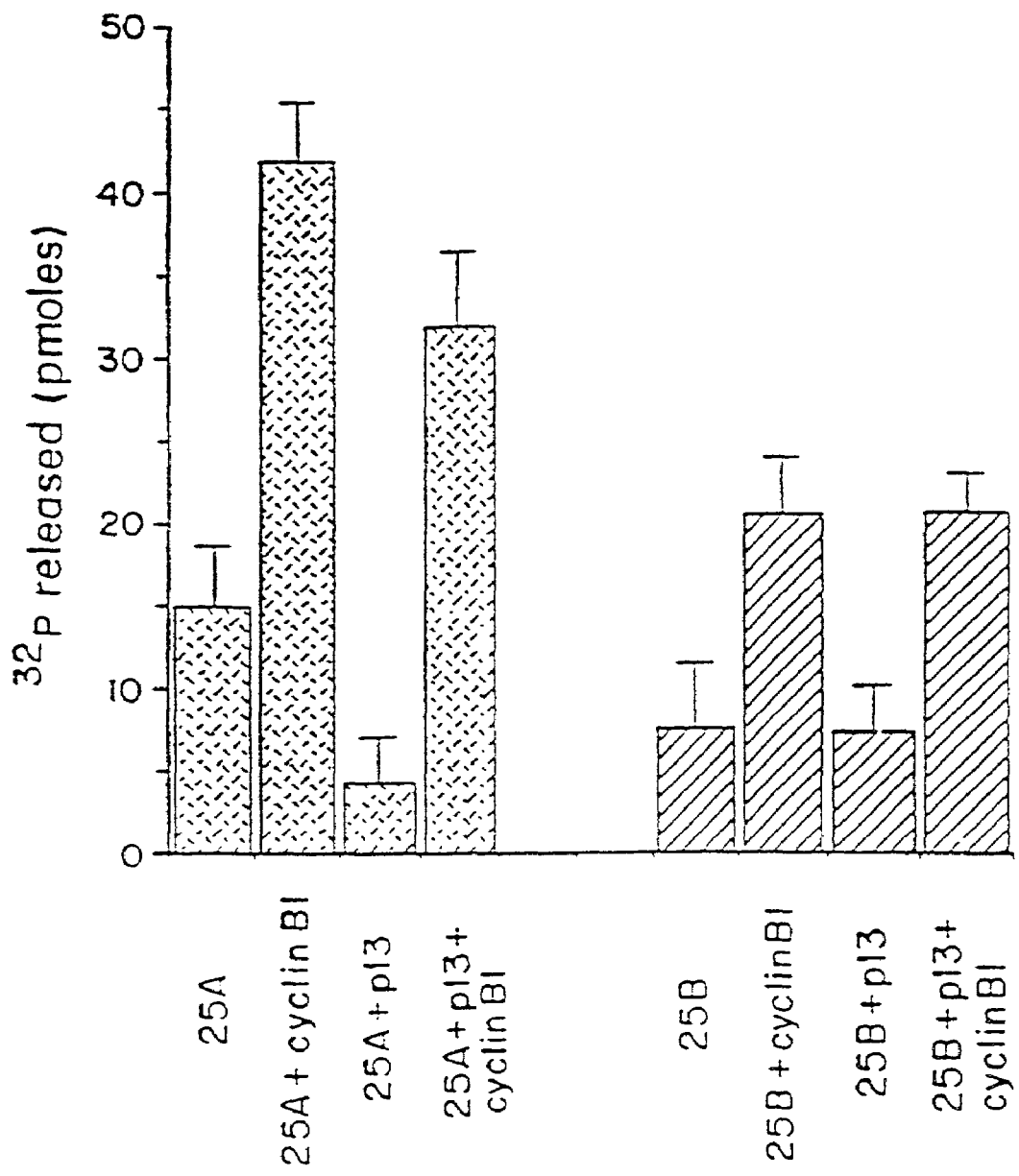
FIG. 6 shows inhibition of cdc25 phosphatase activity by p13 (Sucl). In the left panel, cdc25 A (10 pmoles) and right panel, cdc25 B (10 pmoles) was used. Bars indicate the standard error in three independent experiments.

Selective Inhibition by p13 p13 is at essential subunit of the cdc2 protein kinase. An excess of p13 can, however, inhibit activation of pre-MPF. To test whether p13 could directly influence the phosphatase activity of either of the human cdc25 proteins, the phosphatase assay as described in Examples 4 and 5 was performed with the addition of a final concentration of 25 mM, with or without 0.5 mM (10 pmoles) cyclin B1. In the case of cdc25 A, a 2–3-fold inhibition of the endogenous phosphatase activity was observed by adding p13 at 25 mM (FIG. 6). This concentration is far higher than that of the cdc25 protein itself (0.3 mm) but is similar to that required to prevent pre-MPF activation in vivo or in vitro (Dunphy, W. et al., *Cell* 54:423–431 (1988); Dunphy, W. and J. W. Newport, *Cell* 58:181–431 (1989)). Addition of cyclin B1 in an equimolar concentration to the phosphatase was able to substantially negate the inhibitory effect of p13, causing an eight-fold activation (FIG. 6). The behavior of cdc25 B was quite different. In preliminary experiments, it was found that the pH optimum for this phosphatase is 8.8 (as opposed to 8.0 for cdc25 A). At this pH, cyclin B1 could activate cdc25 B to a similar degree to cdc25 A. However, no effect of p13 on the activity of cdc25 B was observed either in the presence or absence of cyclin B (FIG. 6).

Experimental Procedures

The following experimental procedures were used in the work described in Examples 7–13.

Oocyte and Extract Preparation

*Xenopus laevis* propbase oocytes were prepared as described (Jessus, C. et al., *FEBS Letters* 266: 4–8 (1987)) and were induced to mature by 1 mM progesterone. *Xenopus* metaphase unfertilized eggs were activated in 1 mm HEPES pH7.4, 8.8 mH NaCl, 10 mg $CaCl_2$, 33 mH $Ca(NO_3)_2$, 0.1 mH KCl, 82 mM $MgSO_4$, 5 mg/ml $Ca^{2+}$-ionophore A-23187 (Sigma) and 100 mg/ml cycloheximide (Sigma). After 40 min, eggs were either homogenized and referred as "activated eggs", or washed, transferred to incubation buffer (Jessus, C. et al., *FEBS Letters* 266:4–8 (1987)) and homogenized at different times. To prepare extracts, oocytes were washed extensively in extraction buffer EB (Cyert, H. S. and M. W. Kirschner, *Cell* 53:185–195 (1988)) 80 mM b-glycerophosphate pH7.3, 20 mM EGTA, 15 mM $MgCl_2$, 1 mM DTT), then lysed at 4° C. in one volume of EB with protease inhibitors (25 mg/ml leupeptin, 25 mg/ml aprotinin, 1 mM benzamidine, 10 mg/ml pepstatin, 10 mg/ml soybean trypsin inhibitor and 1 mM PMSF) and centrifuged for 1 h at 100,000×g at 4° C. The supernatant was then filtered through 0.22 mm Millex-GV filters (Millipore) before use.

Prpearation and Use of p13-Sepharose Beads

P13 was purified and conjugated to sepharose as previously described (Brizuela, L. et al., *EMBO J.* 6:3507–3514 (1987)). After preincubation for 1 h with Sepharose CL-6B and centrifugation to remove non-specific binding, 100 ml of oocyte extracts were incubated for 90 rain at 4° C. under constant rotation with 400 ml of EB plus protease inhibitors and 20 ml of p13-Sepharose beads. p13-Sepharose beads were further washed three times in EB, then either resuspended in 80 ml of Laemmli sample buffer (Laemmli, U. K., Nature 227:680–685 (1970)) and boiled for 3 min, or immediately used for histone HI kinase assay.

Preparation of 0–33% Ammonium Sulfate Extracts

Prophase oocytes were rinsed extensively in EB, then lysed in one volume of EB with protease inhibitors at 4° C. and centrifuged at 41,000 rpm for 90 rain at 4° C. in Ti.41 rotor (Beckman). The supernatant was removed and filtered through 0.22 mm Millex-GV filters (Millipore). Ammonium sulfate fractionation was carried out by addition of 0.5 volume of a saturated solution of ammonium sulfate in EB to the extract, incubation on ice for 45 min, centrifugation at 41,000 rpm for 90 min at 4° C. and resuspension of the pellet in one-tenth of the initial volume to a final protein concentration of 15 mg/ml, as determined with the BioRad protein assay kit with q-globulin as the standard. This extract (termed 0–33% fraction) was dialyzed for 2 h at 4° C. against EB in the presence of protease inhibitors and stored at −70° C. until use. For activation, extracts were incubated at room temperature with 1 mM ATP, 50 mg/ml creatine phosphokinase (Boehringer Mannheim) and 10 mM creatine phosphate (Boehringer Mannheim).

Antibodies

Fission yeast cdc25 protein was produced in *Escherischia coli* expressing the full-length protein (Ducommun, B. et al., Biochem. Biophys. Res. Comm. 167:301–309 (1990)). Bacterially produced cdc25 protein was purified and solubilized as described by Kumagai and Dunphy (Kumagai, A. and W. G. Dunphy, Cell 64:903–914 (1991)). To purify B1 anti-cdc25 serum (Ducommun, B. et al., Biochem. Biophys. Res. Comm. 167:301–309 (1990)), bacterially expressed cdc25 protein was subjected to SDS-polyacrylamide electrophoresis and extracted by incubation of the excised gel pieces in PBS (phosphate saline buffer) (0.1% SDS 0.5% b-mercaptoethanol) at 37° C. for 16 h. After centrifugation, the protein was concentrated on Centricon-10 microconcentrators (Amicon) and incubated with nitrocellulose (0.45 mM; Schleicher and Schuell) for 3 h at room temperature. After three ten minute washes in PBS (0.1% SDS), filters were blocked for 4 h at room temperature with PBS containing 1.5% BSA (bovine serum albumin, Boehringer Mannheim) and 0.5% Tween-20. After three ten-minute washes in PBS (0.1% SDS), filters were incubated at room temperature for 16 h with B1 anti-cdc25 serum (Ducommun, B. et al. Biophys. Res. Comm. 167:301–309 (1990)), and diluted four times in PBS 1.5% BSA. Filters were then washed three times in PBS (0.1% Tween-20) and once for 10 min with PBS. Purified anti-cdc25 antibody was eluted with 1 ml of 100 mM glycine pH2.5, and 200 ml of 1 M TRIS pH8.0 was added after 1 min. After addition of 300 ml of PBS (10% BSA, 0.5% NaN$_3$), the purified antibody was stored at 4° C. until use. For some control experiments, the purified antibody was preadsorbed overnight at 4° C. with 10 mg/ml purified bacterially expressed yeast cdc25 protein before Western blotting.

Anti-B2 cyclin antibody was a gift from J. Gautier (rabbit polyclonal purified antibody directed against *Xenopus* cyclin B2; Gautier, J. et al., Cell 60:487–494 (1990); Gautier, J. and J. Maller, EMBO J. 10:177–182 (1991)). Anti-cdc2 antibody was a rabbit polyclonal purified antibody directed against thr full-length *Schizosaccharomyces pombe* cdc2 (Draetta G. et al., Cell 50:319–325 (1987)). Anti-phosphotyrosine antibody was a mouse IgG monoclonal antibody (Ab-1, Oncogene Science). The sensitivity of this anti-phosphotyrosine antibody ought to have been be sufficient to allow the detection of phosphotyrosine in the cdc25-associated cdc2, since a comparable amount of prophase cdc2 was easily recognized. Therefore, the absence of signal observed in metaphase cdc2 bound to cdc25 suggested that this population of cdc2 was not phosphorylated on tyrosine.

Immunoprecipitation and Western Blot Analysis 100 ml of oocyte extracts in EB were mixed with 400 ml of Eb and incubated for 1 h at 4° C. with 30 ml of protein A-agarose beads (Pierce). Anti-cdc25 antibody (dilution 1:100), anti-cyclin B2 antibody (dilution 1:50) or anti-cdc2 antibody (dilution 1:500) were then added to the supernatant and after a 5h incubation at 4° C., 30 ml of protein A-agarose beads were added. After an additional 1 h incubation at 4° C., the beads were either washed four times in EB and then eluted by boiling for 30 min in 80 ml Laemmli sample buffer or resuspended in kinase buffer (50 mM TRIS pH7.4, 10 mM MgCl$_2$, 5 mM EGTA, 1 mM DTT) for a subsequent histone HI kinase assay.

To elute *Xenopus* cdc25 protein from immunoprecipitates, immunocomplexes were resuspended in 250 ml of 100 mM glycine pH2.5. After a 2 min stirring, 50 ml of 1 M TRIS pH8.0 was added. The supernatant was recovered, concentrated on Centricon-10 microconcentrators (Amicon) and bovine serum albumine was added to a final concentration of 0.1%.

Electrophoresis and Western blot analysis with anti-cdc25 antibody (dilution 1:500), anti-cyclin B2 antibody (dilution 1:100) or anti-cdc2 antibody (dilution 1:000) were performed as previously described (Booher, R. N. et al., Cell 58:584–497 (1989)). By scanning immunoblots of initial extracts before anti-cdc25 immunoprecipitation, extracts after anti-cdc25 immunoprecipitation and anti-cdc25 immunoprecipitates (FujiX Bas 2000 Image Analyzer), it was we estimated that 70% of the full cellular amount of cdc25 was immunoprecipitated by the anti-cdc25 antibody. In a parallel way, the amount of p72 associated with cdc2 or cyclin B2 in immunoprecipitates was quantified by Image Analyzer (FujiX Bas 2000), by using anti-cdc25 immunoblots of crude extracts as a reference of the full cellular amount of cdc25. 20% of the total cellular amount of cdc25 was found either in anti-cdc2 immunoprecipitates or in anti-cyclin B2 immunoprecipitates. To quantify the amount of cdc2 or cyclin B2 associated with cdc25, equal amounts of oocyte extracts (from 10 oocytes, equivalent to 200 mg of proteins) were either precipitated on p13-Sepharose or immunoprecipitated with anti-cdc25 antibody. p13-sepharose beads completely clear the extract of cdc2 and cyclin B2 as ascertained by Western blotting (data not shown) and, therefore, p13-precipitate represents the full cellular amount of cdc2 and cyclin B2. On the other hand, the anti-cdc25 immunoprecipitate contains only the cdc2 and the cyclin B2 that are associated with p72. Both p13-precipitates and anti-cdc25 immunoprecipitates (each the equivalent of 10 oocytes) were loaded on the same electrophoresis gel and blotted with the anti-cdc2 antibody or the anti-cyclin B2 antibody. The relative amounts of cdc2 and cyclin B2 detected in both extracts were determined by PhosphorImager (Molecular Dynamics) or Image Analyzer (FujiX Bas 2000). The amount of cdc2 present in p13-Sepharose precipitate is 20-fold higher than that detected in the anti-cdc25 immunoprecipitate. Thus, 5% of the total cdc2 is associated with p72. The amount of cyclin B2 present in p13-Sepharose precipitates is 6-fold higher than that detected in the anti-cdc25 immunoprecipitate. Thus, 17% of the total cyclin B2 is associated with p72.

Histone H1 Kinase Assay p13-precipitates or immunocomplexes were washed three times in kinase buffer and then resuspended in 50 ml of kinase buffer containing 0.2 mg/ml histone H1 (Boehringer Mannheim), 50 mM ATP and 1 mCi[c$^{32}$P]ATP (PB.10168, Amersham). After a 30 min incubation at 30° C., the reactions were terminated by the addition of 30 ml Laemmli sample buffer (Laemmli, U. K., *Nature* 227:680–685 (1970)). Samples were electrophoresed on a 12% polyacrylamide gel. After staining with coomassie blue and autoradiography, $^{32}$P incorporation into histone H1 was quantified by scintillation counting of excised gel pieces.

Protein samples from the 0–33% fraction (in a volume of 10 ml of EB) were mixed on ice with 40 ml of kinase buffer containing 0.2 mg/ml histone H1, 25 mM ATP, 2 m Ci[q$^{32}$P] ATP and 10 mM cAMP dependent protein kinase inhibitor peptide (P3294, Sigma). After incubation for 10 min at 30° C., samples were treated as previously described.

EXAMPLE 7 cdc25 Protein in *Xenopus* Oocytes

An anti-cdd25 serum directed against fission yeast cdc25 was used to determine whether a cdc25 protein is present in *Xenopus* oocytes. This serum, previously referred to as B1 (Ducommun, B. et al., *Biochem. Biophys. Res. Comm.* 167:301–309 (1990)), was affinity purified as described in the Experimental Procedures. It recognizes the full-length yeast cdc25 product expressed in *E. coli* but no signal is detectable in an *E. coli* lysate before transcriptional cdc25 induction of cdc25 (Ducommun, B. et al., *Biochem. Biophys. Res. Comm.* 167:301–309 (1990)).

Extracts were prepared from the following cells: meiotic prophase-blocked oocytes; meiotic metaphase unfertilized eggs; eggs activated in the presence of cycloheximide, that therefore lack cyclin and are blocked in an interphase state (Murray, A. W. and Kirschner, M. *Nature* 339:275–280 (1989)); and eggs after 120 min of activation (after completion of the first MPF cycle). These extracts were probed with the affinity-purified serum in an immunoblot. A 72 kD polypeptide was detected in each sample. No signal was detected using the same procedure but substituting preimmune serum or purified antibody preadsorbed with soluble bacterially-expressed yeast cdc25 protein for the affinity-purified serum (data not shown). Furthermore, two other purified polyclonal antibodies directed against the yeast cdc25 protein were able to recognize the same 72 kD protein from *Xenopus* extracts. (Ducommun, B. et al., *Biochem. Biophys. Res. Comm.* 167:301–309 (1990)).

To test whether the 72 kD species might be immunoprecipitated by the anti-cdc25 antibody, extracts from prophase oocytes, metaphase unfertilized eggs and interphase eggs activated in the presence of cycloheximide were precipitated with the purified anti-cdc25 antibody and probed with the same purified serum in immunoblots. Again, a protein of 72 kD was specifically detected by the cdc25 antibody (data not shown). In contrast, no signal was detected when the same procedure was used in the absence of *Xenopus* extract, formally demonstrating that the 72 kD protein observed in the immunoprecipitates is not due to the presence of cdc25 protein in the antibody preparation (a contamination that could occur during immuno-affinity purification of the antibody).

To obtain soluble 72 kD polypeptide, proteins were eluted from anti-cdc25 immunoprecipitates at low pH (see Experimental Procedures) and the amount of 72 kD protein was determined by immunoblotting with the cdc25 antibody. Again, the same level of 72 kD protein was found in prophase oocytes, metaphase unfertilized eggs, interphase-blocked activated eggs and eggs after the completion of the first MPF cycle (data not shown).

EXAMPLE 8

Demonstration that cdc25 Activates the M-Phase Kinase

Human and *Drosophilia* cdc25 proteins are able to trigger activation of cdc2/cyclin B in vitro (Kumagai, A. and W. G. Dunphy, *Cell* 64:903–914 (1991); Strausfeld, U. et al., *Nature* 351:242–245 (1991)) by dephosphorylating cdc2 (Dunphy, W. G. and A. Kumagai, *Cell* 67:189–196 (1991); Gautier, J. et al., *Cell* 67:197–211 (1991)). As a further test that the anti-cdc25 antibody recognized *Xenopus* cdc25, it was investigated whether the 72 kD protein eluted from immunocomplexes could stimulate inactive cdc2. To prepare inactive enzyme from prophase oocytes p13-Sepharose beads were used. *Xenopus* cdc2 protein binds strongly and quantitatively to fission yeast p13. (Dunphy, W. et al., *Cell* 54:423–431 (1988)). The p13-Sepharose bound cyclin B/cdc2 complex from prophase oocytes has a low histone H1 kinase activity. Protein eluted from anti-cdc25 immunoprecipitates of either prophase oocytes or metaphase unfertilized eggs was added to inactive prophase p13-bound cdc2. After a 30 min preincubation at 30° C. in the presence of cdc25-immunocomplex eluates, the p13-precipitate was extensively washed and then assayed for histone H1 kinase activity. Both prophase and metaphase cdc25 stimulated histone H1 kinase activity 12-fold. The possibility that some of the histone H1 kinase activity present in the anti-cdc25 immunocomplexes (see below) might be responsible for this increase of kinase activity was eliminated. First, the p13-Sepharose precipitate was extensively washed after preincubation with the immunoeluted material, and before assay of kinase activity. Second, the histone H1 kinase activity found associated with the eluted metaphase proteins was insufficient to account for the observed 12-fold stimulation of the p13-bound enzyme (approximately 500 units of final activity). Third, the prophase immuno-eluted material was also able to activate cdc2, although it did not contain any kinase activity (data not shown). It was therefore concluded that an active *Xenopus* cdc25 protein was precipitated by the affinity-purified anti-cdc25 antibody from both prophase oocytes and metaphase eggs. It is surprising that active p72 could be extracted from *Xenopus* oocytes in which cdc2/cyclin B is inactive and tyrosine phosphorylated.

It was also tested whether p72 from either prophase oocytes or metaphase unfertilized eggs could affect the activity of either fully activated cdc2/cyclin from metaphase unfertilized eggs or cdc2 that is inactive in the absence of cyclin (material extracted from eggs activated in the presence of cycloheximide). In neither case did p72 have any effect on the histone H1 kinase activity of cdc2 (data not shown). The 135 units of activity found in one sample of activated eggs is probably due to the basal activity of cdc2 from activated eggs (66 units) combined with the kinase activity associated with metaphase cdc25 and therefore does not represent a real stimulation of cdc2. It was concluded that p72 only acts on the tyrosine phosphorylated enzyme.

EXAMPLE 9

Demonstration that Activation of pre-MPF Requires cdc25

Figure 8:
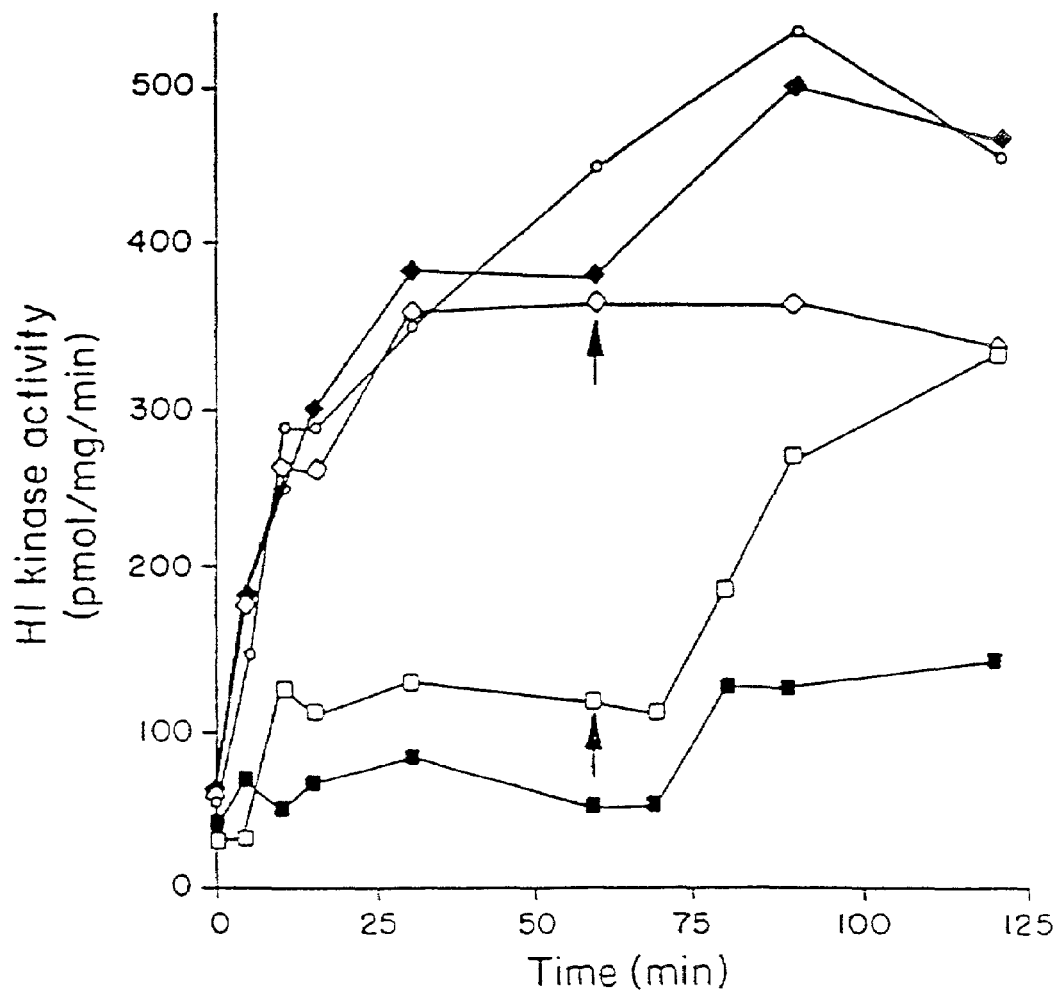
FIG. 8 is a graphic representation demonstrating that *Xenopus* cdc25 is required for activation of M-phase kinase. The ammonium sulfate fraction of the prophase oocyte extract was incubated in the presence of either PBS-2% BSA (filled diamonds) preimmune anti-cdc25 serum (oper circles; open diamonds), or purified anti-cdc25 antibody (filled rectangles; open rectangles). In two cases (open diamonds; open rectangles), soluble bacterially expressed yeast cdc25 protein (100 mg/ml) was added (indicated by arrows).

Xenopus prophase oocytes contain an inactive form of MPF that can be activated by a post-translational mechanism both in vivo (Wasserman, W. and Y. Masui, *Exp. Cell. Res.* 91:381–388 (197S); Gerhart, J. et al., *J. Cell Biol.* 98:1247–1255 (1984)) and in vitro (Cyert, M. S. and M. W. Kirschner, *Cell* 53: 185–195 (1988); Dunphy, W. G. and J. W. Newport, *Cell* 58: 181–191 (1989)). Addition of an ATP-regenerating system to a prophase oocyte extract (33% ammonium sulfate precipitated fraction) is sufficient to induce tyrosine dephosphorylation of cdc2 and stimulation of its latent activity (Cyert, M. S. and M. W. Kirschner, *Cell* 53: 185–195 (1988); Dunphy, W. G. and J. P. Newport, *Cell* 58: 181–191 (1989)). In order to determine if endogenous p72 was required for this activation process, the effect of adding anti-cdc25 antibody to the 0–33% ammonium sulfate fraction from phophase oosytes was explored. 200 ml of the 0–33% ammonium sulfate fraction of high speed extract of phophase oocytes was incubed for 15 min at 40° C. At 0 min, samples were transferred to room temperature, and 1 mM ATP, 10 mM creative phosphase and 50 mg/ml creative phosphokinase were added. Following the addition of this ATP-regenerating system to the extract, the histone H1 kinase was rapidly activated (FIG. 8). By contrast, a 15 min preincubation of the extract with anti-cdc25 antibody resulted in a prolonged inhibition of the activation process. Addition of the preimmune anti-cdc25 serum had no effect (FIG. 8). This result suggests that the endogenous p72 is required for histone H1 kinase activation and is inactivated after immunocomplexing with the antibody. It was further found that bacterially-expressed cdc25 protein at 100 mg/ml, when added at 60 minutes, can overcome the inhibition caused by the anti-cdc25 antibody (FIG. 8), indicating that the antibody acts specifically on the endogenous cdc25 protein.

EXAMPLE 10

Demonstration of an Association Between cdc25 and cdc2 at M-Phase

To investigate further the mechanism of cdc2 activation by cdc25, the possibility that cdc25 might directly associate with the M-phase enzyme was tested. Extracts of either prophase oocytes, metaphase unfertilized eggs or activated eggs were immunoprecipitated with an anti-cdc2 antibody and probed with the same anti-cdc2 antibody. As expected, a strong signal was obtained (data not shown). Since the anti-cdc2 antibody recognized a single 34 kD band, it was assumed that this antibody does not react with cdk2, a 32 kD cdc2-like protein encoded by the *Xenopus* Egl gene (Paris, J. et al., *Proc. Natl. Acad. Sci. USA* 88:1039–1043 (1991)). Similar anti-cdc2 immunoprecipitates were probed with the purified anti-cdc25 antibody. A 72 kd band was observed in the metaphase unfertilized eggs, but not in the resting prophase oocytes or in the eggs activated in the presence of cycloheximide. In a control experiment in which the purified anti-cdc25 antibody was preadsorbed with bacterially expressed cdc25 protein before immunoblotting, no signal was detected. These results indicate that cdc25 stably associates with cdc2 at M-phase.

To further test the existence of an association between cdc2 and cdc25 the converse experiment was also performed. Cdc25 was immunoprecipitated from prophase oocytes, metaphase unfertilized eggs and activated eggs using the purified anti-cdc25 antibody. An equal amount of cdc25 was precipitated in each case (data not shown). The anti-cdc25 immunoprecipitates were then probed with the anti-cdc2 antibody. A 34 kD protein was detected in the metaphase unfertilized eggs, but not in the prophase oocytes or in the activated eggs (data not shown). To confirm that the 34 kD protein detected in this experiment was indeed cdc2, prophase oocyte, metaphase unfertilized egg and activated egg extracts were first depleted of the cdc2/cyclin B complex by preincubation with p13-Sepharose and then immunoprecipitated with the purified anti-cdc25 antibody. Immunoblotting these immunocomplexes with anti-cdc2 antibody revealed complete depletion of the 24 kD protein (data not shown). Therefore, it was concluded that the 34 kD protein was cdc2. Moreover, cdc2, which is present at the same level in prophase oocytes, metaphase eggs and interphase eggs, was not recognized in an immunoblot by the purified anti-cdc25 antibody, indicating that there was no cross-reactivity between cdc2 and the anti-cdc25 antibody. By quantifying the signal in immunoblots (see Experimental Procedures), it was estimated that the amount of cdc2 present in anti-cdc25 immunoprecipitates represented approximately 5% of the total cellular cdc2 at metaphase and that the amount of cdc25 present in anti-cdc2 immunoprecipitates represented 20% of the cellular content of cdc25.

EXAMPLE 11

Demonstration that Cyclin B is Associated with cdc2 and cdc25 at M-Phase

Since the active cdc2 from M-phase is associated with cyclin (Brizuela, L. et al., *Proc. Natl. Acad. Sci. USA* 86:4362–4366 (1989); Draetta, G. et al., *Cell* 56:829–838 (1989); Gautier, J. et al., *Cell* 60:487–494 (1990)), it was further investigated whether cyclin B is present in association with cdc2 and cdc25 at M-phase. Extracts of either prophase oocytes, metaphase unfertilized eggs or activated eggs were precipitated with p13-Sepharose and probed with an anti-cyclin B2 antibody. Cyclin B2 was present in both prophase oocytes and metaphase unfertilized eggs (data not shown). As already noted (Gautier, J. and J. Maller, *EMBO J.* 10:177–182 (1991); Kobayashi, A. H. et al., *J. Cell Biol.* 114:755–765 (1991)), two immunoreactive bands of cyclin B2 are detectable, of which the upper band was a phosphorylated form appearing during meiotic maturation. In contrast, cyclin B2 was not detectable in eggs activated in the presence of cycloheximide (data not shown). The same extracts were immunoprecipitated with the anti-cyclin B2 antibody and then probed with the purified anti-cdc25 antibody. The 72 kD protein was detected in association with cyclin B2 in the metaphase eggs but not in the prophase oocytes or in the interphase eggs (data not shown). The converse experiment was then performed. The three types of cell extracts were immunoprecipitated with the purified anti-cdc25 antibody and probed with the anti-cyclin B2 antibody. Cyclin B2 was associated with cdc25 in metaphase unfertilized eggs, but not in resting prophase oocytes or activated eggs (data not shown). The phosphorylated form of cyclin B2 was predominantly associated with cdc25. As a control experiment, prophase oocyte, metaphase egg and activated egg extracts were first depleted of cdc2/cyclin B by incubation with p13-Sepharose and then immunoprecipitated with the anti-cdc25 antibody. No signal was detected after probing these extracts with the anti-cyclin B2 antibody, indicating that the 51 kD band previously detected was indeed cyclin (data not shown). It was therefore concluded that cdc25 binds to the cyclin B/cdc2 complex at metaphase. The amount of cdc25 present in anti-cyclin B2 immunoprecipitates was estimated to be the same as the proportion of cdc25 previously found in association with cdc2 (20% of the full cellular content of cdc25). In contrast, it was determined that cdc25-associated cyclin B2 represents 17% of the total population of cyclin B2, which is a higher percentage than the amount of cdc25-associated cdc2 (5%).

EXAMPLE 12

M-phase Kinase Associated with cdc25 is Active

At metaphase, cdc2 is predominantly tyrosine dephosphorylated and active as a histone H1 kinase. Since cdc2 is associated with cdc25 only at metaphase, the tyrosine phosphorylation state and the kinase activity of the complexed cdc2 were investigated. By immunoblotting p13-Sepharose precipitates with an anti-phosphotyrosine antibody, it was confirmed that cdc2 was heavily tyrosine phosphorylated in prophase oocytes and substantially dephosphorylated in metaphase unfertilized eggs, although different batches of metaphase eggs display a somewhat different degree of cdc2 tyrosine dephosphorylation, as previously demonstrated (Dunphy, W. G. and J. W. Newport, *Cell* 58:181–431 (1989); Jessus, C. et al., *FEBS Letters* 266:4–8 (1990). No tyrosine phosphorylation of cdc2 could be detected in eggs that were activated in the presence of cycloheximide and thus lack cyclin B. (See also Solomon, M. J. et al., *Cell* 63:1013–1024 (1991)). When anti-cdc25 immunocomplexes from prophase oocytes, metaphase unfertilized eggs or activated eggs were probed with the same anti-phosphotyrosine antibody, no phosphotyrosine-containing proteins were detected, despite the presence of abundant cdc2 in the immunocomplex from metaphase unfertilized eggs (data not shown). If the cdc25-associated cdc2 were substantially tyrosine phosphorylated, a signal of sufficient strength would have developed in the immunoblot. This result suggested that the fraction of cdc2 associated with cdc25 in metaphase unfertilized eggs was likely to be active as a histone H1 kinase. This was found to be true: the kinase activity in p13-Sepharose precipitates was very low in prophase oocvtes, was increased 31-fold in metaphase unfertilized eggs and declined during activation in the presence of cycloheximide. Histone H1 kinase activity was detected in anti-cdc25 immunoprecipitates from metaphase eggs. The activity detected in anti-cdc25 immunoprecipitates from prophase oocytes and activated eggs was comparable to the background levels (data not shown), indicating that no cdc2 kinase was present in these extracts. By comparing the relative metaphase kinase activity in P-13 Sepharose precipitates and anti-cdc25 immunoprecipitates (approximately 20-fold different) it was found that the specific activity of cdc2 was essentially identical in each sample.

EXAMPLE 13

Association Between cdc2/Cyclin B and cdc25 is Periodic

Figure 9:
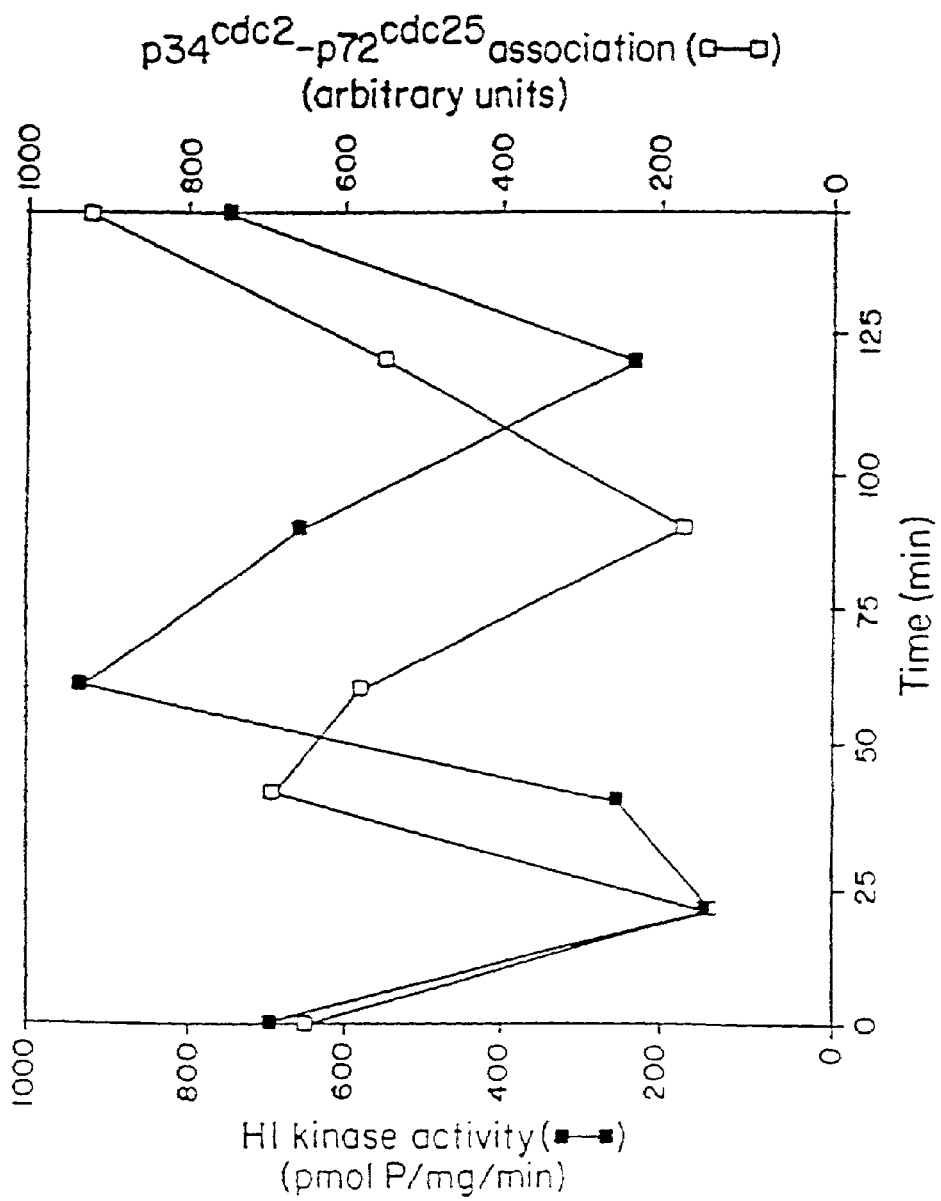
FIG. 9 is a graphic representation evidencing periodic physical association of cdc25 and cdc2/cyclin B. Filled rectangles indicate histone H1 kinase activity of p13-Sepharose precipitates; open rectangles indicate amounts of cdc2 found in anti-cdc25 immunocomplexes by blotting with anti-cdc2 antibody.

The abundance of the *Xenopus* cdc25 protein appears not to vary during meiotic maturation or in the first embryonic cycle (data not shown). However, the protein was only found in association with cdc2 and cyclin B in metaphase unfertilized eggs. To investigate this more closely, metaphase unfertilized eggs were parthenogenetically activated in the presence of $CA^{2+}$-ionophore and calcium, and histone H1 kinase activity was assessed in p13-Sepharose precipitates during the first 150 min. At various intervals, 100 eggs were homogenized, centrifuged, and precipitated. The histone H1 kinase activity disappeared about 20 min after activation, reappeared between 60 and 90 min at time of the first cleavage, declined again and finally peaked at time of the second mitotic cleavage (FIG. 9). Samples taken from the same cell extracts were immunoprecipitated with anti-cdc25 antibody and immunoblotted with anti-cdc2 serum to estimate the extent of association. Relative amounts of cdc2 present in the anti-cdc25 immunoprecipitates were quantified by Phosphor-Imager. The periodic interval of the association between cdc2/cyclin B complex and cdc25 was identical to the periodicity of the p13-bound enzyme activity (FIG. 9). However, a slight phase shift was noted. The association peaked slightly ahead of the overall histone H1 kinase. In repeated experiments (data not shown), the pattern of association was always the same. However, in some cases the phase shift between the histone H1 kinase activity and the association between cdc2/cyclin B and cdc25 was less obvious.

Experimental Procedures

The following materials, methods and procedures were used in carrying out the work described in Examples 14–18.

Materials and Methods

Chemicals sodium fluoride, sodium orthovanadate, nitrophenol, cis-platinum, isopropyl β-D-thiogalacto-pyranoside (IPTG), 1-methyladenine, dithiothreitol (DDT), EGTA, EDTA, MOPS, β-glycerophosphate, leupeptin, aprotinin, soybean trypsin inhibitor, benzamidine, histone H1 (type III-S), CNBr-activated sepharose 4B, glutathione-agarose (G 4510), glutathione (G 4251), nonidet P40 (NP40), Tris, LB Broth base, were obtained from Boehringer-Mannheim; p-nitrophenylphosphate (p-NPP) (disodium sal hexahydrate, ref. 12.886.82) was from Janssen Chimica.

$[\gamma^{-32}P]$-ATP (PB 168) and $^{125}I$]-protein A (IM 144) were obtained from Amersham.

G1 anti-p34$^{cdc2}$ antibodies and anti-p80$^{cdc25}$ antibodies (directed against the cdc25C phosphatase peptide $H_2N$-QEGERQLREQIALLVKDMS-COOH) were kindly provided by Dr. G. Draetta (Heidelberg); anti-cyclin B$^{cdc13}$ (starfish) antibodies were generously donated by Dr. T. Kishimoto (Tokyo); anti-phosphotyrosine antibodies were generously given by Dr. J. Y. J. Wang (La Jolla); antibodies against $H_2N$-VEKIGEGTYGVVYKARHKLS-COOH (a p34$^{cdc2}$ peptide containing the regulatory threonine-14 and tyrosine-15 residues) were kindly provided by Dr. L. Tung (Philadelphia). This last antibody does not recognize tyrosine-phosphorylated p34$^{cdc2}$ but only tyrosinedephosphorylated p34$^{cdc2}$ but only tyrosinedephosphorylated p34$^{cdc2}$.

Buffers

Oocyte homogenization buffer contained 60 mM β-glycerophosphate, 15 mM p-NPP, 20 mM MOPS pH 7.2, 15 mM EGTA, 15 mM $MgCl_2$, 1 mM DTT, 0.1 mM sodium vanadate, 0.1 mM sodium fluoride, 10 μg leupeptin/ml, 10 μg aprotinin/ml, 10 μg soybean trypsin inhibitor/ml, 100 μM benzamidine. This buffer had previously been shown to stabilize the starfish meiotic oocyte M phase-specific histone H1 kinase (Pelech, S. L. et al., *Biochemistry* 26:7960–7968 (1987)).

Bead buffer contained 50 mM Tris pH 7.4, 5 mM NaF, 250 mM NaCl, 5 mM EDTA, 5 mM EGTA, 0.1% NP40, 10

μg leupeptin/ml, 10 μg aprotinin/ml, 10 μg soybean trypsin inhibitor/ml and 100 μM benzamidine.

Tris-Buffered Saline (TBS) contained 50 mM Tris pH 7.4, 150 mM NaCl.

Phosphate-Buffered Saline (PBS) contained 9.6 mM phosphate, 2.7 mM KCl, 140 mM NaCl.

Lysis buffer contained 1% NP40, 1 mM EDTA, 1 mM DTT, 10 μg leupeptin/ml, 10 μg aprotinin/ml, 10 μg soybean trypsin inhibitor/ml and 100 μM benzamidine/ml in PBS.

Tris buffer A contained 50 mM Tris pH 8.0, 50 mM NaCl, 1 mM EDTA, 1 mM DTT.

Elution buffer contained 10 mM glutathione in Tris buffer A.

Preparation of G2 and M Phase Oocytes

G2 and M phase oocytes were prepared as follows: gonads were removed from mature starfish (*Marthasterias glacialis*), collected in Northern Brittany. They were either directly frozen in liquid nitrogen and kept at −80° C. (G2 oocytes) or incubated with 10 μM 1-methyladenine in natural seawater for 10 min (M. oocytes). By that time all the oocytes had entered the M phase, although they were still in the gonads. These were then removed from the incubation medium, rapidly blotted on filter paper, directly frozen in liquid nitrogen and kept at −80° C.

Transfer buffer contained 39 mM glycine, 48 mM Tris, 0.37% SDS, 20% methanol.

Bacterial Growth and cdc25A Induction

An *E. coli* strain (BL 21(DE3)) containing a plasmid encoding the genes fusion construct of glutathione-S-transferase (GST) and human cdc25A under the control of IPTG was used (Galaktinonov, K. and D. Beach, *Cell* 67:1181–1194 (1991)). *E. coli* were first grown overnight at 37° C. in the presence of 100 μg ampicillin/ml LB medium. Four ml of this preculture were inoculated/liter of LB containing 100 μg ampicillin/ml. Incubation was pursued at 30° C. until the culture O.D. at 500 nm had reached a value between 0.8 and 1.00 (about 4–5 hrs). At this moment, 0.4 mM IPTG was added and the culture incubated at 25° C. for at least 7 hours. Cells were then harvested by a 3000 g centrifugation for 15 min at 4° C. Pellets were kept frozen at −80° C. until extraction.

EXAMPLE 14 p80$^{cdc25}$ Controls p34$^{cdc2}$/Cyclin B Activation

Figure 10:
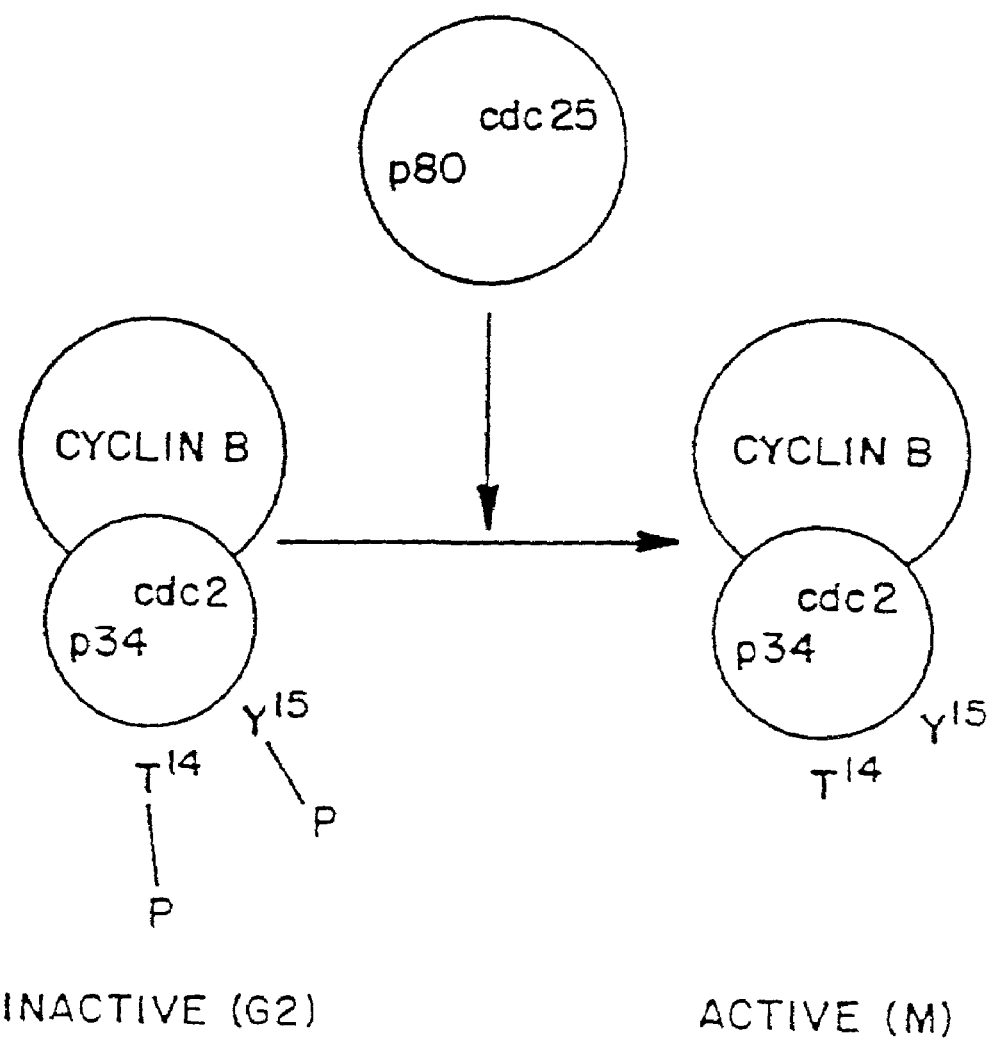
FIG. 10 is a schematic representation of the control by p80$^{cdc25}$ of activation of inactive pre-MPF (G2) to active MPF (M phase).

Inactive pre-MPF (G2) is constituted of cyclin B and p34$^{cdc2}$ phosphorylated on its threonine-14 and tyrosine-15 residues. p80$^{cdc25}$ is the phosphatase which dephosphorylats the tyrosine-15 residue, and possibly threonine-14. Its action leads to activation of the p34$^{cdc2}$/cyclin B$^{cdc13}$ kinase responsible for induction of the G2/M transition. The interaction of these components and activation of inactive pre-mPF (G2) is represented in FIG. 10. An agent to be tested for its ability to alter stimulation of kinase activity is combined with the inactive pre-MPF (G2) and the effects, if any, are determined. If an agent tested is an inhibitor, the inactive pre-MPF will not be activated.

EXAMPLE 15

Production and Purification of GST cdc25A Phosphatase

A fusion construct between the glutathione-S-transferase (GST) gene and human cdc25A was built in a plasmid vector (Galaktionov, K. and D. Beach, *Cell* 67:1181–1194 (1991)). Transfected and expressed in *E. coli*, it produced large amounts of the corresponding fusion protein which was purified by affinity chromatography on glutathione-agarose beads. The protocols of production, purification and assay of the GST-cdc25A phosphatase are described in detail below. Production involved culture of recombinant *E. coli* and classical induction of GST-cdc25A expression by IPTG. One-step affinity-chromatography on glutathione-agarose allowed the purification of the GST-cdc25A phosphatase. The optimum ratio of bacterial extract volume/glutathione-agarose volume was found to be 6–10 to 1. GST-cdc25A was either preserved as the bacterial pellet (very stable), the supernatant of the centrifuged bacterial extract or after affinity-purification ad in the presence of 40% glycerol (final volume).

The bacterial pellet was disrupted by sonication in lysis buffer at 4° C. The homogenate was centrifuged for 30 min at 4° C. at 100,000 g; the supernatant was recentrifuged under similar conditions; the final supernatant was then immediately mixed and rotated with glutathione-agarose beads (equilibrated with lysis buffer) for 30 min at 4° C. (6–10 volumes of supernatant/1 volume of packed beads). The glutathione-agarose beads were washed three times with 10 volumes of lysis buffer, followed by four washes with 10 volumes of Tris buffer A. Elution of the fusion protein was induced by 3–4 successive washes with 10 mM glutathione in Tris buffer A. The efficiency of the elution was monitored by a phosphatase assay. Active fractions were pooled and used directly or supplemented with 40% glycerol prior to storage at −80° C.

Glutathione-agarose beads easily recycled by a wash with 1 M NaCl, followed by equilibration with lysis buffer.

EXAMPLE 16

Assay of the GST-cdc25A Phosphatase Activity Towards D-Nitrophenylyphosphate

Figure 12A:
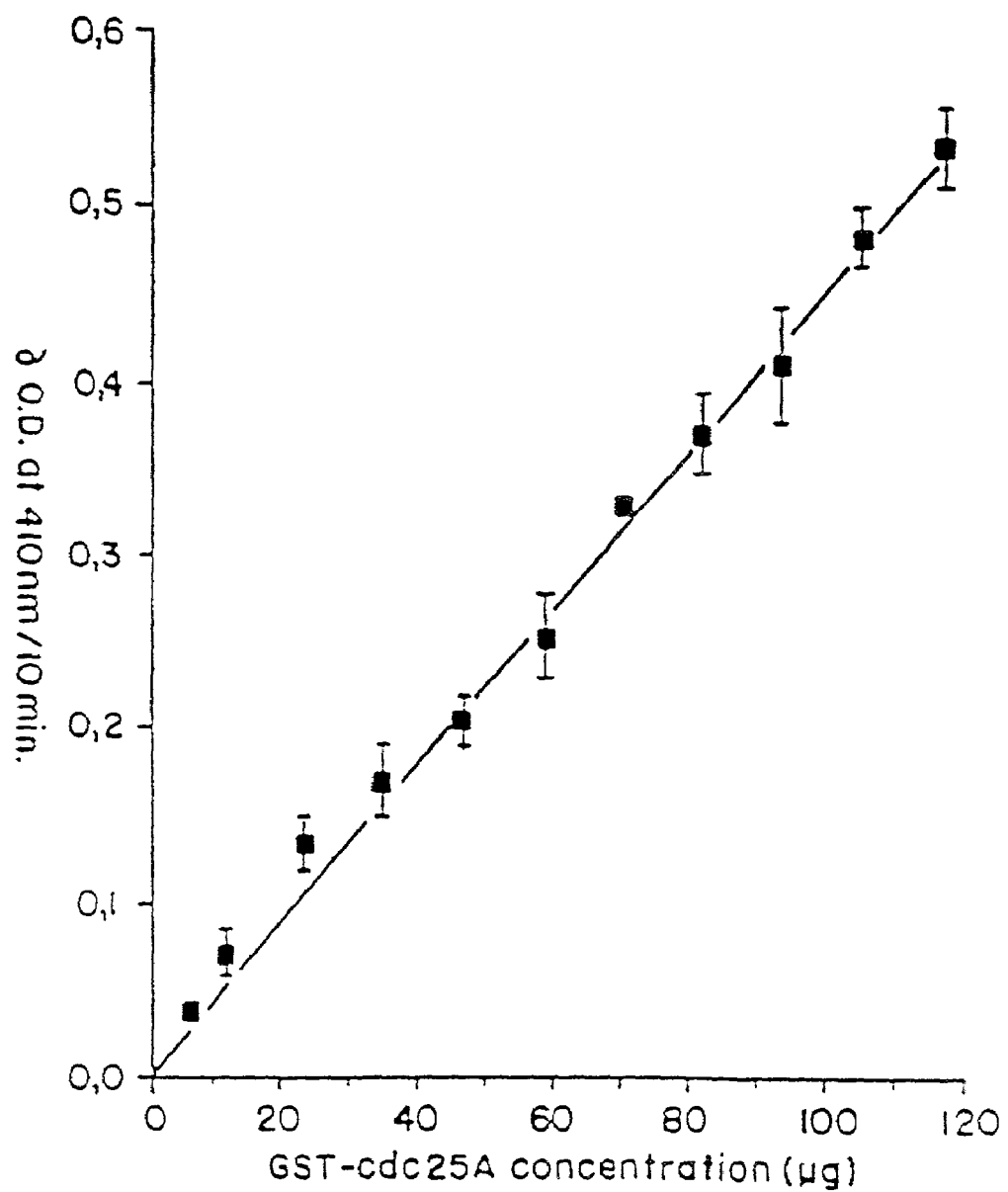
FIGS. 12A–B are graphic representation of GST-cdc25-pNPP phosphatase activity as a function of GST-cdc25A concentration (FIG. 12A) and as a function of duration of assay (FIG. 12B).
Figure 12B:
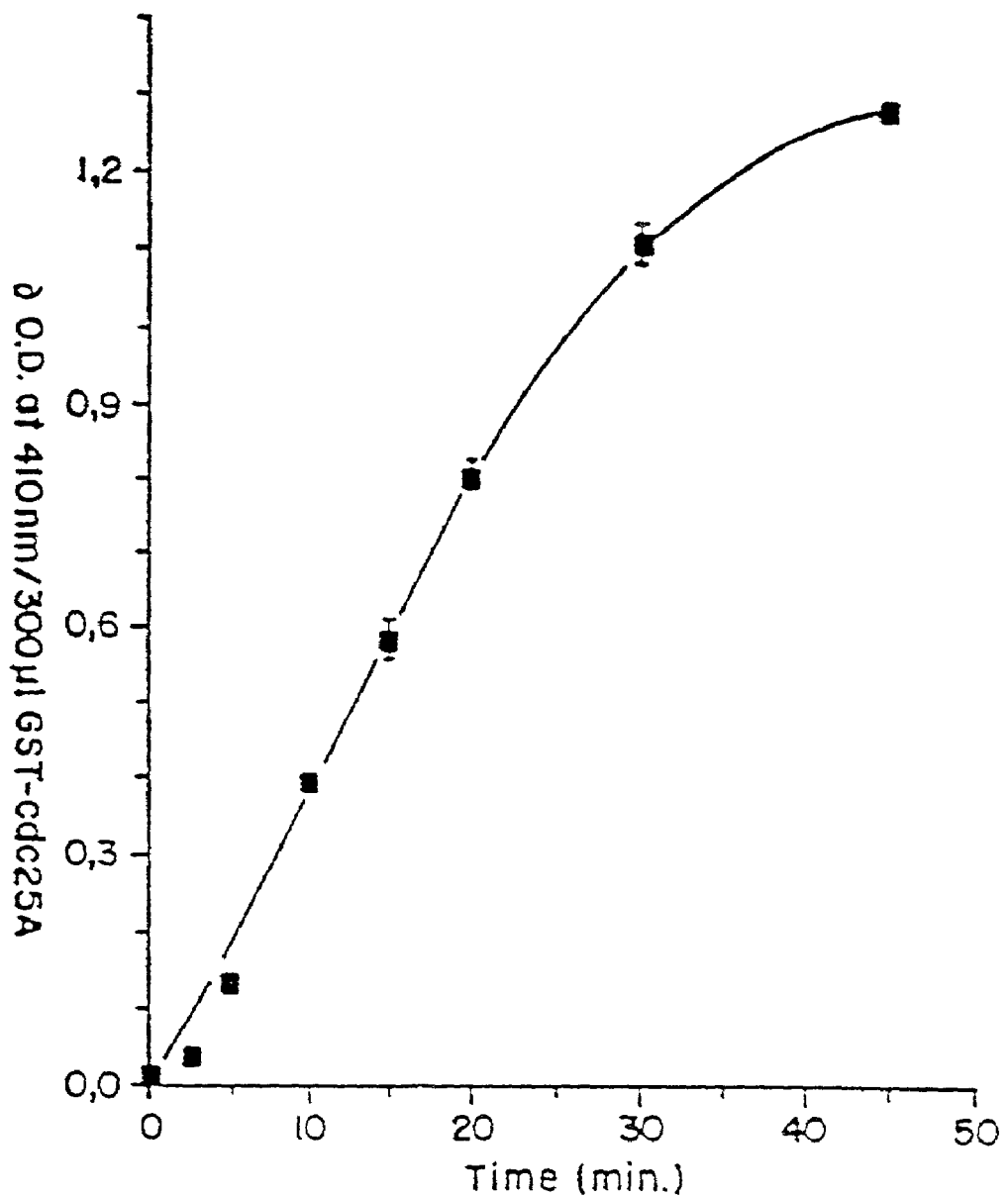
Figure 13A:
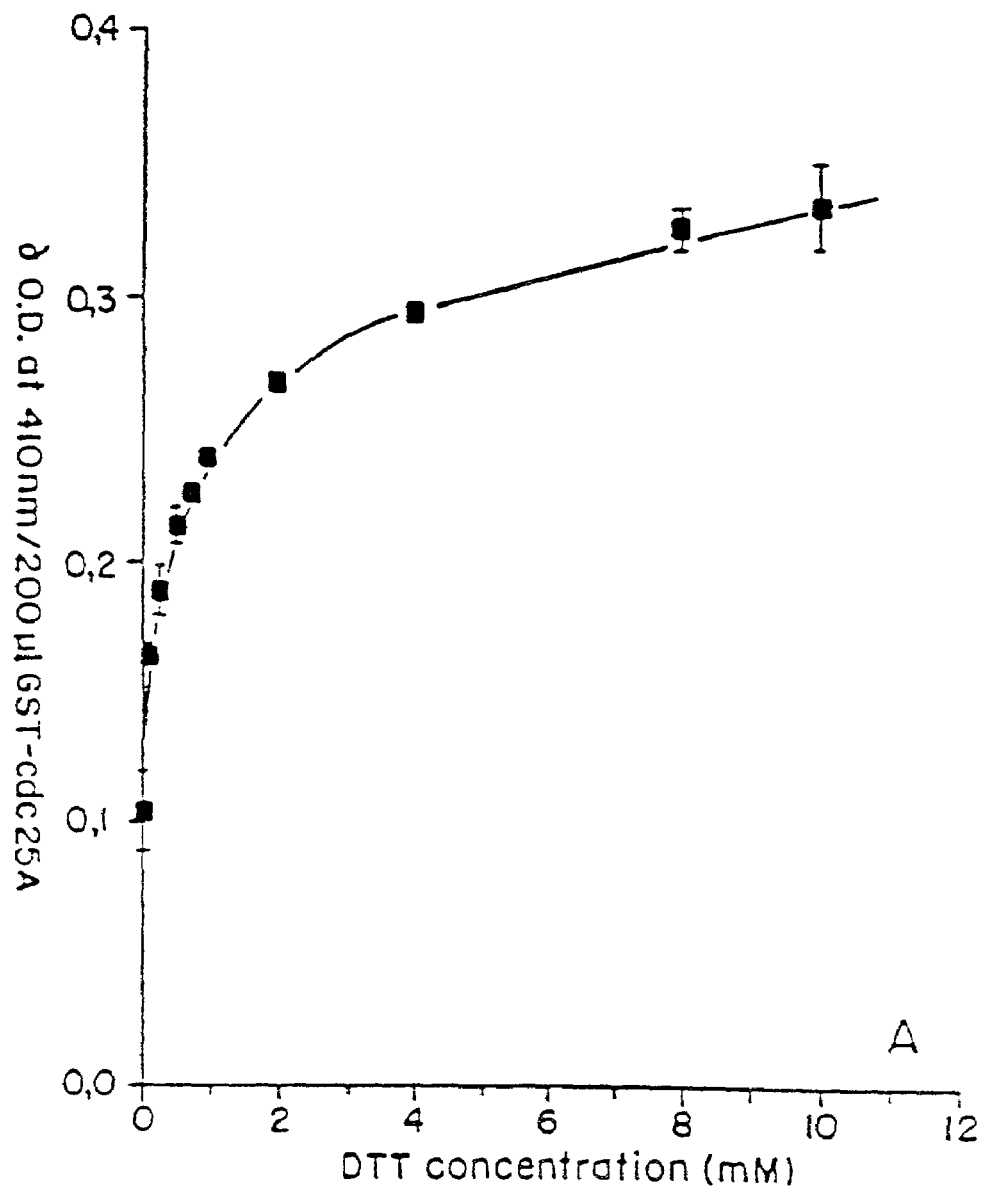
FIGS. 13A–B are graphic representation of GST-cdc25a activity as a function of DTT concentration (FIG. 13A) and p-NPP concentration (FIG. 13B).
Figure 13B:
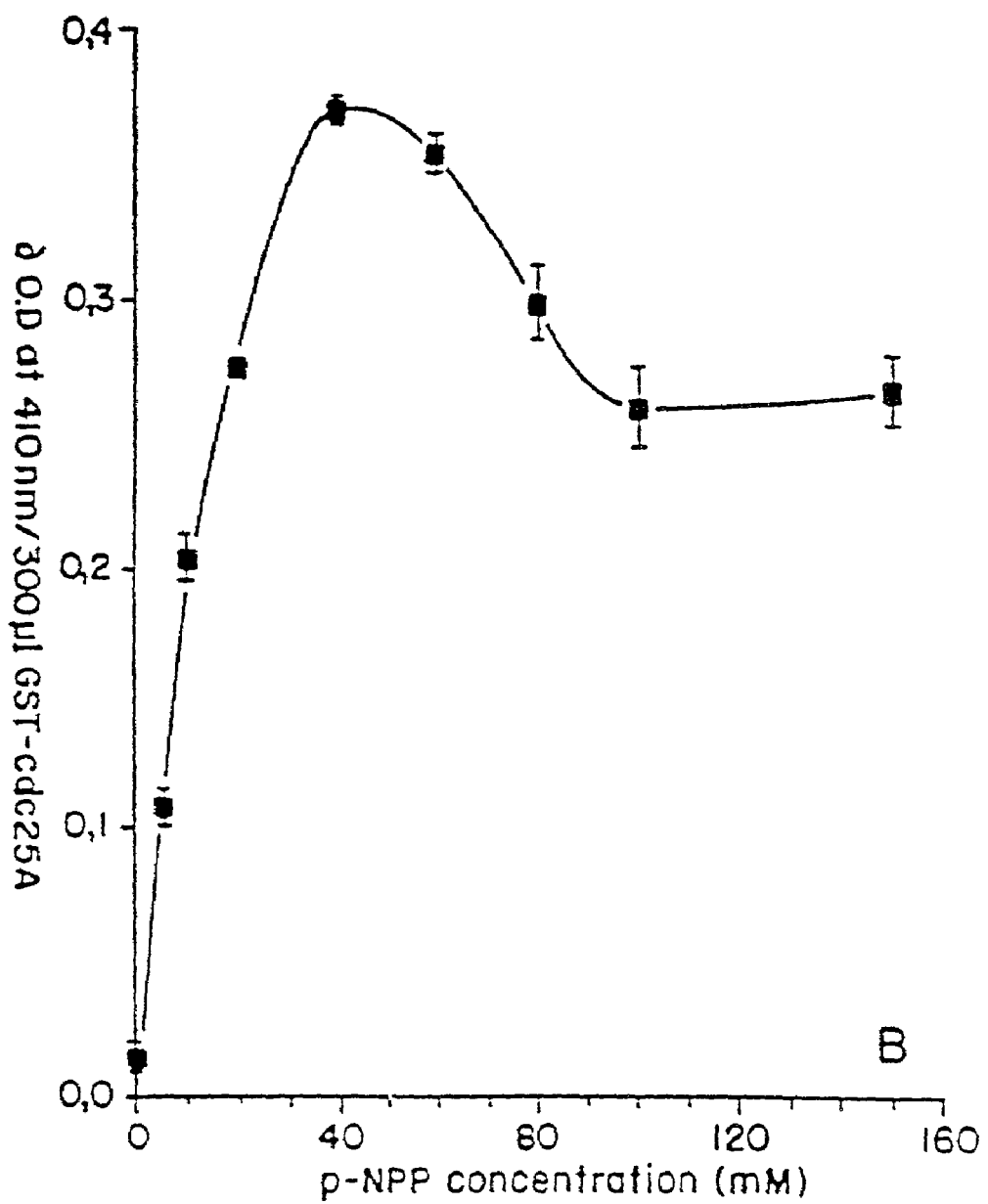

GST-cdc25A phosphatase activity can be very conveniently assayed using the chromogenic substrate p-nitrophenylphosphate (p-NPP). Optimal conditions for several parameters were determined with a one ml assay, as described below. Results are represented graphically in the figures: amount of GST-cdc25A phosphatase (FIG. 12A), duration of assay (FIG. 12B), DTT concentration (FIG. 13A), p-NPP concentration (FIG. 13B).

One ml assay: 100 μl of GST-cdc25A protein (diluted to an activity of ∂ OD 410 nm=0.3/10 min) were mixed with 100 μl mM DTT (in Tris buffer A) and 700 μl of Tris buffer A. The assay was initiated by addition of 100 μl 500 mM p-NPP (in Tris buffer A). After 10 min incubation at 37° C., the assay was terminated by addition of 40 μl 5 N NaOH and transfer of the tubes to 4° C. Absorbance at 410 nm was then measured and blank values (no GST-cdc25A protein but 10 min incubation) were subtracted.

This assay was then scaled down to 200 μl and conducted semi-automatically in 96-wells microtitration plates, as described in detail below. Each well was filled with 20 μl GST-cdc25A phosphatase, 140 μl Tris buffer A, 20 μl 100 mM DTT (in Tris buffer A); after 15 min equilibration at 37° C., reaction was initiated by addition of 20 μl 500 mM p-NPP (in Tris buffer A). After 60 min incubation absorbance at 405 nm was monitored in a microplate reader; blank values (no GST-cdc25A added) were subtracted.

Microtitration plate assay: 20 μl of GST-cdc25A protein (diluted to an activity of a ∂ OD 405 nm=0.2–0.3/60 min)

were mixed with 20 μl 100 mM DTT (in Tris buffer A) and 140 μl of Tris buffer A, in 96-wells microtitration plates (Corning). The plates were preincubated at 37° C. for 15 min in a Denley Wellwarm 1 microplate incubator. The assays were initiated by addition of 20 μl of 500 mM p-NPP (in Tris buffer A). After 60 min incubation at 37° C. absorbance at 405 nm was measured in a bioRad microplate reader. Blank values (no CST-cdc25A protein added) were automatically subtracted.

EXAMPLE 17

Tyrosine Dephosphorylation and Activation of the $p34^{cdc2}$/cyclin $B^{cdc13}$ Kinase by the Fusion Protein GST-cdc25A The ability of the GST-cdc25A fusion protein to dephosphorylate and activate the $p34^{cdc2}$/cyclin $B^{cdc13}$ kinase was demonstrated. $p34^{cdc2}$/cyclin $B^{cdc13}$ complex from G2-arrested starfish oocytes was immobilized on $p9^{CKShs1}$ agarose: it is constituted of tyrosine-phosphorylated $p34^{cdc2}$ and cyclin $B^{cdc13}$ (Arion, L. et al., *Eur. J. Biochem.*: (1992); Pondaven, P. et al., *Genes and Development* 4:9–17 (1990)).

Figure 11:
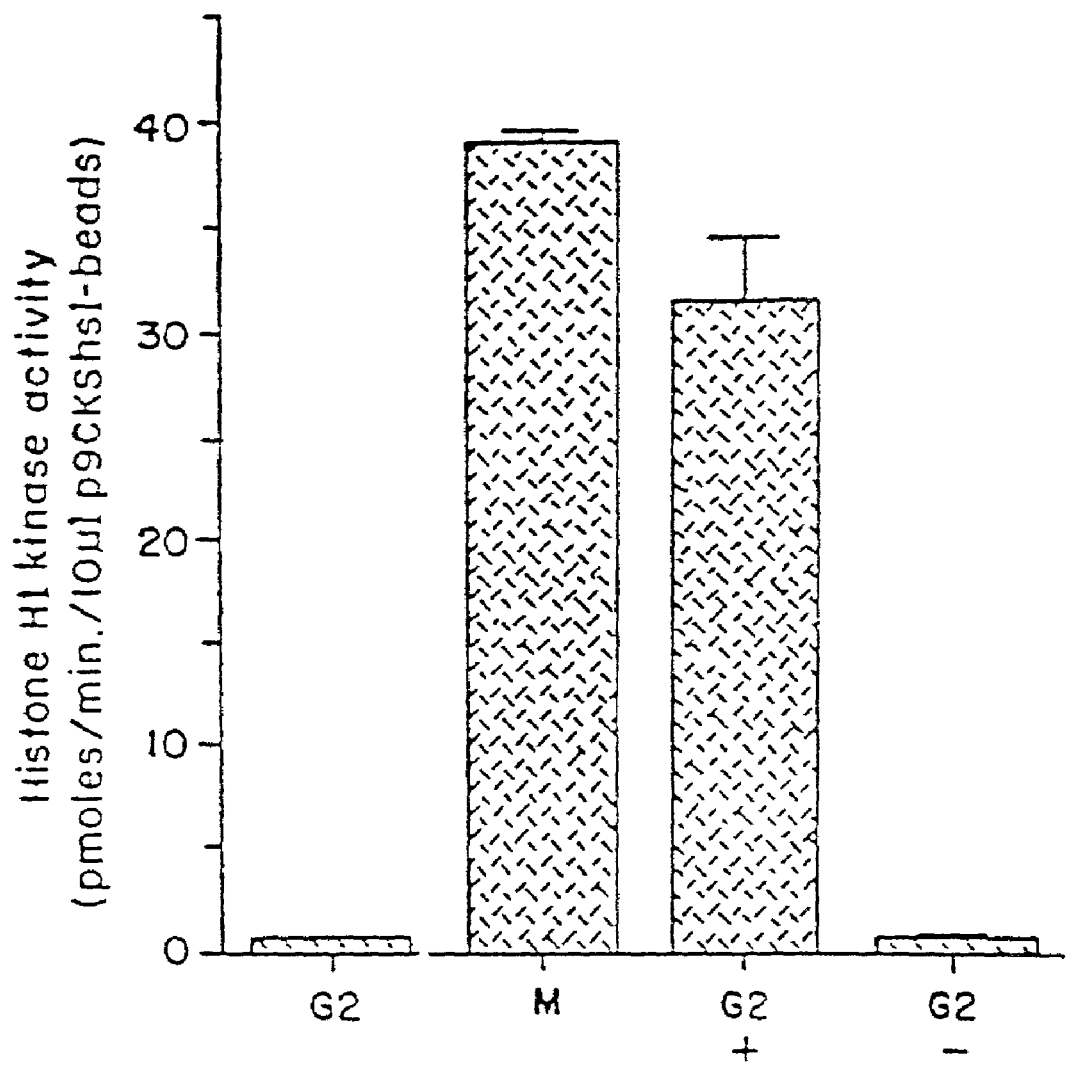
FIG. 11 is evidence that the GST-cdc25a fusion protein dephosphorylates p34$^{cdc2}$ and activates the M phase-specific H1 kinase (MPF).

Treatment with purified GST-cdc25A protein induced almost complete tyrosine dephosphorylation of $p34^{cdc2}$ by the $p34^{cdc2}$ mobility shift, the loss of cross-reactivity with anti-phosphotyrosine antibodies and the appearance of cross-reactivity with an antibody directed against a $p34^{cdc2}$ peptide comprising the tyrosine-15 residue (data not shown). In addition, this tyrosine dephosphorylation lead to histone H1 kinase activation to a level close to that found in M phase oocytes (FIG. 11). By these criteria, the GST-cdc25A fusion protein appears to display all the physiological enzymatic activity of cellular $p80^{cdc25}$.

Assay of $p34^{cdc2}$/Cyclin $B^{cdc13}$ Kinase Activity

Oocyte extracts were prepared by homogenization of 1 g of G2 or M phase gonads per 2 ml homogenization buffer. After centrifugation for 10 min at 14,000 g at 4° C., the supernatants were loaded on $p9^{CKShs1}$-sepharose beads prepared as described in Azzi, L. et al. (*Eur. J. Biochem.*: in press (1992)) (400 μl supernatant/10 μl $p9^{CKShs1}$-beads). The tubes were kept under constant rotation at 4° C. for 30 min. After a brief centrifugation at 10,000 g and removal of the supernatant, the beads were washed three times with bead buffer and eventually exposed to purified GST-cdc25A phosphatase prior to H1 kinase assay or to immunoblotting analysis.

Histone H1 kinase assays were performed by incubation of 10 μl of packed $p_9^{CKShs1}$-beads (loaded with G2 or M phase extracts) for 10 min at 30° C. with 15 μM [γ-32P] ATP (3,000 Ci/mmol; 1 mCi/ml) in the presence of 1 mg histone II1/ml in a final volume of 40 μl. Assays were terminated by transferring the tube onto ice. After a brief centrifugation at 10,000 g, 30 μl aliquots of supernatant were spotted onto 2.5×3 cm pieces of Whatman P81 phosphocellulose paper, and after 20 sec, the filters were washed five times (for at least 5 min each time) in a solution of 10 ml phosphoric acid/liter of water. The wet filters were transferred into 6 ml plastic scintillation vials, 5 ml ACS (Amersham) scintillation fluid was added and the radioactivity of the samples measured in a Packard counter.

Electrophoresis and Western Blotting

Proteins bound to $p9^{CKShS1}$-sepharose beads were recovered with 50 μl 2× Laemmli sample buffer. Samples were run in 10% SDS/polyacrylamide gels. Proteins were stained with Coomassie Blue or transferred to 0.1 μm nitrocellulose sheets (Schleicher & Schull) in a Milliblot/SDE system (Millipore) for 30 min at 2.5 mA/cm² in transfer buffer. The filters were subsequently blocked with TBS containing 3% bovine serum albumin for 1 hr at room temperature. The filters were then incubated overnight at 4° C. with g1 anti-p34cdc2 antibodies (1:1000 dilution), anti-$p34^{cdc2}$ peptide antibodies (1:500 dilution) or anti-phosphotyrosine antibodies (1 μg/ml). After four washes of 15 min each with TBS containing 0.2% NP40, the filters were treated with 1 μCi $^{125}$I-protein A (30 mCi/mg) in 3% bovine serum albumin in TBS for 2 hr at room temperature. After four 15 min washes with 0.2% NP40 in TBS, the filters were exposed overnight to hyperfilm MP (Amersham).

EXAMPLE 18

Detection of Inhibitors of Purified GST-cdc25A Phosphatase

Figure 14:
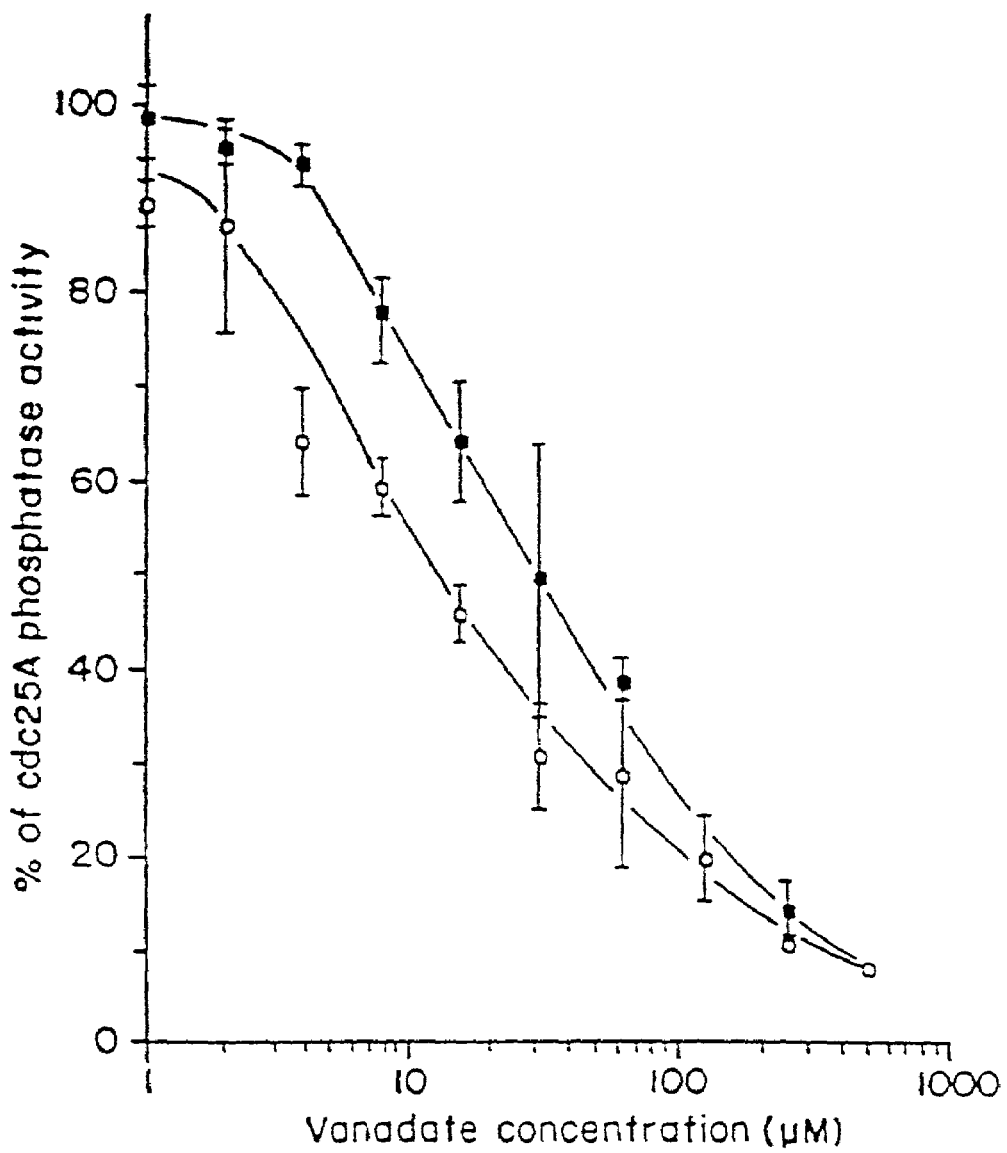
FIG. 14 is a graphic representation of the inhibitory effect of sodium orthovanadate on GST-cdc25A tyrosine phosphatase, in which phosphatase activity is expressed as % of activity in the absence of vanadate (mean ±SD).

In a series of experiments various antimitotic compounds currently used in cancer therapy were tested as potential inhibitors of the phosphatase (the Table). Most of them are reported to act as DNA damaging agents, as DNA intercalators, as topoisomerase 2 inhibitors or as compounds interfering with spindle microtubles. None of them displayed GST-cdc25A phosphatase inhibitory activity. As a positive control vanadate, a reported inhibitor of tyrosine phosphatases was also tested (Gordon, J. A., 1*Methods in Enzymology pp.* 447–482 (1991)). This compound totally inhibits the GST-cdc25A phosphatase at concentrations above 500 μM (FIG. 14; $I_{50}$=20 μM).

TABLE

ANTIMITOTIC COMPOUNDS TESTED AS POTENTIAL INHIBITORS OF $P80^{cdc25A}$

| Compounds | Range of Concentration Tested |
|---|---|
| Actinomycin D | 0.1–100 μg/ml |
| BCNU | 0.1–100 μg/ml |
| Carboplatin | 0.1–100 μg/ml |
| Chlormethine | 0.1–100 μg/ml |
| Cis-platinum | 0.1–100 μg/ml |
| Cyclophosphamide | 0.1–100 μg/ml |
| Dacarbazine | 0.1–100 μg/ml |
| Doxorubicin | 0.1–100 μg/ml |
| Etoposide | 0.1–100 μg/ml |
| Fluoro-uracil | 0.1–100 μg/ml |
| Girolline | 0.36–360 μg/ml |
| Methotrexate | 0.1–100 μg/ml |
| Novobiocin | 0.1–100 μg/ml |
| Vinblastine | 0.1–100 μg/ml |
| Vincristine | 0.1–100 μg/ml |

None of the compounds exhibited more than 5–10% inhibitory activity on the enzyme over the indicated range of concentration.

Equivalents

Those skilled in the art will recognize, or be able to ascertain using not more than routine experimentation, nany equivalents to the specific embodiments of the tnvention described herein. Such equivalents are intended to be encompassed by the following claims.

What is claimed is:

1. A method of inhibiting the transcription and/or translation of a polynucleotide encoding a human CDC25A protein in a cell in vitro, comprising contacting said polynucleotide with an oligonucleotide that
  (i) is complementary to the sequence set forth in SEQ ID NO: 1 or to a portion thereof; and
  (ii) hybridizes to the polynucleotide.

2. The method of claim 1, wherein said human CDC25A protein has endogenous tyrosine phosphatase activity.

3. The method of claim 1, wherein said human CDC25A protein rescues a cdc25-deficient strain of fission yeast.

4. The method of claim 1, wherein said polynucleotide is mRNA.

(i) is complementary to the sequence set forth in SEQ ID NO: 1 or to a portion thereof; and
  (ii) hybridizes to the polynucleotide or to the complement thereof.

5. The method of claim 1, wherein the polynucleotide encoding the human CDC25A protein comprises a sequence as set forth in SEQ ID NO: 1.

6. The method of claim 1, wherein said human CDC25A has the amino acid sequence set forth in SEQ ID NO: 2.

* * * * *

UNITED STATES PATENT AND TRADEMARK OFFICE
CERTIFICATE OF CORRECTION

PATENT NO. : 7,005,258 B1 Page 1 of 1
DATED : February 28, 2006
INVENTOR(S) : Beach et al.

It is certified that error appears in the above-identified patent and that said Letters Patent is hereby corrected as shown below:

<u>Column 38,</u>
Lines 1-4, delete text.

Signed and Sealed this

Thirtieth Day of May, 2006

JON W. DUDAS
*Director of the United States Patent and Trademark Office*